US011672929B2

(12) United States Patent
Mustapha et al.

(10) Patent No.: US 11,672,929 B2
(45) Date of Patent: Jun. 13, 2023

(54) PRODUCT DELIVERY DEVICES AND METHODS

(71) Applicant: BREATHE RESTORE, INC., Long Lake, MN (US)

(72) Inventors: Jihad A. Mustapha, Ada, MI (US); Gary M. Petrucci, Long Lake, MN (US)

(73) Assignee: BREATHE RESTORE, INC., Long Lake, MN (US)

(*) Notice: Subject to any disclaimer, the term of this patent is extended or adjusted under 35 U.S.C. 154(b) by 0 days.

(21) Appl. No.: 17/539,758

(22) Filed: Dec. 1, 2021

(65) Prior Publication Data

US 2022/0168516 A1 Jun. 2, 2022

Related U.S. Application Data

(60) Provisional application No. 63/120,619, filed on Dec. 2, 2020.

(51) Int. Cl.
*A61M 15/00* (2006.01)
(52) U.S. Cl.
CPC ...... *A61M 15/0086* (2013.01); *A61M 15/002* (2014.02); *A61M 15/0013* (2014.02); *A61M 2202/02* (2013.01); *A61M 2205/36* (2013.01); *A61M 2205/82* (2013.01); *A61M 2207/00* (2013.01)

(58) Field of Classification Search
CPC ............ A61M 15/0086; A61M 15/002; A61M 2205/36; A24F 40/10; A24F 40/40; A24F 40/42; A24F 40/46
See application file for complete search history.

(56) References Cited

U.S. PATENT DOCUMENTS

| 2019/0191780 | A1* | 6/2019 | Wilke ...................... A24D 1/20 |
| 2020/0038601 | A1* | 2/2020 | Hepworth ............. A61M 15/06 |
| 2022/0079223 | A1* | 3/2022 | Abi Aoun ............... A24F 40/20 |
| 2022/0132918 | A1* | 5/2022 | Summers ................ A24F 40/40 |
| | | | 131/329 |
| 2022/0218033 | A1* | 7/2022 | Fallon .................... A24F 40/20 |

FOREIGN PATENT DOCUMENTS

| EP | 3295813 | 3/2018 |
| WO | 2018/002085 | 1/2008 |
| WO | 2020/020950 | 1/2020 |

OTHER PUBLICATIONS

International Search Report and Written Opinion of the International Searching Authority, PCT/IB2021/061201, dated Apr. 26, 2022.

* cited by examiner

*Primary Examiner* — Margaret M Luarca
(74) *Attorney, Agent, or Firm* — Merchant & Gould P.C.

(57) ABSTRACT

Devices, and methods for generating variable inhalable products (e.g., variable density, phase, and size products) are provided. Methods for treating or preventing a disorder in a subject using variable products generated by the devices are also provided herein. Additionally, inhalers and breathing systems comprising the devices are provided.

37 Claims, 8 Drawing Sheets

PRODUCT DELIVERY DEVICES AND METHODS

CROSS REFERENCE TO RELATED APPLICATIONS

This application claims the benefit under 35 U.S.C. § 119(e) of U.S. provisional application No. 63/120,619 filed on Dec. 2, 2020, the disclosure of which is herein incorporated by reference in its entirety.

TECHNICAL FIELD

This document relates to delivery devices for producing and delivering variable phase, size, or density products, associated components, inhalation devices, methods for delivery of variable phase, size, density products, and methods for treating and preventing respiratory disorders or conditions in a subject (e.g., a human) or delivering non-therapeutic agents to a subject using such devices. For example, the variable phase, size, or density product delivery devices provided herein can be used in medicinal inhalation devices to generate variable phase or variable density products such as vapor, mist, suspended particles, droplets, or combinations thereof, of a composition (e.g., therapeutic composition) for delivery into at least a portion of a subject's respiratory tract or lungs via inhalation.

BACKGROUND

Various compositions can be inhaled into or delivered to a subject's respiratory tract, e.g., nasopharynx or lungs, to treat or prevent respiratory disorders (e.g., pneumonia, asthma, etc.), provide delivery of non-respiratory therapeutics into a subject's body, treat or prevent non-respiratory disorders (e.g., by inhalable insulin), provide acute opening of a subject's airway (e.g., during mechanical ventilation or an asthma attack), provide delivery of non-therapeutic agents (such as nicotine), and the like. Typically, therapeutic compositions are inhaled or delivered as aerosols, and particularly, fine aerosols. Various devices can provide fine aerosols to a subject's respiratory tract, nasopharynx, or lungs, such as inhalers and nebulizers.

SUMMARY

Although aerosol technology, particularly in the form of inhalers and nebulizers, has been in use for decades, few advancements have been made in therapeutic delivery. Delivery of therapeutic agents via fine aerosol inhalation can result in a loss of therapeutic. There is a Sneed for alternative mechanisms for inhalable delivery of therapeutic and prophylactic agents. Additionally, the generation of aerosols for delivery of a therapeutic can sometimes aid in undesirable transmission of infectious diseases, e.g., within an acute care healthcare environment (for example, aerosol transmission of SARS-CoV-2). Fine aerosols can remain suspended in air for extended time periods, and travel far from the source, allowing for increased transmission of diseases when infectious particles are transported on the fine aerosols. Larger aerosols, including heavy mist, do not travel as far and can preferentially deliver compositions to desired locations with the respiratory system. There is a need for inhalation delivery devices that can generate non-aerosol products, non-fine aerosol products, variable size or density products (e.g., droplets, particles, and the like), heavy mist, or vapor, that allow for targeted and efficient delivery of therapeutic, prophylactic, and diagnostic agents into a subject's respiratory tract, nasopharynx, or lungs, and without the generation of potentially infectious fine aerosol particles. There is also a need for delivery devices that can be tuned to specifically deliver an agent to a targeted region of a subject's respiratory tract, nasopharynx, or lungs.

This document provides delivery devices for delivering variable phase, size, or density products, associated components, and inhalation devices. This document also provides methods for variable phase, size, or density product delivery and methods for treating and preventing respiratory disorders or conditions in a subject (e.g., a human) or delivering non-therapeutic agents to a subject using such devices. This document further provides various breathing systems and devices, including ventilators, comprising such delivery devices.

In some embodiments, methods provided herein can include treatment of subjects requiring mechanical breathing assistance (e.g. mechanical ventilation), spontaneously breathing subjects with artificial airways, or ambulatory subjects capable of independent, spontaneous breathing. In some embodiments, methods provided herein can treat or prevent respiratory disorders and conditions, including bronchospasms, COPD, chronic bronchitis, asthma, emphysema, pulmonary hypertension, interstitial lung disease, pulmonary fibrosis, pneumonia, interstitial pneumonia, lung infections, idiopathic pulmonary fibrosis, covid-19, acute respiratory distress syndrome, and infections such SARS-CoV-2 (or associated COVID-19 illness), coronavirus, SARS-CoV, MERS, and Pertussis.

In one aspect, a delivery device is provided, comprising a first chamber; one or more heating plates, wherein at least a portion of the one or more heating plates is positioned adjacent to a proximal portion of the first chamber; and one or more heating coils surrounding a distal portion of the first chamber. In some embodiments, the delivery device is an inhalation delivery device. In some embodiments, the delivery device or inhalation delivery device can optionally include one or more of the following features. The first chamber can have a proximal end and a distal end and a width or diameter that increases from the proximal end of the first chamber to the distal end of the first chamber. The one or more heating plates have a proximal end that is thinner than a distal end of the heating plates. The one or more heating plates can have a proximal end that is positioned further away from the first chamber than a distal end of the heating plates. The one or more heating plates can be positioned such that the distance between a sidewall of the first chamber and the one or more heating plates decreases along a flow axis. The distal end of the one or more heating plates can be positioned adjacent to the proximal portion of the first chamber. The one or more heating coils can have a proximal end and a distal end and the proximal end of the one or more heating coils can have a smaller diameter than the distal end of the one or more heating coils. The proximal end of the first chamber can be positioned adjacent a portion of the one or more heating plates that lies between the proximal and distal ends of the one or more heating plates. The proximal end of the first chamber can comprise an aperture and the distal end of the first chamber can comprise an aperture. In some embodiments, the distal end of the first chamber comprises a valve.

The device can optionally further comprise a second chamber having a proximal end and a distal end, the first chamber can have a distal end, and the proximal end of the second chamber can be in fluid connection with the distal end of the first chamber. In some embodiments, the device can optionally include one or more of the following features. The second chamber can have a width or diameter greater than the width or diameter of the first chamber at the distal end of the first chamber. The second chamber can be a cooling chamber. The distal end of the second chamber can comprise an aperture. The aperture at the distal end of the second chamber can comprise a valve. The valve can be a one-way valve. The distal end of the second chamber can comprise a subject interface portion. The device can further comprise a vessel receiving region, wherein the vessel receiving region is upstream of the first chamber. The device can further comprise a vessel in fluid communication with the proximal end of the first chamber. The vessel can comprise a therapeutic agent. The vessel can be removable. The device can further comprise a power supply.

In another aspect, an inhaler is provided, comprising a delivery device or inhalation delivery device, the device comprising a first chamber; one or more heating plates, wherein at least a portion of the one or more heating plates is positioned adjacent to a proximal portion of the first chamber; and one or more heating coils surrounding a distal portion of the first chamber, and further comprising a second chamber having a proximal end and a distal end, wherein the first chamber has a distal end, and wherein the proximal end of the second chamber is in fluid connection with the distal end of the first chamber, wherein the delivery device comprises a product substrate. In some embodiments, the product substrate can optionally comprise one or more active agents selected from acetyl cysteine, aclidinium bromide, albuterol, albuterol sulfate, amikacin sulfate, amniotic fluid, an amnion tissue preparation, arformoterol sulfate, atropine sulfate, aztreonam, beclomethasone dipropionate, bitolterol mesylate, budesonide, ciclesonide, cromolyn sodium, desflurane, dexamethasone sodium phosphate, dornase alfa, enflurane, epinephrine, ergotamine tartrate, flunisolide, fluticasone propionate, fomoterol fumarate, glycopyrrolate, halothane, indacaterol maleate, iloprost, insulin, ipratropium bromide, isoetharine hydrochloride, isoflurane, isoproterenol hydrochloride, levalbuterol hydrochloride, levodopa, loxapine, mannitol, metaproterenol sulfate, methacholine chloride, mometasone furoate, nedocromil sodium, nicotine, nitric oxide, olodaterol hydrochloride, pentamidine isethionate, pentetate calcium trisodium, pentetate zinc trisodium, pirbuterol acetate, revefenacin, ribavirin, salmeterol xinafoate, sevoflurane, stem cells, a stem cell preparation, terbutaline sulfate, tetrahydrocannabinol, cannabidiol, tiotropium bromide, tobramycin, trimcinolone acetonide, umeclidinium bromide, vilanterol trifenatate, xenon xe-133, zanamivir, epinephrine, sodium chloride, interferon beta, interferon beta 1-b, interferon beta gene delivery, interferon beta-1a, a BKB2R antagonist (e.g., icatibant), a KLKB1 inhibitor (e.g., ecallantide), androgens (e.g., danazol and stanasolol), recombinant SERPING1 (e.g., berinert, cinryze, haegarda), vitamin D, a HAS2 or HAS3 inhibitor (e.g., hymecromone (4-methylumbelliferone)), timbetasin, and combinations thereof.

In another aspect, a breathing system is provided, comprising a pressure-assisted breathing device; and a delivery device or inhalation delivery device, the device comprising a first chamber; one or more heating plates, wherein at least a portion of the one or more heating plates is positioned adjacent to a proximal portion of the first chamber; and one or more heating coils surrounding a distal portion of the first chamber, and further comprising a second chamber having a proximal end and a distal end, wherein the first chamber has a distal end, and wherein the proximal end of the second chamber is in fluid connection with the distal end of the first chamber, wherein the delivery device comprises a product substrate. In some embodiments, the breathing system can optionally include one or more of the following features. The delivery device can be in fluid communication with an air or oxygen flow channel of the breathing system, and the delivery device can be operably connected to the breathing system to deliver at least a portion of the product substrate into the breathing system. The product substrate can comprise one or more active agents selected from acetyl cysteine, aclidinium bromide, albuterol, albuterol sulfate, amikacin sulfate, amniotic fluid, an amnion tissue preparation, arformoterol sulfate, atropine sulfate, aztreonam, beclomethasone dipropionate, bitolterol mesylate, budesonide, ciclesonide, cromolyn sodium, desflurane, dexamethasone sodium phosphate, dornase alfa, enflurane, epinephrine, ergotamine tartrate, flunisolide, fluticasone propionate, fomoterol fumarate, glycopyrrolate, halothane, indacaterol maleate, iloprost, insulin, ipratropium bromide, isoetharine hydrochloride, isoflurane, isoproterenol hydrochloride, levalbuterol hydrochloride, levodopa, loxapine, mannitol, metaproterenol sulfate, methacholine chloride, mometasone furoate, nedocromil sodium, nicotine, nitric oxide, olodaterol hydrochloride, pentamidine isethionate, pentetate calcium trisodium, pentetate zinc trisodium, pirbuterol acetate, revefenacin, ribavirin, salmeterol xinafoate, sevoflurane, stem cells, a stem cell preparation, terbutaline sulfate, tetrahydrocannabinol, cannabidiol, tiotropium bromide, tobramycin, trimcinolone acetonide, umeclidinium bromide, vilanterol trifenatate, xenon xe-133, zanamivir, epinephrine, sodium chloride, interferon beta, interferon beta 1-b, interferon beta gene delivery, interferon beta-1a, a BKB2R antagonist (e.g., icatibant), a KLKB1 inhibitor (e.g., ecallantide), androgens (e.g., danazol and stanasolol), recombinant SERPING1 (e.g., berinert, cinryze, haegarda), vitamin D, a HAS2 or HAS3 inhibitor (e.g., hymecromone (4-methylumbelliferone)), timbetasin, and combinations thereof.

In another aspect, a method of producing inhalable products is provided, comprising heating a liquid product substrate having a first substrate volume in a vessel comprising a vessel aperture, wherein the aperture is in fluid communication with a first chamber having a proximal portion and a distal portion, and the fluid communication is provided through an aperture in the proximal portion of the first chamber, to produce a mixed product having both gas phase and liquid phase molecules and a second substrate volume that is greater than the first substrate volume. In some embodiments, the method can optionally include one or more of the following features. Heating the liquid product substrate can comprise heating the liquid product substrate at a first heating rate of from about 0.001° C./min to 150° C./min. The method can further comprise heating the mixed product in the first chamber, the vessel, or a combination thereof, to produce a gaseous product having more than at least 80% gas phase molecules. The method can further comprise heating the gaseous product in the first chamber, the vessel, or a combination thereof, to produce a heated gaseous product having a temperature at least 10% higher than the boiling point for the product substrate. The method can further comprise allowing the gaseous product or heated gaseous product to cool to produce a heavy mist product, wherein the heavy mist product comprises particles or droplets having an average diameter of from about 3.5 microns to about 5 microns. Allowing the gaseous product or heated gaseous product to cool can comprise allowing the gaseous product or heated gaseous product to pass into a second chamber in fluid communication with the first chamber, wherein the second chamber has a lower temperature than the first chamber. Allowing the gaseous product or heated gaseous product to cool can comprise allowing the gaseous product or heated gaseous product to pass into a breathing system. Allowing the gaseous product or heated gaseous product to cool can comprise allowing the gaseous product or heated gaseous product to pass into a subject's oral cavity.

In another aspect, a method is provided for treating a subject having a disorder or providing prophylaxis to a subject to prevent or reduce the severity of a developing disorder, the method comprising delivering inhalable products to the subject through a delivery device or inhalation delivery device comprising a first chamber; one or more heating plates, wherein at least a portion of the one or more heating plates is positioned adjacent to a proximal portion of the first chamber; and one or more heating coils surrounding a distal portion of the first chamber. In another aspect, a method is provided for treating a subject having a disorder or providing prophylaxis to a subject to prevent or reduce the severity of a developing disorder, the method comprising delivering inhalable products to the subject through an inhaler comprising a delivery device or inhalation delivery device comprising a first chamber; one or more heating plates, wherein at least a portion of the one or more heating plates is positioned adjacent to a proximal portion of the first chamber; and one or more heating coils surrounding a distal portion of the first chamber. In another aspect, a method is provided for treating a subject having a disorder or providing prophylaxis to a subject to prevent or reduce the severity of a developing disorder, the method comprising delivering inhalable products to the subject through a breathing system comprising a delivery device or inhalation delivery device comprising a first chamber; one or more heating plates, wherein at least a portion of the one or more heating plates is positioned adjacent to a proximal portion of the first chamber; and one or more heating coils surrounding a distal portion of the first chamber. In some embodiments, each of these methods can optionally include one or more of the following features. The inhalable products can comprise one or more active agents selected from acetyl cysteine, aclidinium bromide, albuterol, albuterol sulfate, amikacin sulfate, amniotic fluid, an amnion tissue preparation, arformoterol sulfate, atropine sulfate, aztreonam, beclomethasone dipropionate, bitolterol mesylate, budesonide, ciclesonide, cromolyn sodium, desflurane, dexamethasone sodium phosphate, dornase alfa, enflurane, epinephrine, ergotamine tartrate, flunisolide, fluticasone propionate, fomoterol fumarate, glycopyrrolate, halothane, indacaterol maleate, iloprost, insulin, ipratropium bromide, isoetharine hydrochloride, isoflurane, isoproterenol hydrochloride, levalbuterol hydrochloride, levodopa, loxapine, mannitol, metaproterenol sulfate, methacholine chloride, mometasone furoate, nedocromil sodium, nicotine, nitric oxide, olodaterol hydrochloride, pentamidine isethionate, pentetate calcium trisodium, pentetate zinc trisodium, pirbuterol acetate, revefenacin, ribavirin, salmeterol xinafoate, sevoflurane, stem cells, a stem cell preparation, terbutaline sulfate, tetrahydrocannabinol, cannabidiol, tiotropium bromide, tobramycin, trimcinolone acetonide, umeclidinium bromide, vilanterol trifenatate, xenon xe-133, zanamivir, epinephrine, sodium chloride, interferon beta, interferon beta 1-b, interferon beta gene delivery, interferon beta-1a, a BKB2R antagonist (e.g., icatibant), a KLKB1 inhibitor (e.g., ecallantide), androgens (e.g., danazol and stanasolol), recombinant SERPING1 (e.g., berinert, cinryze, haegarda), vitamin D, a HAS2 or HAS3 inhibitor (e.g., hymecromone (4-methylumbelliferone)), timbetasin, and combinations thereof. The disorder can be a respiratory disorder or a non-respiratory disorder. The respiratory disorder can be selected from chronic obstructive pulmonary disease, asthma, acute asthma, chronic asthma, severe asthma, allergic asthma, bronchial asthma, intrinsic asthma, respiratory distress syndrome of the newborn, reversible respiratory disease, cystic fibrosis, bronchospasms, bronchitis, chronic bronchitis, bronchiectasis, alpha-1 antitrypsin emphysema, emphysema, associated cor pulmonale with pulmonary hypertension, right ventricular hypertrophy and right heart failure, pulmonary hypertension, interstitial lung disease, pulmonary fibrosis, pneumonia, interstitial pneumonia, a lung infection, idiopathic pulmonary fibrosis, cystic fibrosis, tuberculosis, severe acute respiratory syndrome, infection, pulmonary embolus, pulmonary arterial hypertension, pulmonary edema, *pneumocystis* pneumonia, SARS-CoV-2 infection, covid-19, coronavirus, acute respiratory distress syndrome, intensive care unit (ICU) syndrome, systemic inflammatory response syndrome (SIRS), sepsis, severe sepsis, septic shock, or multiple organ dysfunction syndrome (MODS), cystic fibrosis, sarcoidosis, and combinations thereof, and wherein the non-respiratory disorder is selected from an autoimmune disease, a spondyloarthropathy, an intestinal disease, diabetes, a skin disease, a non-respiratory infection, a pain disorder, intensive care unit (ICU) syndrome, systemic inflammatory response syndrome (SIRS), sepsis, severe sepsis, septic shock, or multiple organ dysfunction syndrome (MODS), cystic fibrosis, sarcoidosis, and combinations thereof.

In another aspect, a method is provided for treating a subject having a disorder, comprising administering, to lung tissue of the subject, inhalable products, through an inhaler comprising a delivery device or inhalation delivery device, the device comprising a first chamber; one or more heating plates, wherein at least a portion of the one or more heating plates is positioned adjacent to a proximal portion of the first chamber; and one or more heating coils surrounding a distal portion of the first chamber, and further comprising a second chamber having a proximal end and a distal end, wherein the first chamber has a distal end, and wherein the proximal end of the second chamber is in fluid connection with the distal end of the first chamber, wherein the delivery device comprises a product substrate, wherein the administering occurs through ambulatory inhalation of the inhalable products by the subject from the inhaler. In some embodiments, the disorder optionally can be a non-respiratory disorder or a respiratory disorder, and the administering can occur simultaneously with or after acute treatment of a respiratory disorder.

In another aspect, a method is provided for providing maintenance treatment to a subject following an acute treatment of a respiratory disorder in the subject, comprising administering, to lung tissue of the subject, through a delivery device or inhalation delivery device comprising a first chamber; one or more heating plates, wherein at least a portion of the one or more heating plates is positioned adjacent to a proximal portion of the first chamber; and one or more heating coils surrounding a distal portion of the first chamber, wherein the administering occurs after completion of acute treatment of the subject's respiratory disorder. In another aspect, a method is provided for providing maintenance treatment to a subject following an acute treatment of a respiratory disorder in the subject, comprising administering, to lung tissue of the subject, through an inhaler comprising a delivery device or inhalation delivery device comprising a first chamber; one or more heating plates, wherein at least a portion of the one or more heating plates is positioned adjacent to a proximal portion of the first chamber; and one or more heating coils surrounding a distal portion of the first chamber, wherein the administering occurs after completion of acute treatment of the subject's respiratory disorder. In another aspect, a method is provided for providing maintenance treatment to a subject following an acute treatment of a respiratory disorder in the subject, comprising administering, to lung tissue of the subject, through a breathing system comprising a delivery device or inhalation delivery device comprising a first chamber; one or more heating plates, wherein at least a portion of the one or more heating plates is positioned adjacent to a proximal portion of the first chamber; and one or more heating coils surrounding a distal portion of the first chamber, wherein the administering occurs after completion of acute treatment of the subject's respiratory disorder. In some embodiments, each of these methods can optionally include one or more of the following features. The administering can occur more than 1 day, more than 2 days, more than 3 days, more than 1 week, more than 2 weeks, more than 3 weeks, more than 6 weeks, more than 8 weeks, more than 10 weeks, or more than 15 weeks after the subject has been discharged from hospital care, downgraded from intensive care, downgraded from acute care, downgraded from critical care, or removed from acute care treatment.

In another aspect, a method is provided for regenerating or restoring respiratory tissue or respiratory function in a subject following an acute respiratory disorder in the subject, comprising administering, to lung tissue of the subject, through a delivery device or inhalation delivery device comprising a first chamber; one or more heating plates, wherein at least a portion of the one or more heating plates is positioned adjacent to a proximal portion of the first chamber; and one or more heating coils surrounding a distal portion of the first chamber, inhalable products comprising amniotic fluid, an amnion tissue preparation, or a combination thereof. In another aspect, a method is provided for regenerating or restoring respiratory tissue or respiratory function in a subject following an acute respiratory disorder in the subject, comprising administering, to lung tissue of the subject, through an inhaler comprising a delivery device or inhalation delivery device comprising a first chamber; one or more heating plates, wherein at least a portion of the one or more heating plates is positioned adjacent to a proximal portion of the first chamber; and one or more heating coils surrounding a distal portion of the first chamber, inhalable products comprising amniotic fluid, an amnion tissue preparation, or a combination thereof. In some embodiments, each of these methods can optionally include one or more of the following features. The respiratory disorder can be selected from chronic obstructive pulmonary disease, asthma, acute asthma, chronic asthma, severe asthma, allergic asthma, bronchial asthma, intrinsic asthma, respiratory distress syndrome of the newborn, reversible respiratory disease, cystic fibrosis, bronchospasms, bronchitis, chronic bronchitis, bronchiectasis, alpha-1 antitrypsin emphysema, emphysema, associated cor pulmonale with pulmonary hypertension, right ventricular hypertrophy and right heart failure, pulmonary hypertension, interstitial lung disease, pulmonary fibrosis, pneumonia, interstitial pneumonia, a lung infection, idiopathic pulmonary fibrosis, cystic fibrosis, tuberculosis, severe acute respiratory syndrome, infection, pulmonary embolus, pulmonary arterial hypertension, pulmonary edema, *pneumocystis* pneumonia, SARS-CoV-2 infection, covid-19, coronavirus, and acute respiratory distress syndrome, intensive care unit (ICU) syndrome, systemic inflammatory response syndrome (SIRS), sepsis, severe sepsis, septic shock, or multiple organ dysfunction syndrome (MODS), cystic fibrosis, sarcoidosis, and combinations thereof. The therapeutic agent can be one or more active agents selected from acetyl cysteine, aclidinium bromide, albuterol, albuterol sulfate, amikacin sulfate, amniotic fluid, an amnion tissue preparation, arformoterol sulfate, atropine sulfate, aztreonam, beclomethasone dipropionate, bitolterol mesylate, budesonide, ciclesonide, cromolyn sodium, desflurane, dexamethasone sodium phosphate, dornase alfa, enflurane, epinephrine, ergotamine tartrate, flunisolide, fluticasone propionate, fomoterol fumarate, glycopyrrolate, halothane, indacaterol maleate, iloprost, insulin, ipratropium bromide, isoetharine hydrochloride, isoflurane, isoproterenol hydrochloride, levalbuterol hydrochloride, levodopa, loxapine, mannitol, metaproterenol sulfate, methacholine chloride, mometasone furoate, nedocromil sodium, nicotine, nitric oxide, olodaterol hydrochloride, pentamidine isethionate, pentetate calcium trisodium, pentetate zinc trisodium, pirbuterol acetate, revefenacin, ribavirin, salmeterol xinafoate, sevoflurane, stem cells, a stem cell preparation, terbutaline sulfate, tetrahydrocannabinol, cannabidiol, tiotropium bromide, tobramycin, trimcinolone acetonide, umeclidinium bromide, vilanterol trifenatate, xenon xe-133, zanamivir, epinephrine, sodium chloride, interferon beta, interferon beta 1-b, interferon beta gene delivery, interferon beta-1a, a BKB2R antagonist, a KLKB1 inhibitor, androgens, recombinant SERPING1, vitamin D, a HAS2 or HAS3 inhibitor, timbetasin, and combinations thereof.

In some embodiments, the devices and methods described herein can provide several advantages. First, in some embodiments of the devices provided herein, the devices can be used to generate products, particles, or droplets of varying size, density, or phase for delivery to a subject. For example, in some embodiments of the devices and methods described herein, the products (e.g., a composition) can be delivered to a subject in the form of an aerosol, a fine aerosol, a mist, a heavy mist, a vapor, or a combination thereof. In contrast, existing standard inhalers and nebulizers typically generate only one type of product having a narrow or range or singular phase, size, or density.

Second, in some embodiments, the devices described herein can be tunable to generate a specifically desired product size, density, or phase, or combination thereof, to deliver to a specific location within a subject's respiratory tract. In some embodiments, the devices and methods provided herein can provide higher efficiency delivery of products to a desired location as compared to a standard inhaler or nebulizer. In some embodiments, the devices and methods described herein can advantageously deliver products to a subject with high efficiency. For example, in some embodiments, device and methods described herein can provide higher efficiency delivery of products to a desired location as compared to a standard inhaler or nebulizer. In some embodiments, device and methods described herein can deliver products (e.g., compositions) to a desired location within a subject or a subject's respiratory tract with a loss of product before desired delivery location of less than 50%, less than 40%, less than 30%, less than 20%, less than 10%, or less than 5%.

Third, in some embodiments, the devices and methods described herein can operate in a manner similar to a combination of an inhaler and a nebulizer within a single device, providing a tunable choice between fine aerosol products, mists, or combinations thereof. In addition, in some embodiments described herein, the devices can be small, handheld or portable devices. This advantageously differs from many of the nebulizers currently available, which often require bulky machines, access to a power outlet, and bulky patient interfaces such as large and uncomfortable masks. Furthermore, the multi-use capability of some embodiments of the devices and methods described herein can reduce costs to healthcare facilities and reduce the potential for shortage of devices by providing a single device that can be used for more than one product delivery phase, size, or density. Additionally, some embodiments of the devices described herein can operate in a manner that allows variable density, size, or phase delivery of compositions that may otherwise not be deliverable by devices such as typical inhalers or nebulizers.

The details of one or more embodiments of the invention are set forth in the description below. Other features, objects, and advantages of the invention will be apparent from the description, and from the claims.

Figure 1A:
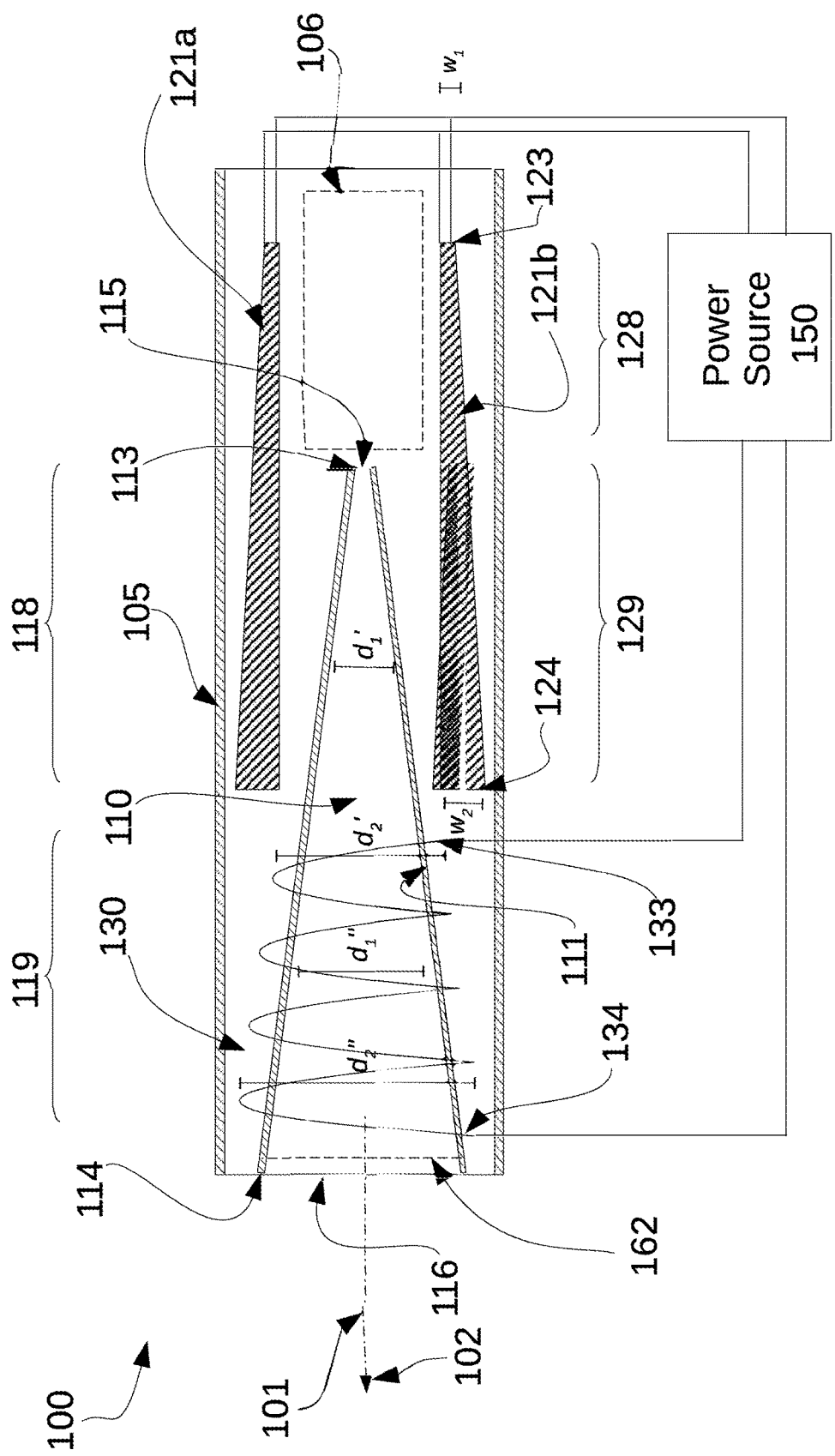
FIG. 1A is a schematic cross-sectional view of an exemplary embodiment of a delivery device shown before insertion of an optional product substrate vessel.

The term "vapor" refers to a gas phase product. In some embodiments, devices described herein can generate, at various time points, a vapor product. In some embodiments, the vapor product generated can later condense and from droplets or an aerosol, such as, e.g., a heavy aerosol or heavy mist.

"Delivery to a subject," "delivering to a subject," "delivery," and the like are used herein interchangeably to refer to the point at which the products described enter the respiratory tract of a subject. For example, in the case of handheld use of devices described herein, such as cases where the end of a device is placed on the lips or into the mouth of the subject, "delivery" occurs when the product reaches the lips or oral cavity of the subject; in some embodiments, at least some of the product then continues into the bronchi and alveoli of the subject. In the case of nasal delivery, "delivery" occurs at the point at which the product reaches the entry of the subject's nose or the nasal cavity; in some embodiments, at least some of the product then continues into the bronchi and alveoli of the subject. In cases where the product enters the subject through an access point other than oral or nasal, such as, e.g., in the case of a subject intubated through tracheotomy, "delivery" occurs when the product reaches the plane of the patient's skin (and, e.g., the tracheostomy) through which the entry point penetrates into the trachea; in some embodiments, at least some of the product then continues into the bronchi and alveoli of the subject.

"Delivery to a desired location within a subject" and the like are used herein to refer to delivery to a specific site within a subject's body. For example, a desired site could be the upper respiratory tract or the lower respiratory tract, the extrathoracic airway, the tracheobronchial airway, the alveoli, the alveolar interstitium, the oral cavity, the nasal cavity, the nasopharyx, and the like. In some embodiments, delivery to the bronchi occurs at the point at which the product reaches the entry of the bronchi. In some embodiments, delivery to the alveoli occurs at the point at which the product reaches the entry of the alveoli.

As used herein, the term "therapeutic," "therapeutic agent", "active agent" or "pharmaceutically active agent" refers to any agent that, when administered to a subject (e.g., an individual), has a therapeutic effect, a diagnostic effect, causes a desired biological or pharmacological effect, or the like. The agent may be used to treat, prevent, or diagnose a disease, or used to otherwise improve physical or mental well-being.

A substrate, product substrate, or product described herein can comprise an "effective amount," a "therapeutically effective amount," or a "prophylactically effective amount" of a therapeutic, a therapeutic agent, an active agent, a prophylactic agent, a pharmaceutically active agent, or the like. "Therapeutically effective amount" refers to an effective amount of an agent (e.g., at the required dosage and over time) to achieve the desired therapeutic result. A therapeutically effective amount of the agent is such that the agent induces the desired response in the subject (e.g., an individual). A therapeutically effective amount can vary according to factors such as the individual subject's disease state, disorder, age, sex, weight, and the like, and can be determined by one skilled in the art, such as a physician. A therapeutically effective amount is also one in which the therapeutically beneficial effect exceeds any toxic or adverse effects of the agent. In some cases, because the devices described herein can, in some embodiments, be more efficient at delivery of an agent to a desired location within a subject, therapeutically effective amounts can be lower than when the agent is delivered by a different delivery device or route, such as a pressurized inhaler, a dry powder inhaler, or a nebulizer. "Prophylactically effective amount" refers to an effective amount at the dosage required to achieve the desired prophylactic result and over the required time. In some cases, since a prophylactic dose is used in subjects prior to or at an earlier stage of a disease or disorder, the prophylactically effective amount will be less than the therapeutically effective amount.

Some embodiments described herein include delivery devices for delivering variable phase, size, or density products, associated components, and inhalation devices, as well as methods for variable phase, size, or density product delivery and methods for treating and preventing respiratory disorders or conditions in a subject (e.g., a human) using such devices.

Delivery of inhalable compositions often occurs through the use of either inhalers, (e.g., pressurized metered dose inhalers, dry powder inhalers, and the like), or through nebulizers. Both of these device types often generate fine-aerosol products for inhalation.

Inhalers are typically medical inhalation devices that dispenses an aerosol. Inhalers, such as metered dose pressurized inhalers (MDIs), and dry powder inhalers (DPIs), are widely used for delivering medicaments. In the case of a pressurized inhaler, the container includes medication that is formulated with a suitable propellant that is filled into an aerosol container. The medication vial is typically used in conjunction with an actuator housing that has a patient interface (e.g., a mouthpiece or a port adapted for nasal use). Inhalers can include metered dose inhalers and pressurized metered dose inhalers. Metered dose inhalers typically produce an aerosol and comprise a medicament or a combination of medicaments and suitable liquefied propellant, such as a propellant selected from the group consisting of HFA 134a, HFA 227 and mixtures thereof.

Nebulizers are drug delivery devices that are used for delivering compositions, typically in liquid form, to a subject's lungs in the form of a liquid aerosol, such as a fine mist, that can be inhaled directly into the lungs. Nebulizers typically use mechanisms such as compressed air, ultrasonic waves, or vibrating mesh to create an aerosol. Some nebulizers have a means for removing larger droplets from the aerosol to ensure a fine mist for delivery to a subject. Exemplary nebulizers can include, but are not limited to, pneumatic nebulizers (e.g., jet nebulizers), mechanical nebulizers (e.g., soft mist inhalers), and electrical nebulizers (e.g., ultrasonic wave nebulizer, vibrating mesh nebulizer, and the like).

Without being bound by theory, it is believed that generation of aerosols for inhalation can, in some circumstances, create conditions for easy transmission of infectious particles, particularly in a health care setting. For example, some hospitalized patients with infectious diseases can receive medications through inhalation, often through generation of fine aerosols by an inhaler or nebulizers. Some of the fine aerosol medicament compositions generated by these devices can be partially inhaled by an infected patient and then exhaled, possibly with an infectious particle transported on one or more of the fine aerosol particles or droplets. In such cases, it is possible that a fine aerosol carrying an infectious particle can remain suspended in the air for several minutes or hours, and can travel distances of several meters or more. In environments where people or animals are kept in close proximity to one another, such as in a hospital, such fine aerosols carrying an infectious particle can be transported between individuals and eventually infect one or more individuals beyond the originally infected and treated subject. Thus, without being bound by theory, it is believed that the treatment of infected subjects with fine aerosol treatment devices can contribute to further spread of infectious diseases that are transportable on aerosol particles, such as, e.g., SARS-CoV-2, other coronaviruses, influenza viruses, and the like. However, many patients with such infectious diseases can benefit from inhalation-based medication protocols. Therefore, there is a need for devices that can generate inhalable products without generating significant fine aerosols, in order to prevent transmission of infectious diseases between individuals in, e.g., healthcare environments, when providing inhalation treatment to infected individuals.

Additionally, successful delivery of compositions (e.g., therapeutic compositions, prophylactic compositions, recreational compositions, and the like) by inhalation can be dependent upon product, particle, or droplet size, density, or phase. For example, it is often considered that particles or droplets in the solid or liquid phase should have sizes ranging from about 0.5 to about 5.0 microns for delivery to the tracheobronchial airway, while other portions of the respiratory tract, such as the extrathoracic airway, or the alveolar interstitium, can utilize different solid or liquid particle or droplet sizes for preferential delivery (Liu, B. (Ed.). (1976). *Fine Particles: Aerosol Generation, Measurement, Sampling, and Analysis* (1st Ed.). Academic Press). As another example, using fine aerosol products for delivery by inhalation can result in the loss of 10%, 20%, 30%, 40%, 50%, 60%, 70%, 80%, or more, of the product to be delivered to a patient before it reaches the desired delivery location, such as the bronchial tree or alveoli. Thus, there is a need for devices that can generate the desired product size, variable density, or phase for delivery to the desired location.

In some embodiments provided herein, the devices can be used to generate products, particles, or droplets of varying size, density, or phase for delivery to a subject. For example, in some embodiments of the devices and methods described herein, products (e.g., a composition) can be delivered to a subject in the form of an aerosol, a fine aerosol, a mist, a heavy mist, a vapor, or a combination thereof. In some embodiments, the devices described herein can be tunable to generate a specifically desired product size, density, or phase, or combination thereof, to deliver to a specific location within a subject's respiratory tract. In some embodiments, the devices and methods provided herein can provide higher efficiency delivery of products to a desired location as compared to a standard inhaler or nebulizer. In some embodiments, the devices and methods described herein can operate in a manner similar to a combination of an inhaler and a nebulizer, providing a tunable choice between fine aerosol products, mists, or combinations thereof.

In some exemplary embodiments, a delivery device described herein provides slow heating of a product substrate. In some embodiments, the product substrate is a liquid substrate, such as a solution or a solid suspended in a liquid. Slow heating of the product substrate can protect the substrate from sudden increases in temperature which can, in some cases, adversely affect the substrate composition. Slow heating can also allow controlled expansion of the liquid substrate as the substrate temperature increases. As the substrate expands with increasing temperature, the substrate migrates from the vessel that originally held the substrate into a chamber that gradually expands in volume and heat increase along the flow direction. The flow direction is the direction in which the product must flow to reach the subject. As the substrate continues to increase in temperature, the substrate slowly becomes a semi-liquid, and then slowly approaches a change to a heavy aerosol or a phase change to vapor. In some embodiments, a substrate heavy aerosol product is formed at or close to the location of delivery to the subject and can immediately be delivered into the subject by inhalation, either by spontaneous breathing or by mechanical ventilation. In some embodiments, a substrate vapor product is formed at or close to the location of delivery to the subject and can immediately be delivered into the subject by inhalation, either by spontaneous breathing or by mechanical ventilation. In some embodiments, a substrate aerosol product is formed (e.g., a fine aerosol or a non-fine aerosol) and the aerosol then passes along the flow direction into a second chamber that is cooler or larger in volume than the first chamber, allowing for condensation and formation of an aerosol mist with increased density or size of the mist or aerosol particles or droplets (e.g., heavy mist), as compared to originally formed aerosol. In some embodiments, a vapor product is formed and the vapor then passes along the flow direction into a second chamber that is cooler or larger in volume than the first chamber, allowing for condensation and formation of an aerosol mist having high density or size particles or droplets of substrate (e.g., heavy mist). In some embodiments, the heavy mist is formed at or close to the location of delivery to the subject and can immediately be delivered into the subject by inhalation, either by spontaneous breathing, or by mechanical ventilation.

Figure 1B:
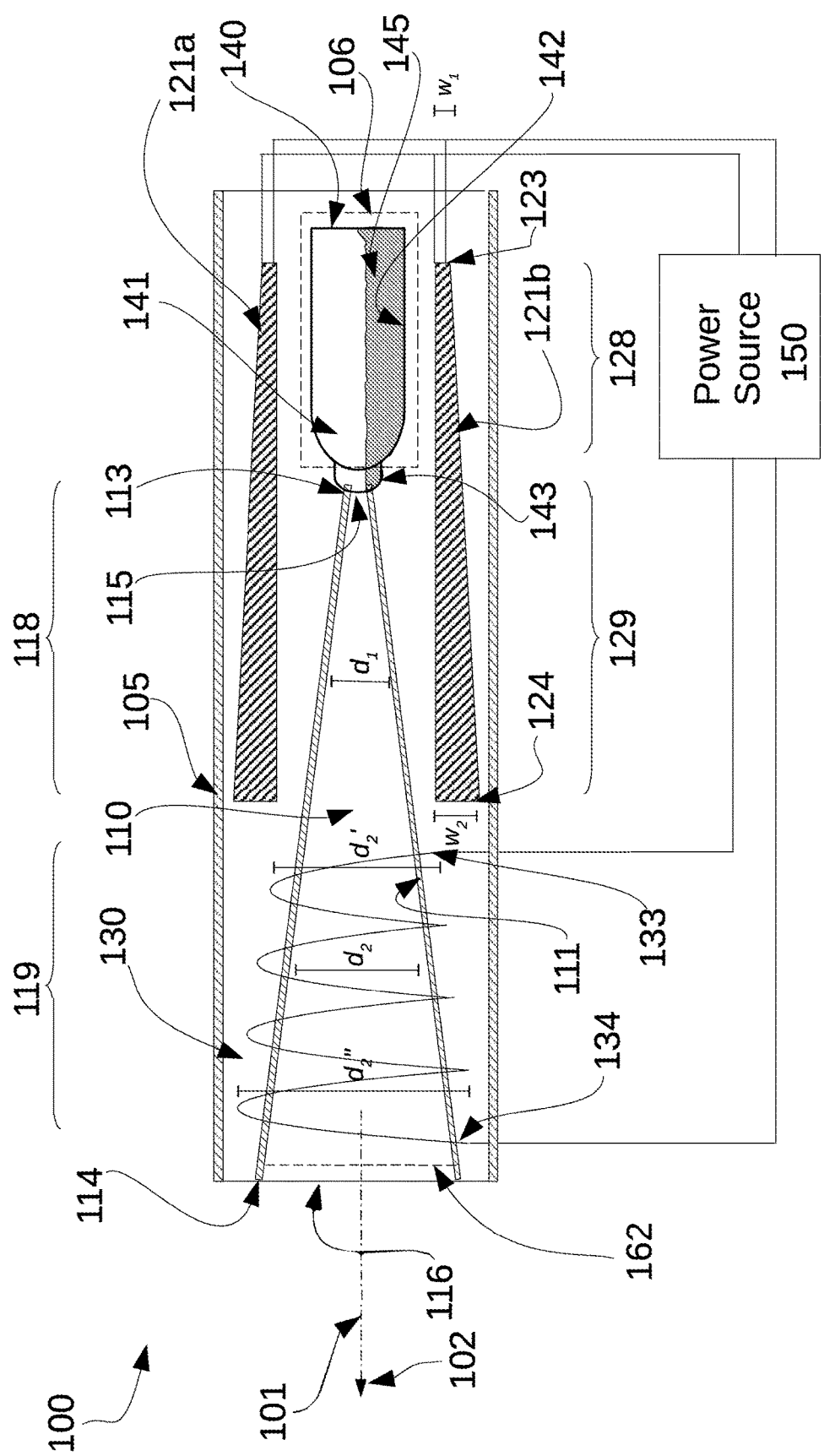
FIG. 1B is a schematic cross-sectional view of the exemplary delivery device of FIG. 1A shown after insertion of an optional product substrate vessel.

Referring now to FIGS. 1A and 1B, a schematic cross-sectional view of an exemplary delivery device 100 is shown. In an exemplary embodiment, the delivery device comprises a first chamber 110, defined by first chamber sidewall 111. In some embodiments, first chamber 110 is a heating chamber. The first chamber has a proximal end 113 and a distal end 114. The proximal end 113 can have an aperture 115. In an exemplary embodiment, a liquid substrate (e.g., a composition or a therapeutic composition, such as substrate 245 in FIG. 1B) or any vaporized form of the substrate (e.g., substrate 145 in FIG. 1B) can enter the first chamber 110 through aperture 115 from a replaceable or non-replaceable vessel (e.g., container 140 in FIG. 1B), in fluid communication with the first chamber 110. In some embodiments, substrate 145 enters first chamber 110 only upon expansion of substrate 145 within container 140 as a result of heating container 140. The distal end 114 can have an aperture 116. In some embodiments, the proximal end aperture 115 of the first chamber 110 can be narrower than the distal end aperture 116 of the first chamber 110. Similarly, the first chamber 110 can have a proximal portion 118 and a distal portion 119. In some optional embodiments, the proximal portion 118 of the first chamber 110 can be narrower than the distal portion 119 of the first chamber 110. In some optional embodiments, the first chamber 110 can have a width or diameter, $d_1$, that increases from the proximal end 113 of first chamber 110 to the distal end 114 of first chamber 110, such that, e.g., a width or diameter, $d_1'$, near the proximal end 113 is less than a width or diameter, $d_1''$, near the distal end 114. The narrower or smaller volume proximal portion 118 of first chamber 110 can aid in increasing surface area contact of the substrate fluid with heat from the heat sources around the proximal portion 118 of first chamber 110 (for example, heating plates 121a and 121b). The wider or larger volume distal portion 119 of first chamber 110 allows steam or vapor forming from the heating of the substrate 145 to expand as it travels along the flow axis 101 in the flow direction 102. In some optional embodiments, the width or diameter, $d_1$, increases at a constant rate from the proximal end 113 of first chamber 110 to the distal end 114 of first chamber 110. In some optional embodiments, the first chamber 110 has an approximately conical shape formed by an approximately conical sidewall 111.

In an exemplary embodiment, the delivery device 100 can optionally comprise external housing 105. The device 100 can have a proximal end 103 and a distal end 104. The device can have any appropriate shape. For example, as in device 100, the device can be substantially cylindrical. In some optional embodiments, the device can be substantially rectangular in shape. In some optional embodiments, the device can be approximately L-shaped or angled in a manned such that the device is shaped like a typical pressurized metered dose inhaler, and can be inserted into the housing of such an inhaler, or operate as a stand-alone device.

In an exemplary embodiment of the device, the distal end aperture 116 of first chamber 110 can optionally be positioned at the end of the device where the device terminates in the flow direction 102. An optional closure mechanism 162 can cover the distal end aperture 116 of the first chamber 110. For example, the closure mechanism 162 can be a cap or end cap for keeping the chamber clean between uses. In some optional embodiments, the closure mechanism 162 can be a valve, such as a one-way valve. A one-way valve can, for example, allow a user to create a negative pressure on the first chamber 110 by positioning the user's mouth around the device at the distal end aperture 116 of first chamber 110 such that the user's lips, together with the housing 105 of the device form a seal, and then inhaling through the user's mouth in a manner similar to the use of an inhaler. The one-way valve would then open during the inhale to allow gas and other products from inside the device to be sucked into the user's mouth and respiratory system, but the one-way valve would close after the inhale without allowing any back-flow into the device. In addition, or alternatively, device 100 can optionally be inserted into another device for use. For example, device 100 can be placed into an inhaler, and the shape can be adjusted as necessary. As another example, a subject interface portion or adapter device, such as, e.g., a mouthpiece, Scan be placed over the distal end 104 of the device 100 when the device is in use.

In an exemplary embodiment, the delivery device can further have one or more heating coils, e.g., 130, surrounding at least a portion of the first chamber 110. For example, in some optional embodiments, the heating coil 130 can surround all or part of distal portion 119 of first chamber 110. As another example, heating coil 130 can surround all of first chamber 110, including distal portion 119 and proximal portion 118. As another example, in some optional embodiments, the heating coil 130 can surround a portion of distal portion 119 of first chamber 110 and a portion of proximal portion 118 of first chamber 110.

The heating coil can be made from any appropriate material. For example, the one or more heating coils can be made from, e.g., resistive wire.

In some optional embodiments, a heating coil 130 can be wound around first chamber 110, such as in a solenoid shape. In some optional embodiments, the heating coil can be wound around the outside of the sidewalls of the first chamber, the inside of the sidewalls of the first chamber, or embedded in the sidewalls of the first chamber. In an exemplary embodiment, heating coil 130 can be wound around the outside of sidewall 111 of first chamber 110. The heating coil 130 has a proximal end 133 and a distal end 134. In optional some embodiments, the coiling of the proximal end 133 of the heating coil 130 can be narrower than the coiling of the distal end 134 of the heating coil 130. In some optional embodiments, the heating coil 130 can have a width or diameter, $d_2$, that increases from the proximal end 133 of heating coil 130 to the distal end 134 of heating coil 130, such that, e.g., a width or diameter, $d_2'$, near the proximal end 133 is less than a width or diameter, $d_2''$, near the distal end 134. In some optional embodiments, the heating coil 130 has an approximately conical shape. One skilled in the art can appreciate that any appropriate heating means can be used in place of heating coil 130 to effect the appropriate desired heating level and increase in first chamber 110. For example, heating coil 130 could be replaced by a series of heating plates in any appropriate configuration, such as a cylindrical or conical wall, or multiple heating plates placed at appropriate angles around first chamber 110. As another example, multiple planes of heating wires can be positioned around first chamber 110. Other possible embodiments of appropriate heating means can be readily envisioned by one skilled in the art.

The heating coil 130 can be positioned such that the coil maintains a desired distance from the first chamber 110, to heat the chamber as desired to the desired use. For example, a delivery device can be designed such that at least a portion of the first chamber reaches a desired temperature at least in part because of the distance between the heating coil and the first chamber 110. In some optional embodiments, the heating coil 130 can be positioned such that an approximately equal distance is maintained between the heating coil 130 and the first chamber 110. In some optional embodiments, the heating coil 130 can be positioned such that a variable distance occurs between the heating coil 130 and the first chamber 110 along the direction of the flow. For example, the heating coil 130 can be positioned, and can be of a selected shape, such that a portion of the heating coil 130 near the proximal end 133 of the heating coil 130 is further away from at least a portion of the first chamber 110 near the proximal end 113 of the first chamber 110 than the distance between a portion of the heating coil 130 near the distal end 134 of the heating coil 130 and at least a portion of the first chamber 110 near the distal end 114 of the first chamber 110.

In an exemplary embodiment, the delivery device can further have one or more heating plates 121a and 121b. For example, the one or more heating plates can be two heating plates positioned on opposite sides of the device, three heating plates placed in a triangular configuration about the device, a single heating plate that is bent or rounded (such as in a cylindrical, conical, or cubic shape about a perimeter of the device). One skilled in the art can appreciate that any appropriate heating means can be used in place of heating plates 121a and 121b to effect the appropriate desired heating level and increase. For example, heating plates 121a and 121b could be replaced by a series of heating wires in any appropriate configuration, such as a coil, multiple planes of wires, etc. As another example, a wall constructed of a heating material can circumscribe the region in place of heating plates 121a and 121b. Other possible embodiments of appropriate heating means can be readily envisioned by one skilled in the art. In an exemplary embodiment, the device can have two heating plates 121a and 121b, positioned opposite each other. At least a portion of the one or more heating plates 121a and 121b is positioned adjacent to the proximal portion 118 of the first chamber 110. The one or more heating plates, e.g., 121b, can have a proximal end 123 and a distal end 124. The one or more heating plates, e.g., 121b, can have a proximal portion 128 and a distal portion 129. In some optional embodiments, the one or more heating plates, e.g., 121b, can have a width, w, that increases from the proximal end 123 of, e.g., heating plate 121b to the distal end 124 of, e.g., heating plate 121b, such that, e.g., a width, w', near the proximal end 123 is less than a width, w'', near the distal end 124. In some optional embodiments, the one or more heating plates, e.g., 121b, can have an approximately flat shape, with a thickness that increase from the proximal end 123 to the distal end 124. In some optional embodiments, the one or more heating plates, e.g., 121b, can have an approximately flat shape, in which the thickness of the distal portion 129 is greater than the thickness of the proximal portion 128. In some optional embodiments, a cross section of the one or more heating plates can have a trapezoidal shape. In some optional embodiments, the distal portion 129 of the one or more heating plates (e.g., 121b) is positioned adjacent to the proximal portion 118 of the first chamber 110 and the proximal portion 128 of the one or more heating plates (e.g., 121b) extends beyond and away from the proximal end 113 of first chamber 110 along a flow axis 101 in a direction opposite the flow direction 102.

In some optional embodiments, the proximal portion 128 of the one or more heating plates (e.g., 121b) can be adjacent an empty space, or a vessel receiving region, within the device. For example, the empty space or vessel receiving can optionally be filled with a vessel containing a product substrate of choice for use in producing variable phase, size, or density products to be delivered (e.g., to a subject) by the device 100. In an exemplary embodiment, as shown in FIG. 1A, the device can have an empty space or vessel receiving region between and adjacent the proximal portion (e.g., 128) of heating plates 121a and 121b. In some optional embodiments, an optional access portion 106 on an optional housing 105 of the delivery device 100 can provide access to the empty space or holder portion inside the device. A user, such as a subject or medical professional or personnel, can open the access portion and insert a vessel containing a product substrate of choice. FIG. 1B shows an exemplary embodiment in which container 140, containing product substrate 145 within reservoir 141, defined by sidewalls 142 of the container 140, has been inserted and placed into fluid communication, through container outlet 143, with aperture 115 of first chamber 110 at the proximal end 113 of first chamber 110. In some optional embodiments, the access portion 106 on optional housing 105 of device 100 can be of any appropriate shape or size, and on any appropriate location on housing 105, to allow for insertion of the container 140 into the device to be placed in fluid communication with first chamber 110.

In an exemplary embodiment, power supply 150 can be used to power the heating plates and heating coils in the device. The power supply can be any source of power, e.g., a mains AC power source such as a wall outlet, a battery, a port of the generator, a DC power source, a generator, a transformer, radio frequency, and the like. For example, in some optional embodiments, the device can be powered by a connection to a wall outlet. In some optional embodiments, the power supply can be internal to the device such that the device can be a handheld, portable device that does not require external power to operate. In some optional embodiments, the power supply can be external to the device, and can be attached to the device during use by way of, e.g., an adaptor cord. In some embodiments, the device can be powered by radio frequency (RF).

In some embodiments, the characteristics of the product formed in first chamber 110 by slow heating of substrate 145 (e.g., phase, density, size, etc.) can be varied depending upon the characteristics of substrate 145, the selected heating rate, the selected heating level, the size or volume of first chamber 110, the proximity of the heating coil 130 to one or more portions of first chamber 110, the size or thickness of the heating coil, the resistivity of the heating coil, the size or thickness of heating plates 121a and 121b, the proximity of heating plates 121a and 121b to the first chamber 110 or the container 140, and similar variables. One skilled in the art can readily adjust such parameters based on the substrate choice and desired end use or desired characteristics of the product output of the device. Similarly, one skilled in the art can develop a device similar to device 200 that has changeable parameters, such as heating temperature or rate of the heating plates 221a and 221b or the heating coil 230 to allow for production of variable products (e.g., variable phase, density, or size) in a single device. Additionally, in some embodiments, when the products produced by the device from the substrate exit the device and enter a subject, the products can further change phase, density, or size characteristics. For example, a product exiting the device in the vapor phase can cool and condense upon entry into a subject's oral or nasal cavity, developing heavier and heavier droplets as it passes through the subject's respiratory system, allowing for deeper and targeted deposition in the subject's lower respiratory tract. As another example, a product exiting the device as a mist or a heavy mist can cool and further condense upon entry into a subject's oral or nasal cavity, developing heavier and heavier droplets as it passes through the subject's respiratory system, allowing for deeper and targeted deposition in the subject's lower respiratory tract. As another example, the device parameters can be chosen to produce a fine aerosol if such is desired for the desired end use.

Figure 2:
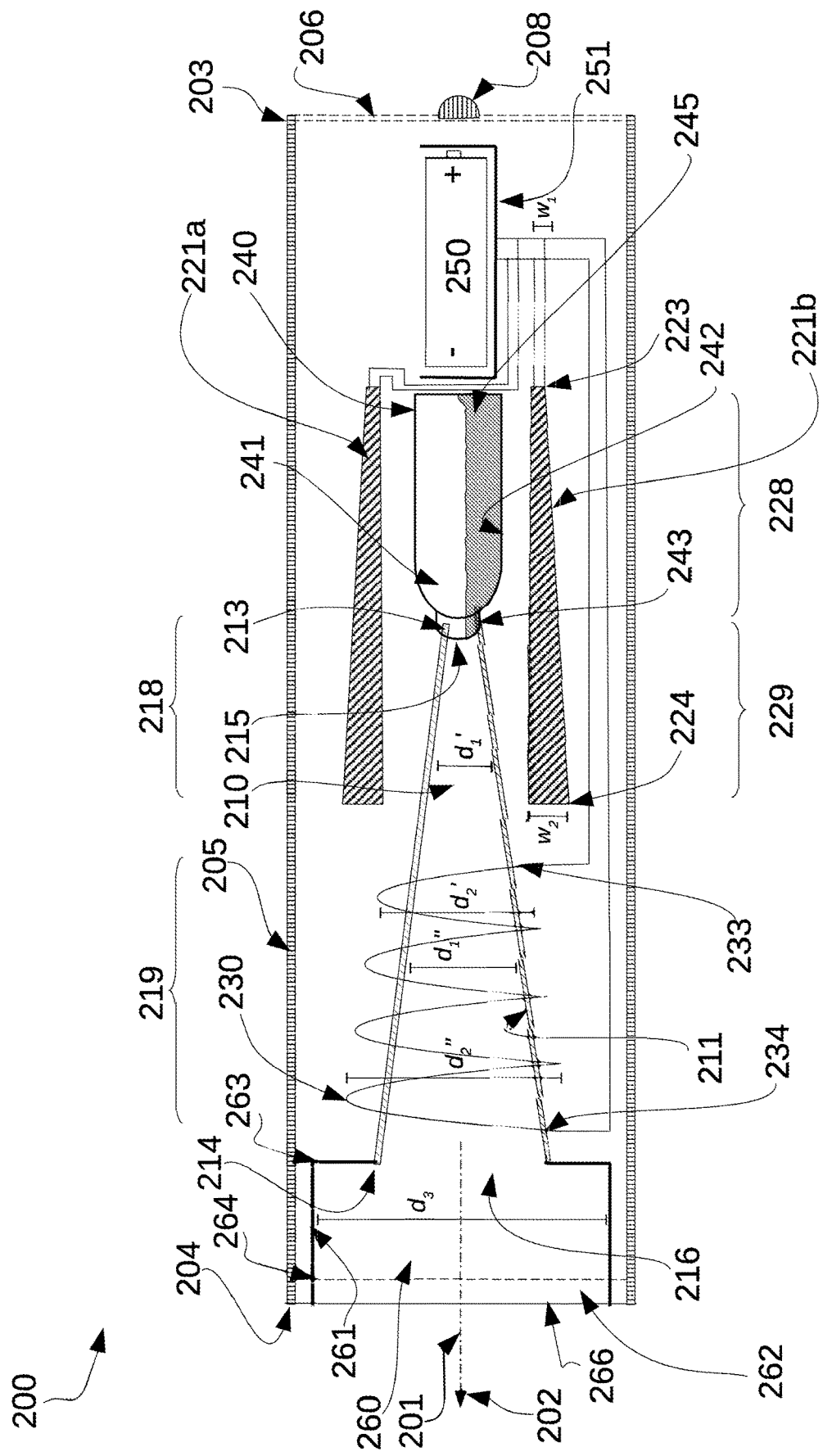
FIG. 2 is a schematic cross-sectional view of an exemplary embodiment of a delivery device.

Referring now to FIG. 2, a schematic cross-sectional view of an exemplary embodiment of a delivery device 200 is shown. In an exemplary embodiment, delivery device 200 is comprised of housing 205. Delivery device 200 can have a proximal end 203 and a distal end 204. In an exemplary embodiment, the delivery device 200 can be substantially cylindrical or rectangular, though other shapes can be used as described herein. Housing 205 can have an optional access portion 206. As shown in FIG. 2, the optional access portion 206 can, in an exemplary embodiment, be on the proximal end 203 of delivery device 200. Additionally, or alternatively, an access portion may be on another portion of the delivery device. Access portion 206 allows access into the device so that a user or physician can optionally change or replace container 240, or power supply 250 in power supply holder 251. In some exemplary embodiments, the delivery device can have more than one access portion (not shown). For example, a first access portion can be provided for access to the area in which container 240 is held for optional insertion, removal, or replacement of container 240, or for optionally refilling container 240 through, e.g., a filling port on container 240 (not shown). Continuing with such exemplary embodiment, a second access portion (not shown) can be provided for separate access to power supply 250. Alternatively, in an optional exemplary embodiment, power supply 250 can be external to the device such that an access portion is not needed for accessing an internal power supply. For example, power supply 250 can be attached to housing 205, on the outside of the device. Alternatively, power supply 250 can be separate from the device and connected via, e.g., an adapter cord when the device is in use. As a further additional or alternative example, power supply 250 can be internal to the device and rechargeable through an external charging device.

Housing 205 can further optionally comprise actuator 208. Actuator 208 can be positioned on any suitable location on housing 205. Actuator 208 acts to turn on the device such that power from the power supply is provided to the one or more heating plates 221a and 221b and the one or more heating coils 230. Circuitry (not shown) can be included to optionally provide current to the heating plates 221a and 221b and heating coil 230 simultaneously, or alternatively, current can be supplied in succession, heating the coils and plates in any desired order or timing, as dependent on the desired use of the device or the desired product substrate in use or desired delivery phase, size, or density. In optional embodiments, additional actuators or user input mechanisms such as knobs, buttons, switches, graphical user interfaces and the like can be included on the device to provide variable control for desired settings and uses. It will be appreciated that a skilled artisan can provide appropriate circuitry and user input design to effect the desired configuration for the desired end use of the device.

In some optional embodiments, the proximal portion 228 of the one or more heating plates (e.g., 221b) can be adjacent an empty space, or a vessel receiving region, within the device. For example, the empty space or vessel receiving region can optionally be filled with a vessel containing a product substrate of choice for use in producing variable phase, size, or density products to be delivered (e.g., to a subject) by the device 200. In an exemplary embodiment, not shown, the device can have an empty space or vessel receiving region between and adjacent the proximal portion (e.g., 228) of heating plates 221a and 221b, to allow for placement of a container (e.g., container 240) containing a product substrate. As described above, in some optional embodiments, an optional access portion 206 on housing 205 of the delivery device 200 can provide access to the empty space or holder portion inside the device. A user, such as a subject or medical professional or personnel, can open the access portion and insert a vessel containing a product substrate of choice. Alternatively, in some embodiments, device 200 can be a single use device, already containing container 240. In some embodiments, container 240 can be refillable through an access port, such as a syringe hole in housing 205 and container sidewall 242. FIG. 2 shows an exemplary embodiment in which container 240, containing product substrate 245 within reservoir 241, defined by sidewalls 242 of the container 240, is in fluid communication, through container outlet 243, with aperture 215 of first chamber 210 at the proximal end 213 of first chamber 210. In some optional embodiments, the access portion 206 on housing 205 of device 200 can be of any appropriate shape or size, and on any appropriate location on housing 205, to allow for insertion of the container 240 into the device to be placed in fluid communication with first chamber 210.

In an exemplary embodiment, the delivery device comprises a first chamber 210, defined by first chamber sidewall 211. In some embodiments, first chamber 210 is a heating chamber. The first chamber has a proximal end 213 and a distal end 214. The proximal end 213 can have an aperture 215. In an exemplary embodiment, a liquid substrate 245 (e.g., a composition or a therapeutic composition) or any vaporized form of the substrate 245 can enter the first chamber 210 through aperture 215 from a replaceable or non-replaceable vessel (e.g., container 240 in FIG. 1B), in fluid communication with the first chamber 210. In some embodiments, substrate 245 enters first chamber 210 only upon expansion of substrate 245 within container 240 as a result of heating container 240. The distal end 214 of first chamber 210 can have an aperture 216. In some embodiments, the proximal end aperture 215 of the first chamber 210 can be narrower than the distal end aperture 216 of the first chamber 210. Similarly, the first chamber 210 can have a proximal portion 218 and a distal portion 219. In some optional embodiments, the proximal portion 218 of the first chamber 210 can be narrower than the distal portion 219 of the first chamber 210. In some optional embodiments, the first chamber 210 can have a width or diameter, $d_1$, that increases from the proximal end 213 of first chamber 210 to the distal end 214 of first chamber 210, such that, e.g., a width or diameter, $d_1'$, near the proximal end 213 is less than a width or diameter, $d_1''$, near the distal end 214. The narrower or smaller volume proximal portion 218 of first chamber 210 can aid in increasing surface area contact of the substrate fluid with heat from the heat sources around the proximal portion 218 of first chamber 210 (for example, heating plates 221a and 221b). The wider or larger volume distal portion 219 of first chamber 210 allows steam or vapor forming from the heating of the substrate 245 to expand as it travels along the flow axis 201 in the flow direction 202. In some optional embodiments, the width or diameter, $d_1$, increases at a constant rate from the proximal end 213 of first chamber 210 to the distal end 214 of first chamber 210. In some optional embodiments, the first chamber 210 has an approximately conical shape formed by an approximately conical sidewall 211.

In an exemplary embodiment, the delivery device can further have one or more heating coils, e.g., 230, surrounding at least a portion of the first chamber 210. For example, in some optional embodiments, the heating coil 230 can surround all or part of distal portion 219 of first chamber 210. As another example, heating coil 230 can surround all of first chamber 210, including distal portion 219 and proximal portion 218. As another example, in some optional embodiments, the heating coil 230 can surround a portion of distal portion 219 of first chamber 210 and a portion of proximal portion 218 of first chamber 210. In some embodiments, the heating coil, in combination with the first chamber 210, can allow for slow heating of substrate 245 to slowly vaporize substrate 245 into a steam. In some alternate embodiments, the heating coil, in combination with the first chamber 210, can allow for slow heating of substrate 245 to slowly form a mist.

The heating coil can be made from any appropriate material. For example, the one or more heating coils can be made from a resistive wire.

In some optional embodiments, a heating coil 230 can be wound around first chamber 210, such as in a solenoid shape. In some optional embodiments, the heating coil can be wound around the outside of the sidewalls of the first chamber, the inside of the sidewalls of the first chamber, or embedded in the sidewalls of the first chamber. In an exemplary embodiment, heating coil 230 can be wound around the outside of sidewall 211 of first chamber 210. The heating coil 230 has a proximal end 233 and a distal end 234. In optional some embodiments, the coiling of the proximal end 233 of the heating coil 230 can be narrower than the coiling of the distal end 234 of the heating coil 230. In some optional embodiments, the heating coil 230 can have a width or diameter, $d_2$, that increases from the proximal end 233 of heating coil 230 to the distal end 234 of heating coil 230, such that, e.g., a width or diameter, $d_2'$, near the proximal end 233 is less than a width or diameter, $d_2''$, near the distal end 234. In some optional embodiments, the heating coil 230 has an approximately conical shape. One skilled in the art can appreciate that any appropriate heating means can be used in place of heating coil 230 to effect the appropriate desired heating level and increase in first chamber 210. For example, heating coil 230 could be replaced by a series of heating plates in any appropriate configuration, such as a cylindrical or conical wall, or multiple heating plates placed at appropriate angles around first chamber 210. As another example, multiple planes of heating wires can be positioned around first chamber 210. Other possible embodiments of appropriate heating means can be readily envisioned by one skilled in the art.

The heating coil 230 can be positioned such that the coil maintains a desired distance from the first chamber 210, to heat the chamber as desired to the desired use. For example, a delivery device can be designed such that at least a portion of the first chamber reaches a desired temperature at least in part because of the distance between the heating coil and the first chamber 210. In some optional embodiments, the heating coil 230 can be positioned such that an approximately equal distance is maintained between the heating coil 230 and the first chamber 210. In some optional embodiments, the heating coil 230 can be positioned such that a variable distance occurs between the heating coil 230 and the first chamber 210 along the direction of the flow. For example, the heating coil 230 can be positioned, and can be of a selected shape, such that a portion of the heating coil 230 near the proximal end 233 of the heating coil 230 is further away from at least a portion of the first chamber 210 near the proximal end 213 of the first chamber 210 than the distance between a portion of the heating coil 230 near the distal end 234 of the heating coil 230 and at least a portion of the first chamber 210 near the distal end 214 of the first chamber 210.

In an exemplary embodiment, the delivery device can further have one or more heating plates 221a and 221b. For example, the one or more heating plates can be two heating plates positioned on opposite sides of the device, three heating plates placed in a triangular configuration about the device, a single heating plate that is bent or rounded (such as in a cylindrical, conical, or cubic shape about a perimeter of the device). One skilled in the art can appreciate that any appropriate heating means can be used in place of heating plates 221a and 221b to effect the appropriate desired heating level and increase. For example, heating plates 221a and 221b could be replaced by a series of heating wires in any appropriate configuration, such as a coil, multiple planes of wires, etc. As another example, a wall constructed of a heating material can circumscribe the region in place of heating plates 221a and 221b. Other possible embodiments of appropriate heating means can be readily envisioned by one skilled in the art. In an exemplary embodiment, the device can have two heating plates 221a and 221b, positioned opposite each other. At least a portion of the one or more heating plates 221a and 221b is positioned adjacent to the proximal portion 218 of the first chamber 210. The one or more heating plates, e.g., 221b, can have a proximal end 223 and a distal end 224. The one or more heating plates, e.g., 221b, can have a proximal portion 228 and a distal portion 229. In some optional embodiments, the one or more heating plates, e.g., 221b, can have a width, w, that increases from the proximal end 223 of, e.g., heating plate 221b to the distal end 224 of, e.g., heating plate 221b, such that, e.g., a width, w', near the proximal end 223 is less than a width, w'', near the distal end 224. In some optional embodiments, the one or more heating plates, e.g., 221b, can have an approximately flat shape, with a thickness that increase from the proximal end 223 to the distal end 224. In some optional embodiments, the one or more heating plates, e.g., 221b, can have an approximately flat shape, in which the thickness of the distal portion 229 is greater than the thickness of the proximal portion 228. In some optional embodiments, a cross section of the one or more heating plates can have a trapezoidal shape. In some optional embodiments, the distal portion 229 of the one or more heating plates (e.g., 221b) is positioned adjacent to the proximal portion 218 of the first chamber 210 and the proximal portion 228 of the one or more heating plates (e.g., 221b) extends beyond and away from the proximal end 213 of first chamber 210 along a flow axis 201 in a direction opposite the flow direction 202.

In an exemplary embodiment, the delivery device 200 can optionally further comprise a second chamber 260, defined by sidewall 261. In some embodiments, first chamber 260 can be a cooling chamber. The second chamber 260 is in fluid communication with first chamber 210, through distal aperture 216 of first chamber 210. The second chamber 260 has a proximal end 263 and a distal end 264. Second chamber 260 is positioned immediately downstream of first chamber 210 along the flow direction, such that the proximal end 263 of second chamber 260 is in fluid communication with distal end 214 of first chamber 210. In some embodiments, second chamber 260 does not have adjacent heat sources such as heating elements, wires, or plates surrounding or adjacent to second chamber 260. In some embodiments, second chamber 260 has a larger width or diameter, $d_3$, than a width or diameter, $d_1''$, near the distal end 214 of first chamber 210. For example, second chamber 260 can have a larger volume than a comparable portion of first chamber 210 having a similar or same length along the flow direction as second chamber 260. In some embodiments, second chamber 260 has a local temperature that is less than a local temperature in first chamber 210. In some embodiments, the larger volume, lower temperature, or combination thereof of second chamber 260 allows for slight cooling of vapor produced throughout first chamber 210, which, in some embodiments, can cause some or all of the vapor produced in first chamber 210 that reaches second chamber 260 to slowly condense to a mist in second chamber 260. The increase in volume, decrease in temperature, slow condensation, or a combination thereof can lead to the production of a mist having an average particle size of from about 2.5 microns to about 4.5 microns, or a heavy mist, e.g., a mist having a particle size of greater than 3.5 microns (such as 3.5-5 microns).

In an exemplary embodiment of the device, an optional closure mechanism 262 can cover the distal end aperture 264 of the second chamber 260. For example, the closure mechanism 262 can be a cap or end cap for keeping the chamber clean between uses. In some optional embodiments, the closure mechanism 262 can be a valve, such as a one-way valve. A one-way valve can, for example, allow a user to create a negative pressure on the second chamber 260 by positioning the user's mouth around the device at the distal end aperture 266 of second chamber 260 such that the user's lips, together with distal end 204 and the housing 205 of the device form a seal, and then inhaling through the user's mouth in a manner similar to the use of an inhaler. The one-way valve would then open during the inhale to allow gas and other products from inside the device to be sucked into the user's mouth and respiratory system, but the one-way valve would close after the inhale without allowing any back-flow into the device. While a simplified rectangular-cross-sectional shape of the distal end 204 is shown for device 200, it will be appreciated that any suitable shape can be used for a subject user interface to allow connection to, e.g., a subject's lips, or other subject interface portion or adapter. For example, the cross sectional shape of distal end 204 of device 200 can, in some embodiments, be other than rectangular, or, in some embodiments, a silicone seal or other similar subject interface portion or adapter can be provided on distal end 204 of device 200. In addition, or alternatively, device 100 can optionally be inserted into another device for use. For example, device 100 can be placed into an inhaler, and the shape can be adjusted as necessary. As another example, a subject interface portion or adapter device, such as, e.g., a mouthpiece, a mask, a nasal mask or cannula, a spacer, a breathing system tubing, and the like, can be placed over the distal end 204 of the device 200 when the device is in use.

In some embodiments, the characteristics of the product formed in first chamber 210 by slow heating of substrate 245 (e.g., phase, density, size, etc.) can be varied depending upon the characteristics of substrate 245, the selected heating rate, the selected heating level, the size or volume of first chamber 210, the proximity of the heating coil 230 to one or more portions of first chamber 210, the size or thickness of the heating coil, the resistivity of the heating coil, the size or thickness of heating plates 221a and 221b, the proximity of heating plates 221a and 221b to the first chamber 210 or the container 240, and similar variables. Similarly, the characteristics of the product formed in second chamber 260 (e.g., phase, density, size, etc.) can be varied depending upon the characteristics of substrate 245, the size or volume of second chamber 260, the heating or non-heating of second chamber 260, the temperature of second chamber 260, the shape of second chamber 260, and similar variable. One skilled in the art can readily adjust such parameters based on the substrate choice and desired end use or desired characteristics of the product output of the device. Similarly, one skilled in the art can develop a device similar to device 200 that has changeable parameters, such as heating temperature or rate of the heating plates 221a and 221b or the heating coil 230 to allow for production of variable products (e.g., variable phase, density, or size) in a single device. Additionally, in some embodiments, when the products produced by the device from the substrate exit the device and enter a subject, the products can further change phase, density, or size characteristics. For example, a product exiting the device in the vapor phase can cool and condense upon entry into a subject's oral or nasal cavity, developing heavier and heavier droplets as it passes through the subject's respiratory system, allowing for deeper and targeted deposition in the subject's lower respiratory tract. As another example, a product exiting the device as a mist or a heavy mist can cool and further condense upon entry into a subject's oral or nasal cavity, developing heavier and heavier droplets as it passes through the subject's respiratory system, allowing for deeper and targeted deposition in the subject's lower respiratory tract. As another example, the device parameters can be chosen to produce a fine aerosol if such is desired for the desired end use.

Figure 3:
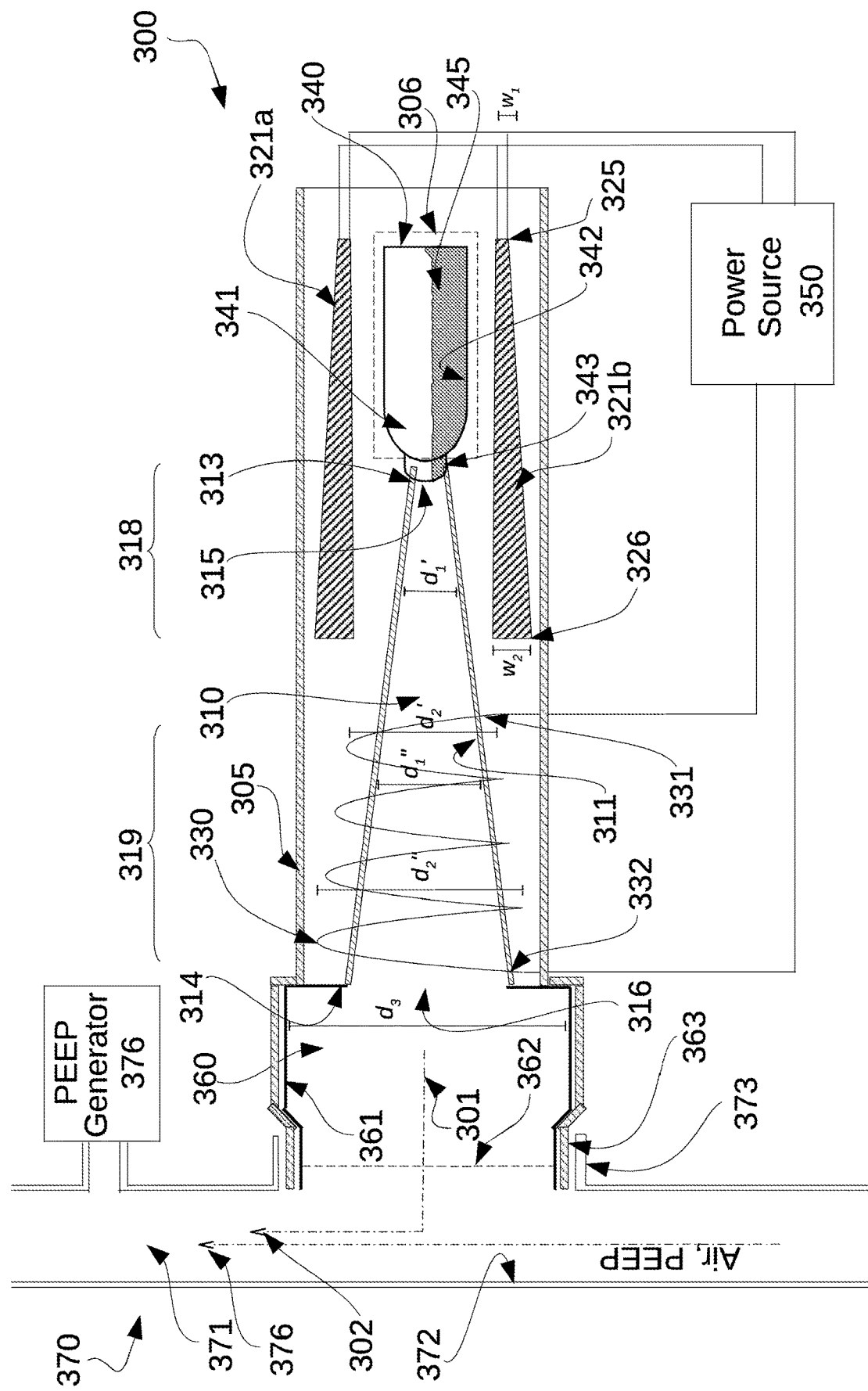
FIG. 3 is a schematic cross-sectional view of an exemplary embodiment of a delivery device as part of an exemplary breathing system.

Referring now to FIG. 3, a schematic cross-sectional view is shown of an exemplary embodiment of a breathing system 370 comprising an exemplary delivery device 300. Breathing systems can deliver inhalation assistance, and optionally, one or more inhalable medications or therapeutic, prophylactic, or diagnostic agents. Breathing systems can include a breathing circuit, such as a ventilator circuit. In some embodiments, breathing system 370 can include, e.g., a mechanical ventilation circuit. In some embodiments, breathing system 370 can comprise a pressure-assisted breathing device, such as a mechanical ventilator, a continuous positive airway pressure system ("CPAP"), a bi-level positive airway pressure system ("BiPAP"), an automatic positive airway pressure system ("APAP"), or an adaptive servo ventilation system ("AVS").

In an exemplary embodiment, delivery device 300 comprises a first chamber 310, defined by first chamber sidewall 311. In some embodiments, first chamber 310 is a heating chamber. The first chamber has a proximal end 313 and a distal end 314. The proximal end 313 can have an aperture 315. In an exemplary embodiment, a liquid substrate 345 (e.g., a composition or a therapeutic composition) or any vaporized or aerosolized form of the substrate 345 (depending upon the substrate, heating variables, etc. as discussed herein) can enter the first chamber 310 through aperture 315 from a replaceable or non-replaceable vessel (e.g., container 340 in FIG. 1B), in fluid communication with the first chamber 310. In some embodiments, substrate 345 enters first chamber 310 only upon expansion of substrate 345 within container 340 as a result of heating container 340. The distal end 314 of first chamber 310 can have an aperture 316. In some embodiments, the proximal end aperture 315 of the first chamber 310 can be narrower than the distal end aperture 316 of the first chamber 310. Similarly, the first chamber 310 can have a proximal portion 318 and a distal portion 319. In some optional embodiments, the proximal portion 318 of the first chamber 310 can be narrower than the distal portion 319 of the first chamber 310. In some optional embodiments, the first chamber 310 can have a width or diameter, $d_1$, that increases from the proximal end 313 of first chamber 310 to the distal end 314 of first chamber 310, such that, e.g., a width or diameter, $d_1'$, near the proximal end 313 is less than a width or diameter, $d_1''$, near the distal end 314. The narrower or smaller volume proximal portion 318 of first chamber 310 can aid in increasing surface area contact of the substrate fluid with heat from the heat sources around the proximal portion 318 of first chamber 310 (for example, heating plates 321a and 321b). The wider or larger volume distal portion 319 of first chamber 310 allows steam or vapor forming from the heating of the substrate 345 to expand as it travels along the flow axis 301 in the flow direction 302. In some optional embodiments, the width or diameter, $d_1$, increases at a constant rate from the proximal end 313 of first chamber 310 to the distal end 314 of first chamber 310. In some optional embodiments, the first chamber 310 has an approximately conical shape formed by an approximately conical sidewall 311.

In an exemplary embodiment, the delivery device can have one or more heating plates 321a and 321b. For example, the one or more heating plates can be two heating plates positioned on opposite sides of the device, three heating plates placed in a triangular configuration about the device, a single heating plate that is bent or rounded (such as in a cylindrical, conical, or cubic shape about a perimeter of the device). One skilled in the art can appreciate that any appropriate heating means can be used in place of heating plates 321a and 321b to effect the appropriate desired heating level and increase. For example, heating plates 321a and 321b could be replaced by a series of heating wires in any appropriate configuration, such as a coil, multiple planes of wires, etc. As another example, a wall constructed of a heating material can circumscribe the region in place of heating plates 321a and 321b. Other possible embodiments of appropriate heating means can be readily envisioned by one skilled in the art. In an exemplary embodiment, the device can have two heating plates 321a and 321b, positioned opposite each other. At least a portion of the one or more heating plates 321a and 321b is positioned adjacent to the proximal portion 318 of the first chamber 310. The one or more heating plates, e.g., 321b, can have a proximal end 323 and a distal end 324. The one or more heating plates, e.g., 321b, can have a proximal portion 328 and a distal portion 329. In some optional embodiments, the one or more heating plates, e.g., 321b, can have a width, w, that increases from the proximal end 323 of, e.g., heating plate 321b to the distal end 324 of, e.g., heating plate 321b, such that, e.g., a width, w', near the proximal end 323 is less than a width, w", near the distal end 324. In some optional embodiments, the one or more heating plates, e.g., 321b, can have an approximately flat shape, with a thickness that increase from the proximal end 323 to the distal end 324. In some optional embodiments, the one or more heating plates, e.g., 321b, can have an approximately flat shape, in which the thickness of the distal portion 329 is greater than the thickness of the proximal portion 328. In some optional embodiments, a cross section of the one or more heating plates can have a trapezoidal shape. In some optional embodiments, the distal portion 329 of the one or more heating plates (e.g., 321b) is positioned adjacent to the proximal portion 318 of the first chamber 310 and the proximal portion 328 of the one or more heating plates (e.g., 321b) extends beyond and away from the proximal end 313 of first chamber 310 along a flow axis 301 in a direction opposite the flow direction 302.

In some optional embodiments, the proximal portion 328 of the one or more heating plates (e.g., 321b) can be adjacent an empty space, or a vessel receiving region, within the device. For example, the empty space or vessel receiving region can optionally be filled with a vessel containing a product substrate of choice for use in producing variable phase, size, or density products to be delivered (e.g., to a subject) by the device 300. In an exemplary embodiment, not shown, the device can have an empty space or vessel receiving region between and adjacent the proximal portion (e.g., 328) of heating plates 321a and 321b, to allow for placement of a container (e.g., container 340) containing a product substrate.

Housing 305 can have an optional access portion 306 to, e.g., provide access to the empty space or holder portion inside the device. A user, such as a subject or medical professional or personnel, can open an optional access portion described above and insert a vessel containing a product substrate of choice. As shown in FIG. 3, the optional access portion 306 can, in an exemplary embodiment, be on a sidewall of housing 305. Additionally, or alternatively, in some embodiments, an access portion can be on another portion of the delivery device 300, such as the proximal end 303 of delivery device 300. Access portion 306 can allow access into the device so that a subject user, physician, or the like can optionally change or replace container 340, or, in cases where power supply 350 is optional stored internally within device 300, a subject user, physician, or the like can optionally replace power supply 350. In some exemplary embodiments, the delivery device 300 can have more than one access portion (not shown). For example, a first access portion can be provided for access to the area in which container 340 is held for optional insertion, removal, or replacement of container 340, or for optionally refilling container 340 through, e.g., a filling port on container 340 (not shown). Continuing with such an exemplary embodiment, a second access portion (not shown) can be provided for separate access to an internal power supply, for servicing and maintenance, or for other similar desired access. In some optional embodiments, power supply 350 can be external to the device. In such cases, it is possible that an access portion may not be needed for accessing an internal power supply. For example, power supply 350 can be attached to housing 305, on the outside of the device. Alternatively, power supply 350 can be separate from the device and connected via, e.g., an adapter cord when the device is in use. As a further additional or alternative example, power supply 350 can be internal to the device and rechargeable through an external charging device.

In some embodiments, device 300 can be a single use device, already containing container 340. In some embodiments, such as where device 300 is a single use device, an access portion may not be present or may not be required for refilling the device, but in some embodiments, access portions may still be present on devices that do not require refill access, such as for accessing a power supply, providing device maintenance, or increasing ease of assembly. In some embodiments, container 340 can be refillable through an access port, such as a syringe hole in housing 305 and container sidewall 342. FIG. 3 shows an exemplary embodiment in which container 340, containing product substrate 345 within reservoir 341, defined by sidewalls 342 of the container 340, is in fluid communication, through container outlet 343, with aperture 315 of first chamber 310 at the proximal end 313 of first chamber 310. In some optional embodiments, the access portion 306 on housing 305 of device 300 can be of any appropriate shape or size, and on any appropriate location on housing 305, to allow for insertion of the container 340 into the device to be placed in fluid communication with first chamber 310.

In an exemplary embodiment, the delivery device can have one or more heating coils, e.g., 330, surrounding at least a portion of the first chamber 310. For example, in some optional embodiments, the heating coil 330 can surround all or part of distal portion 319 of first chamber 310. As another example, heating coil 330 can surround all of first chamber 310, including distal portion 319 and proximal portion 318. As another example, in some optional embodiments, the heating coil 330 can surround a portion of distal portion 319 of first chamber 310 and a portion of proximal portion 318 of first chamber 310. In some embodiments, the heating coil, in combination with the first chamber 310, can allow for slow heating of substrate 345 to slowly vaporize substrate 345 into a steam. In some alternate embodiments, the heating coil, in combination with the first chamber 310, can allow for slow heating of substrate 345 to slowly form a mist.

In some optional embodiments, a heating coil 330 can be wound around first chamber 310, such as in a solenoid shape. In some optional embodiments, the heating coil can be wound around the outside of the sidewalls of the first chamber, the inside of the sidewalls of the first chamber, or embedded in the sidewalls of the first chamber. In an exemplary embodiment, heating coil 330 can be wound around the outside of sidewall 311 of first chamber 310. The heating coil 330 has a proximal end 333 and a distal end 334. In optional some embodiments, the coiling of the proximal end 333 of the heating coil 330 can be narrower than the coiling of the distal end 334 of the heating coil 330. In some optional embodiments, the heating coil 330 can have a width or diameter, $d_2$, that increases from the proximal end 333 of heating coil 330 to the distal end 334 of heating coil 330, such that, e.g., a width or diameter, $d_2'$, near the proximal end 333 is less than a width or diameter, $d_2''$, near the distal end 334. In some optional embodiments, the heating coil 330 has an approximately conical shape. One skilled in the art can appreciate that any appropriate heating means can be used in place of heating coil 330 to effect the appropriate desired heating level and increase in first chamber 310. For example, heating coil 330 could be replaced by a series of heating plates in any appropriate configuration, such as a cylindrical or conical wall, or multiple heating plates placed at appropriate angles around first chamber 310. As another example, multiple planes of heating wires can be positioned around first chamber 310. Other possible embodiments of appropriate heating means can be readily envisioned by one skilled in the art.

The heating coil 330 can be positioned such that the coil maintains a desired distance from the first chamber 310, to heat the chamber as desired to the desired use. For example, a delivery device can be designed such that at least a portion of the first chamber reaches a desired temperature at least in part because of the distance between the heating coil and the first chamber 310. In some optional embodiments, the heating coil 330 can be positioned such that an approximately equal distance is maintained between the heating coil 330 and the first chamber 310. In some optional embodiments, the heating coil 330 can be positioned such that a variable distance occurs between the heating coil 330 and the first chamber 310 along the direction of the flow. For example, the heating coil 330 can be positioned, and can be of a selected shape, such that a portion of the heating coil 330 near the proximal end 333 of the heating coil 330 is further away from the at least a portion of the first chamber 310 near the proximal end 313 of the first chamber 310 than the distance between a portion of the heating coil 330 near the distal end 334 of the heating coil 330 and at least a portion of the first chamber 310 near the distal end 314 of the first chamber 310.

In an exemplary embodiment, the delivery device 300 can comprise a second chamber 360, defined by sidewall 361. In some embodiments, first chamber 360 can be a cooling chamber. The second chamber 360 is in fluid communication with first chamber 310, through distal aperture 316 of first chamber 310. The second chamber 360 has a proximal end 363 and a distal end 364. Second chamber 360 is positioned immediately downstream of first chamber 310 along the flow direction, such that the proximal end 363 of second chamber 360 is in fluid communication with distal end 314 of first chamber 310. In some embodiments, second chamber 360 does not have adjacent heat sources such as heating elements, wires, or plates surrounding or adjacent to second chamber 360. Alternatively, in some embodiments (not shown), second chamber 360 has adjacent heat sources such as heating elements, wires, or plates surrounding or adjacent to second chamber 360. In some embodiments, second chamber 360 has a larger width or diameter, $d_3$, than a width or diameter, $d_1''$, near the distal end 314 of first chamber 310. In some embodiments, second chamber 360 has a width or diameter, $d_3$, that is the same as a width or diameter, $d_1''$, near the distal end 314 of first chamber 310. In some embodiments, second chamber 360 can have a larger volume than a comparable portion of first chamber 310 having a similar or same length along the flow direction as second chamber 360. In some embodiments, second chamber 360 has a local temperature that is less than a local temperature in first chamber 310. In some embodiments, second chamber 360 has a local temperature that is the same as a local temperature in first chamber 310. In some embodiments, second chamber 360 acts as a holding chamber for product ready to be released from device 300 and delivered into the breathing system, subject, or the like. In some embodiments, second chamber 360 has a set of conditions such as a temperature or volume that allows products produced in first chamber 310 to maintain the same phase, density, or size in second chamber 360 as the products exhibited immediately prior to exiting first chamber 310. In some embodiments, a larger volume, lower temperature, or combination thereof of second chamber 360, or other conditions of second chamber 360, allow for slight cooling of vapor produced throughout first chamber 310, which, in some embodiments, can cause some or all of the vapor produced in first chamber 310 that reaches second chamber 360 to slowly condense to a mist in second chamber 360. The increase in volume, decrease in temperature, slow condensation, or a combination thereof can lead to the production of mist having an average particle size of from about 2.5 microns to about 4.5 microns, or a heavy mist, e.g., a mist having an average particle size greater than 3.5 microns (such as 3.5 microns-5 microns). In the optional embodiment shown in FIG. 3, second chamber 360 is shaped such that a desired volume of second chamber 360 can be maintained while also allowing the device to fit into breathing system adaptive interface 373 as described further below, or to be comfortably fitted to a subject's lips. In some embodiments, the desire shape, volume, and other characteristics of second chamber 360 can be chosen by one skilled in the art according to the desired end use of device 300.

In an exemplary embodiment, delivery device 300 is attached to, and in fluid communication with breathing system 370. Delivery device 300, comprised of housing 305 has a proximal end 303 and a distal end 304. Distal end 304 of delivery device 300 has a delivery device adaptive interface 363, which can cooperatively interface with a breathing system adaptive interface 373 to provide connection and fluid communication between delivery device 300 and breathing system 370. Breathing system adaptive interface 373 can be in any appropriate location on a breathing system (e.g., ventilation circuit), such as, e.g., on oxygen flow tubing. Generally, the breathing system adaptive interface 373 is a universal connection point provided on common breathing systems and is of a standard size. Delivery device adaptive interface 363 can be shaped and sized so as to appropriately fit and connect with universal connection points on standard breathing systems or breathing circuits. Additionally, delivery device adaptive interface 363 can be shaped and sized so as to appropriately fit and connect with a subject user by providing a shape and size appropriate for a tight seal with a subject's lips, or with other subject user interface parts such as masks, spacers, and the like. This universal shape and size allows a single device to be usable as both a hand-held device used in direct connection to a subject, or as a tertiary device hooked up to a breathing system for connection to a subject. In some embodiments, breathing system adaptive interface 373 or deliver device adaptive interface 363 can readily be adapted by one skilled in the art to provide an appropriate connection where non-universal breathing equipment is used. Additionally, the connection between breathing system 370 and delivery device 300 at breathing system adaptive interface 373 and delivery device adaptive interface 363 can, in some embodiments, be made by use of an additional adaptor mechanism or piece located between breathing system adaptive interface 373 and delivery device adaptive interface 363, such as, e.g., an extra valve piece or joint piece, additional tubing, reducer, spacer, union piece, coupling, or the like, depending on the circumstances, available equipment, and desired end use of the delivery device and breathing system. In an exemplary embodiment, such as that depicted in FIG. 3, the delivery device 300 or delivery device adaptive interface 363 can be substantially cylindrical. In some embodiments, the delivery device 300 or delivery device adaptive interface 363 can be substantially rectangular, or any other appropriate shape.

Breathing system adaptive interface 373 provides fluid communication between device 300 and breathing system 370, through distal end 304 of device 300, and, for example, either through optional second chamber 360 (as shown in FIG. 3), or through first chamber 310 in devices where optional second chamber 360 is not present (not shown in FIG. 3). Breathing system adaptive interface 373 provides access into the oxygen or gas flow tubing of breathing system 370, either directly, or through a joint, spacer, or other portion of the breathing system. In an exemplary embodiment, breathing system adaptive interface 373 leads directly into oxygen flow tubing 371 of breathing system 370. Products generated by device 300 exit distal end 304 of device 300 in the device direction of flow 302, being pulled into oxygen flow tubing 370 by negative pressure generated in the tubing by the positive end expiratory pressure (PEEP) ventilation circuit. The phase, size, and density of the products generated by device 300 are such that the products are immediately sucked into the oxygen flow tubing and swept quickly in the direction of gas flow 376 into a subject and the subject's respiratory system with the normal operation of a mechanical ventilation circuit. In some embodiments, the products condense or further condense upon entry into flow tubing 371, the subject, or a combination thereof. In some embodiments, the products exit device 300 and enter flow tubing 371 as a heavy mist. In some embodiments, the products exit device 300 and enter flow tubing 371 as a vapor and quickly become a heavy mist within the flow tubing 371 of breathing system 370, with the subject, or a combination thereof.

In an exemplary embodiment of the device, an optional closure mechanism 362 can cover the distal end aperture 364 of the second chamber 360. For example, the closure mechanism 362 can be a cap or end cap for keeping the chamber clean between uses. In some optional embodiments, the closure mechanism 362 can be a valve, such as a one-way valve. A one-way valve can, for example, allow a breathing system or a user to create a negative pressure on the second chamber 360 (e.g., by the positive end expiratory pressure mechanical ventilation, or by positioning the user's mouth around the device at the distal end aperture 366 of second chamber 360 such that the user's lips, together with distal end 304 and the housing 305 of the device form a seal, and then inhaling through the user's mouth in a manner similar to the use of an inhaler). The one-way valve would open due to negative pressure (e.g., externally generated by a breathing system, or by an inhale) to allow gas and other products from inside the device to be sucked into the breathing system and eventually the user's mouth and respiratory system, but the one-way valve would not allow any back-flow into the device. In some alternate embodiments, rather than opening the one-way valve with negative pressure from, e.g., an inhale or mechanical ventilation, the one-way valve can be opened by increasing the pressure upstream of the one-way valve, e.g., in the second chamber 360 or the first chamber 310. In some embodiments, an increase in pressure upstream of the one-way valve can be initiated by applying external to first chamber 310 or second chamber 360. Such external pressure can be applied, for example, through a number of alternate routes, such as by a mechanism within device 300 that is either automatically or manually activated, or by manually applying pressure (e.g., squeezing) to first chamber 310 or second chamber 360 in embodiments of the device that provide open access to first chamber 310 or second chamber 360. In some embodiments, a desired product density, product mass density, product particle density, active agent mass density, inhalable active agent mass density, or inhalable product particle density can be delivered to a subject or expelled from the device by controlling the amount of negative pressure applied to the one-way valve (or external pressure applied to first chamber 310 or second chamber 360 to open the one-way valve).

While a simplified rectangular-cross-sectional shape of the distal end 304 is shown for device 300, it will be appreciated that any suitable shape can be used for a subject user interface to allow connection to, e.g., a breathing system adaptive interface 373, a subject's lips, or other subject interface portion or adapter. For example, the cross-sectional shape of distal end 304 of device 300 can, in some embodiments, be other than rectangular, or, in some embodiments, a silicone seal or other similar subject interface portion or adapter or breathing system adapter can be provided on distal end 304 of device 300.

In some embodiments, the characteristics of the product formed in first chamber 310 by slow heating of substrate 345 (e.g., phase, density, size, etc.) can be varied depending upon the characteristics of substrate 345, the selected heating rate, the selected heating level, the size or volume of first chamber 310, the proximity of the heating coil 330 to one or more portions of first chamber 310, the size or thickness of the heating coil, the resistivity of the heating coil, the size or thickness of heating plates 321*a* and 321*b*, the proximity of heating plates 321*a* and 321*b* to the first chamber 310 or the container 340, and similar variables. Similarly, the characteristics of the product formed in second chamber 360 (e.g., phase, density, size, etc.) can be varied depending upon the characteristics of substrate 345, the size or volume of second chamber 360, the heating or non-heating of second chamber 360, the temperature of second chamber 360, the shape of second chamber 360, and similar variable. One skilled in the art can readily adjust such parameters based on the substrate choice and desired end use or desired characteristics of the product output of the device. Similarly, one skilled in the art can develop a device similar to device 300 that has changeable parameters, such as heating temperature or rate of the heating plates 321*a* and 321*b* or the heating coil 330 to allow for production of variable products (e.g., variable phase, density, or size) in a single device. Additionally, in some embodiments, when the products produced by the device from the substrate exit the device and enter a subject, the products can further change phase, density, or size characteristics. For example, a product exiting the device in the vapor phase can cool and condense upon entry into a subject's oral or nasal cavity, developing heavier and heavier droplets as it passes through the subject's respiratory system, allowing for deeper and targeted deposition in the subject's lower respiratory tract. As another example, a product exiting the device as a mist or a heavy mist can cool and further condense upon entry into a subject's oral or nasal cavity, developing heavier and heavier droplets as it passes through the subject's respiratory system, allowing for deeper and targeted deposition in the subject's lower respiratory tract. As another example, the device parameters can be chosen to produce a fine aerosol if such is desired for the desired end use.

In some embodiments, housing 305 can optionally comprise an actuator (not shown). An optional actuator can be positioned on any suitable location on housing. An actuator can act to turn on the device such that power from the power supply is provided to the one or more heating plates 321*a* and 321*b* and the one or more heating coils 330. Circuitry (not shown) can be included to optionally provide current to the heating plates 321*a* and 321*b* and heating coil 330 simultaneously, or alternatively, current can be supplied in succession, heating the coils and plates in any desired order or timing, as dependent on the desired use of the device or the desired product substrate in use or desired delivery phase, size, or density. In optional embodiments, additional actuators or user input mechanisms such as knobs, buttons, switches, graphical user interfaces and the like can be included on the device to provide variable control for desired settings and uses. It will be appreciated that a skilled artisan can provide appropriate circuitry and user input design to effect the desired configuration for the desired end use of the device. Additionally, in some embodiments, such as, e.g., in devices where an external power supply is used, the device may turn on or actuate automatically upon insertion of a cable or adapter connecting an external power supply to the device. In some optional embodiments, actuators may be included in the housing material such that touch sensors initiate actuation upon holding the device in a specific position, touching lips to the device, or other similar means.

Figure 4A:
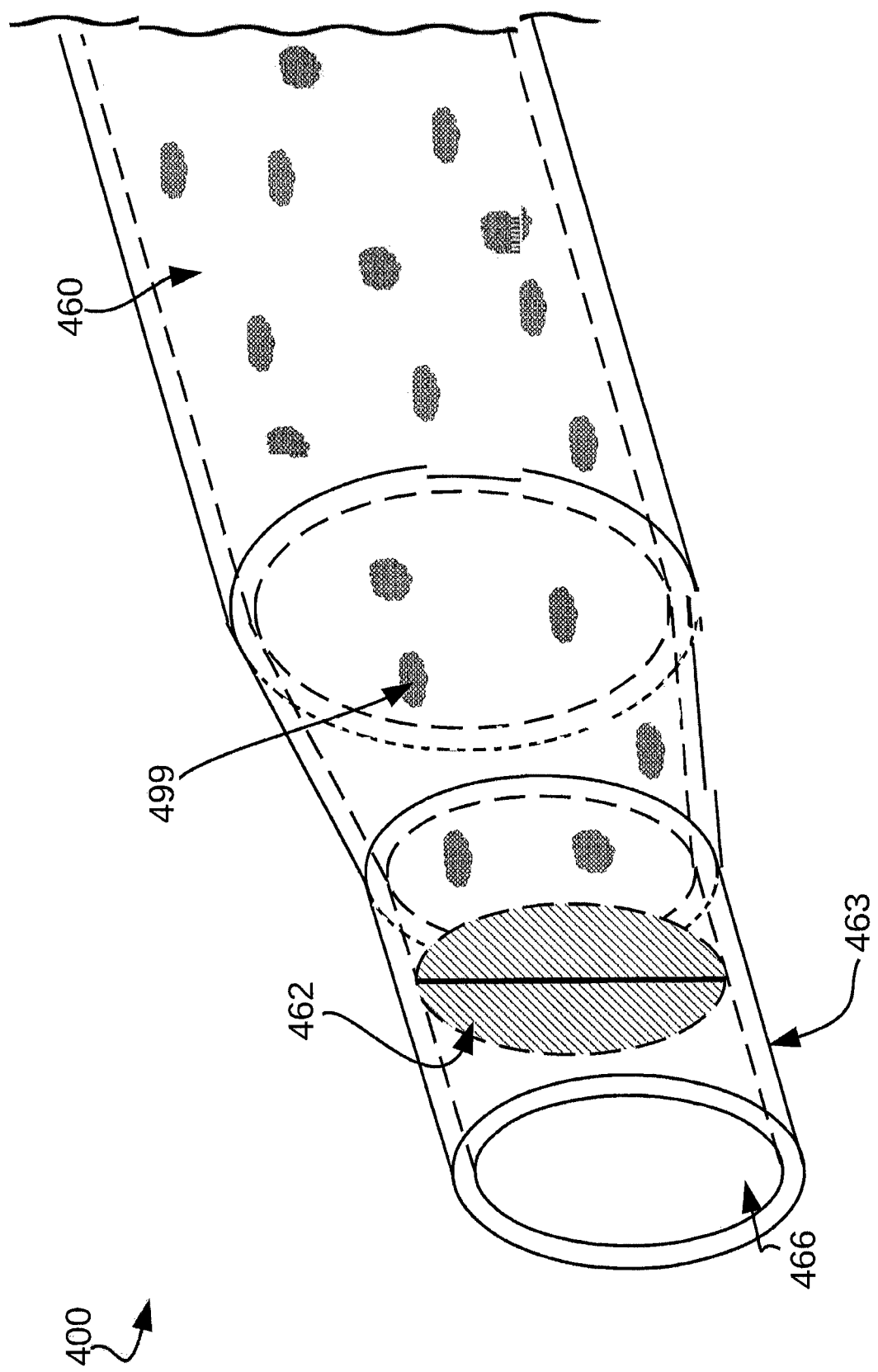
FIG. 4A is a perspective view of a portion of an exemplary delivery device of a type which may be similar to that shown in FIG. 3.
Figure 4B:
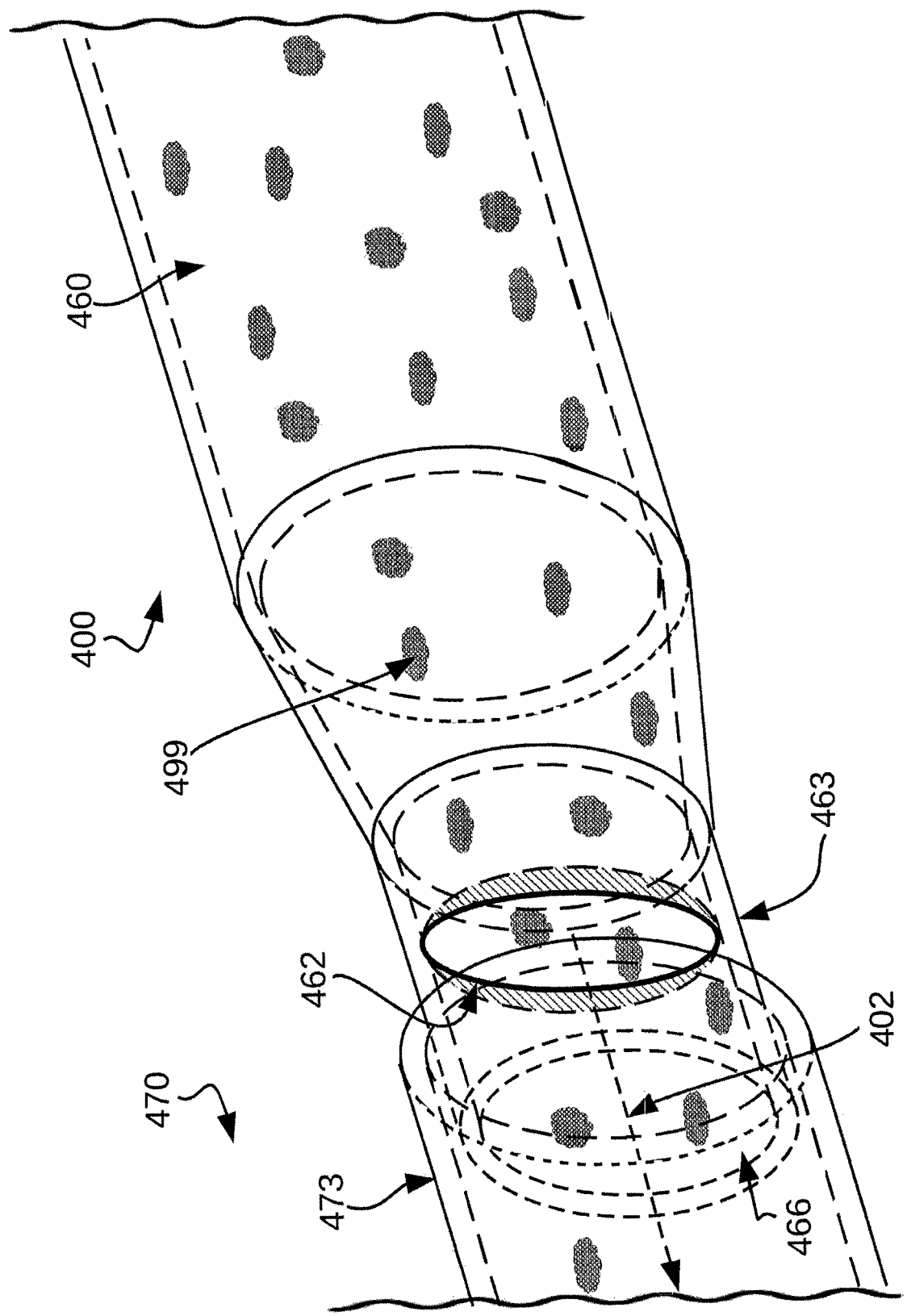
FIG. 4B is a perspective view of a portion of an exemplary delivery device of a particle density" refers to the number of particles or droplets per unit volume of aerosol in cases where at least a portion of the products generated by a device described herein are in the form of a particle or droplet. A density such as "active agent mass density" refers to the mass of active agent per unit volume of all phases (gas, liquid, solid) produced by a single actuation of a device described herein. A density such as "inhalable active agent mass density" refers to the mass of active agent per unit volume of all phases (gas, liquid, solid) produced by a device described herein and delivered into a typical patient tidal volume. A density such as "inhalable product particle density" refers to the product particle density of particles having an average diameter of between about 2.5 to about 4.5 microns produced by a device described herein and delivered into a typical patient tidal volume.

In some optional embodiments, a device described herein can have a closure mechanism, such as, e.g., a one-way valve, as depicted in FIG. 4A and FIG. 4B. An exemplary one-way valve 462 is depicted in a closed configuration in FIG. 4A, which shows a perspective view of a portion of an exemplary embodiment of a delivery device 400 of a type which may be similar to the exemplary device 300 shown in FIG. 3. One-way valve 462 can, for example, be configured to open in a manner that allows only the contents of the device 400, e.g., contents of chamber 460, such as variable products 499 (e.g., variable phase, density, or size), to exit device 400 through distal end aperture 466 on adaptive interface 463, but does not allow backflow of, e.g., air or a user's expiration, into chamber 460 of device 400. In some embodiments, one-way valve 462 can allow contents of chamber 460, e.g., variable products 499, to collect in chamber 460 while valve 462 is in a closed configuration. In some embodiments, valve 462 can allow a user or medical professional to control, via duration of time from actuation of the device to opening of valve 462, dosage, concentration, or product phase, density, or size depending on desired dosing and dosage form (e.g., phase or aerosol or droplet size), depending on the therapeutic used, user disease or condition, method of providing to the user (e.g., ambulatory or mechanically ventilated), desired delivery location within the user's respiratory tract, and the like. In some embodiments, valve 462 can allow a user or medical professional to improve safety on the user's surroundings by preventing user expiration and associated potentially infectious aerosols from entering the device 400 or exiting, for example, a breathing system, during dosing of a therapeutic agent to a user through device 400. In some embodiments, one-way valve 462 can be opened, as depicted in FIG. 4B, by negative pressure generated at distal end aperture 466 on adaptive interface 463, thus allowing products 499 to exit chamber 462 of device 400 in the negative pressure flow direction 462. In some embodiments, negative pressure that opens valve 462 can be generated at aperture 466 by positioning a user's mouth around adaptive interface 463 of the device 400 at the distal end aperture 466 such that the user's lips, together with adaptive interface 463 of the device 400 form a seal, and then inhaling through the user's mouth in a manner similar to the use of an inhaler). In some embodiments, such as in the embodiment depicted in FIG. 4B, which shows a perspective view of a portion of an exemplary delivery device of a type that may be similar to device 300 shown in FIG. 3 and a portion of an exemplary breathing system that may be similar to breathing system 370 shown in FIG. 3, negative pressure that opens valve 462 can be generated at aperture 466 by a breathing system 470 (such as a mechanical ventilation system) via a component of the breathing system, e.g., breathing system adaptive interface 473, attached at adaptive interface 463. Once valve 462 opens, the contents (e.g., gas or products 499) of chamber 460 exit device 400 into the negative pressure source (e.g., a user's mouth and respiratory system, or a user's mechanical breathing system) and create a vacuum or negative pressure within chamber 460, which allows passive filling of chamber 460 by products newly generated by the upstream portion of device 400 (not depicted in FIG. 4A or FIG. 4B). However, one-way valve 462 prevents backflow into device 400 through distal end aperture 466. In some embodiments, a desired product density, product mass density, product particle density, active agent mass density, inhalable active agent mass density, or inhalable product particle density can be delivered to a subject or expelled from the device by controlling the amount of negative pressure applied to the one-way valve (or external pressure applied to first chamber 310 or second chamber 360 to open the one-way valve).

In some alternate embodiments, opening of valve 462 can be controlled by a mechanism within device 400, such as a timed mechanism or programmable mechanism, rather than by negative pressure, to provide for automatic or precision dosage, concentration, product phase, size, or density selection, without requiring a user to actively inhale or without consideration of negative pressure generated by a user or medical device such as breathing system.

Figure 5:
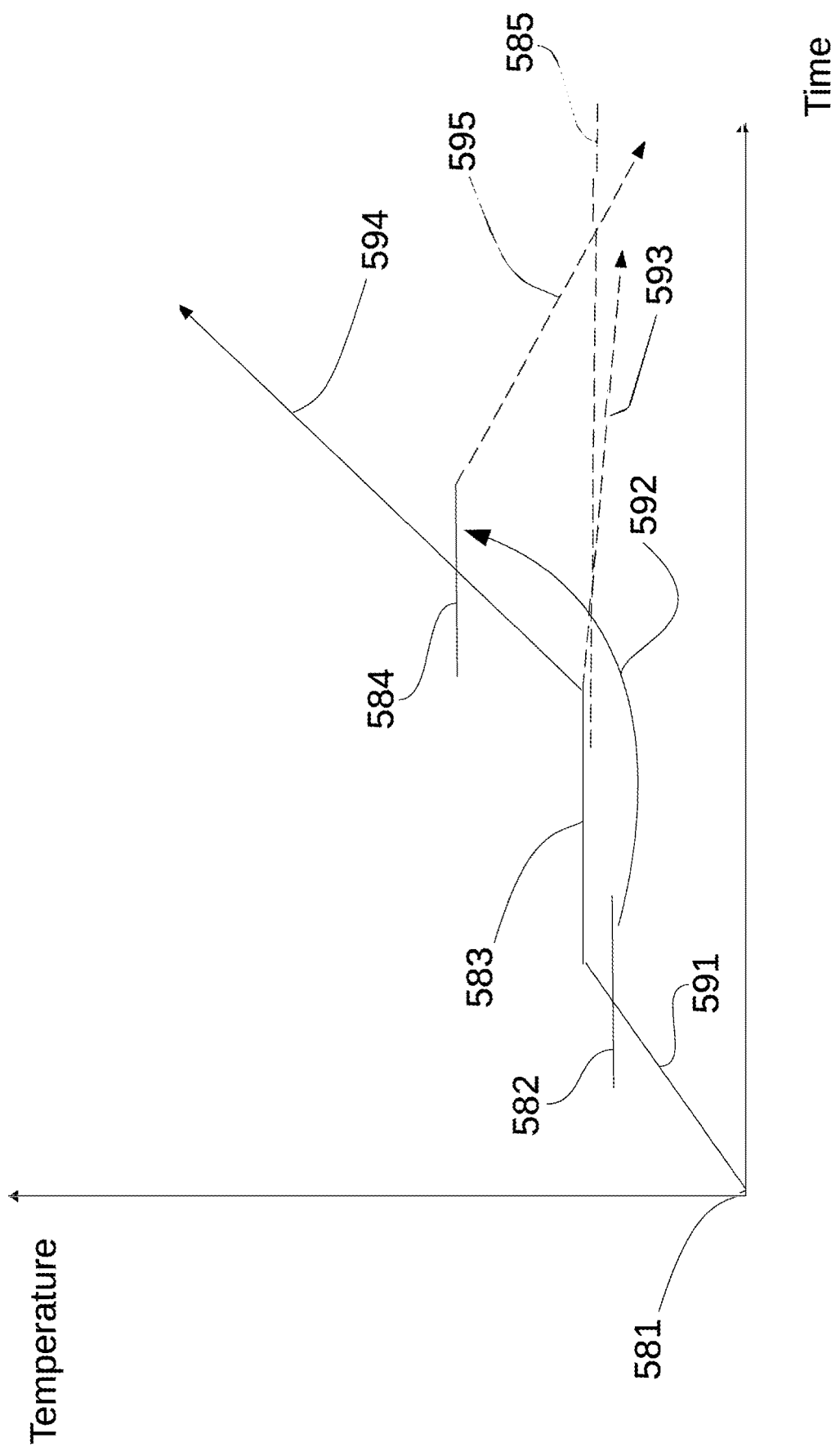

In some embodiments, devices described herein operate by providing control over parameters for heating of a product substrate to provide a desired product to be delivered (e.g., providing variable density, size, or phase of a given product for delivery into a subject). FIG. 5 is a time-temperature graph illustrating exemplary theoretical transformations that an exemplary product substrate can undergo in an exemplary process of producing and delivering variable phase, density, or size products from an exemplary delivery device. In general, the process begins with slow heating of a product substrate upon activation or actuation of the device. The illustrated transformations in the figures provided herein are exemplary possible transformations and do not necessarily occur in all uses of each device described herein. In the process described in FIG. 5, a product substrate is provided with heat at a desired heating rate. In some embodiments, as in this exemplary scenario, the product substrate is provided and present in the device in liquid form. However, in other embodiments, the product substrate can be in a solid form in the device, such as in a powder form, for mixing with a liquid stored elsewhere in the device, or for sublimation directly from a solid, or the like. For example, the product substrate can comprise a two-part substrate, with one part, e.g., a solid such as fine crystals, a dry powder, and the like in a first container, and a liquid solvent portion, such as water, buffer, and the like, in a second container. The containers can be provided in fluid communication within the device such that the two parts can mix and the solid portion can be suspended or dissolved within the solvent portion prior to or during heating of the substrate within the device. As an additional or alternative example, a solid substrate can be provided in a single container for sublimation to vapor phase within the device.

Returning to FIG. 5, in some embodiments, a product substrate can be present as a liquid solution 581 within a delivery device described herein. When the device is activated, one or more heating elements within the device begin to heat at a predetermined heating rate, such as a first heating rate, illustrated by 591. For example, turning to the device described in FIG. 2, the one or more heating plates 221a and 221b, the heating coil 230, or a combination thereof can be activated to begin heating. In some embodiments, the heating element will all begin heating at approximately the same time. In some embodiments, not all heating elements will begin heating at the same time. As an example, in the FIG. 2 device, in one embodiment, heating plate 221b can begin heating first, followed by heating plate 221a, and further followed by heating coil 230. In another exemplary embodiment, heating plates 221a and 221b can begin heating approximately simultaneously, later followed by heating of coil 230. The heating elements slowly heat the product substrate liquid solution 581, as illustrated by 591 in FIG. 5, until the substrate becomes a combination 582 of liquid and gas (vapor phase of the solution) products. In some embodiments, combination 582 is the final product or the device, and can exit the device and be delivered to the subject, depending upon parameters such as, e.g., the heating rate, the dimensions (e.g., length, volume, width or diameter(s)) of first chamber 210, desired end use, and the like. In some embodiments, the combination 582 undergoes further transformation within the device. The device can, in some embodiments, continue to heat substrate combination 582 until all of the liquid phase substrate has vaporized into a gas phase 583. Substrate combination can be heated at the first heating rate, or at a second heating rate (e.g., in some embodiments, as the product substrate becomes substrate combination 582, the expansion of the product substrate moves the substrate combination 582 through the device in the direction of flow, e.g., 202, toward, e.g., a distal portion 219 of first chamber 210, which, in some embodiments, is surrounded by a second heating element, e.g., heating coil 230, which may provide a heating rate, e.g. a second heating rate, that is similar to, the same as, or different from the first heating rate, e.g. the heating rate for heating plates 221a and 221b. In some embodiments, gas phase 583 is the final product or the device, and can exit the device and be delivered to the subject, depending upon parameters such as, e.g., the heating rate, the dimensions (e.g., length, volume, width or diameter(s)) of first chamber 210, optional inclusion of second chamber 260, desired end use, and the like. In some embodiments, the gas phase 583 undergoes further transformation within the device. The device can, in some embodiments, allow passage of the equilibrated gas phase 583 into optional second chamber 260, where cooling and potential condensation can occur, as illustrated by 593, causing, in some embodiments, formation of a mist or heavy mist 585, depending on various parameters, such as whether or not second chamber 260 is adjacent to heating elements or is itself heated, dimensions of second chamber 260, desired end use, and the like. In some embodiments, the device can continue to heat the gas phase 583 to a high temperature steam or vapor 584 (592 illustrates the conversion of early-formed steam or gas phase into a high temperature steam 584 before the equilibration of the remaining liquid or mist portions reaching the vapor phase, as can occur in some embodiments). The device can, in some embodiments, allow passage of the high temperature gas phase 584 into optional second chamber 260, where cooling and potential condensation can occur, as illustrated by 595, causing, in some embodiments, formation of a mist or heavy mist 585, depending on various parameters, such as whether or not second chamber 260 is adjacent to heating elements or is itself heated, dimensions of second chamber 260, desired end use, and the like. In some embodiments, high temperature gas phase 584 is the final product of the device, and can exit the device and be delivered to the subject, depending upon parameters such as, e.g., the heating rate, the dimensions (e.g., length, volume, width or diameter(s)) of first chamber 210, optional inclusion of second chamber 260, desired end use, and the like. In some embodiments, the high temperature steam 584 can continue to be heated further within the device, as illustrated by 594, when needed for a given desired product phase, density, or size, delivery location and the like. High temperature steam or vapor 584 has a temperature above the boiling temperature of the substrate solution. In some embodiments, the high temperature steam or vapor 584 can allow for slower cooling and condensation of the vapor phase upon entry into the optional second chamber or upon entry into a subject, as illustrated by 595, thus allowing the formation of a mist or dense mist or heavy mist within the optional second chamber 260 of the device, or within a subject (e.g., a subject's oral cavity or respiratory system). In some embodiments, the high temperature steam or vapor 584 can form a more dense mist than when mist forms from the cooling of lower temperature steam or vapor. In some embodiments, the high temperature steam or vapor 584 can form a larger particle-size mist than when mist forms from the cooling of lower temperature steam or vapor. In some embodiments, the high temperature steam or vapor can allow for slower cooling and condensation of the vapor phase upon entry into a subject, thus providing a specific desired delivery state, density, or size depending on the subject, desired location delivery within the subject (e.g., upper respiratory, lower respiratory, etc.), and the like. In some embodiments, mists formed from cooling and condensation after formation of the vapor phase or high heat vapor phase can have different characteristics than mists formed before the vapor phase, such as greater density or particle sizes of the mist. Parameters of the device can be adjusted by one skilled in the art according to the desired end use, the particular substrate or therapeutic agent used in the substrate, desired delivery location, and the like. In some embodiments, the slow heating and expansion of the product substrate can generate products such as aerosols, mists, vapors, heavy mists, and combinations thereof, that would not otherwise be easy or possible to generate in other inhalation device methods, such as pressurized inhalers or nebulizers. In some embodiments, the delivery device can generate inhalable products without significant loss or damage to the product substrate or any therapeutic, prophylactic, or diagnostic agent, or other agent contained therein.

In some embodiments, a single delivery device described herein can have a dial, graphical user interface, multiple buttons, or other adjusting means that allows for variable adjustment of the device settings, such as heating rate, timing of initiation of heating of a particular heating element, distance between a heating element and a substrate container or other chamber (e.g., first chamber) within the device, substrate container size, and the like. Such adjustable features can allow for the creation of variable products, such as variable phase, density, or size products, within the same device. In some embodiments, adjustability allows for the creation of variable phase, density, or size products from the same product substrate within a single device, depending on the selected settings. In some embodiments, adjustability allows for the creation of a specific desired phase, density, or size of products, for any given product substrate. For example, a single device having adjustability can generate a heavy mist for each of multiple different substrates (e.g., during different activation periods), even though the substrates can have different boiling points, specific heat capacity, agent damage thresholds (e.g., a high heating rate can, in some embodiments damage molecules within a substrate, whereas a lower heating rate can, in some embodiments, allow heating of a substrate to a higher temperature without significant damage to or loss of the molecules within the substrate), and the like.

Figure 6:
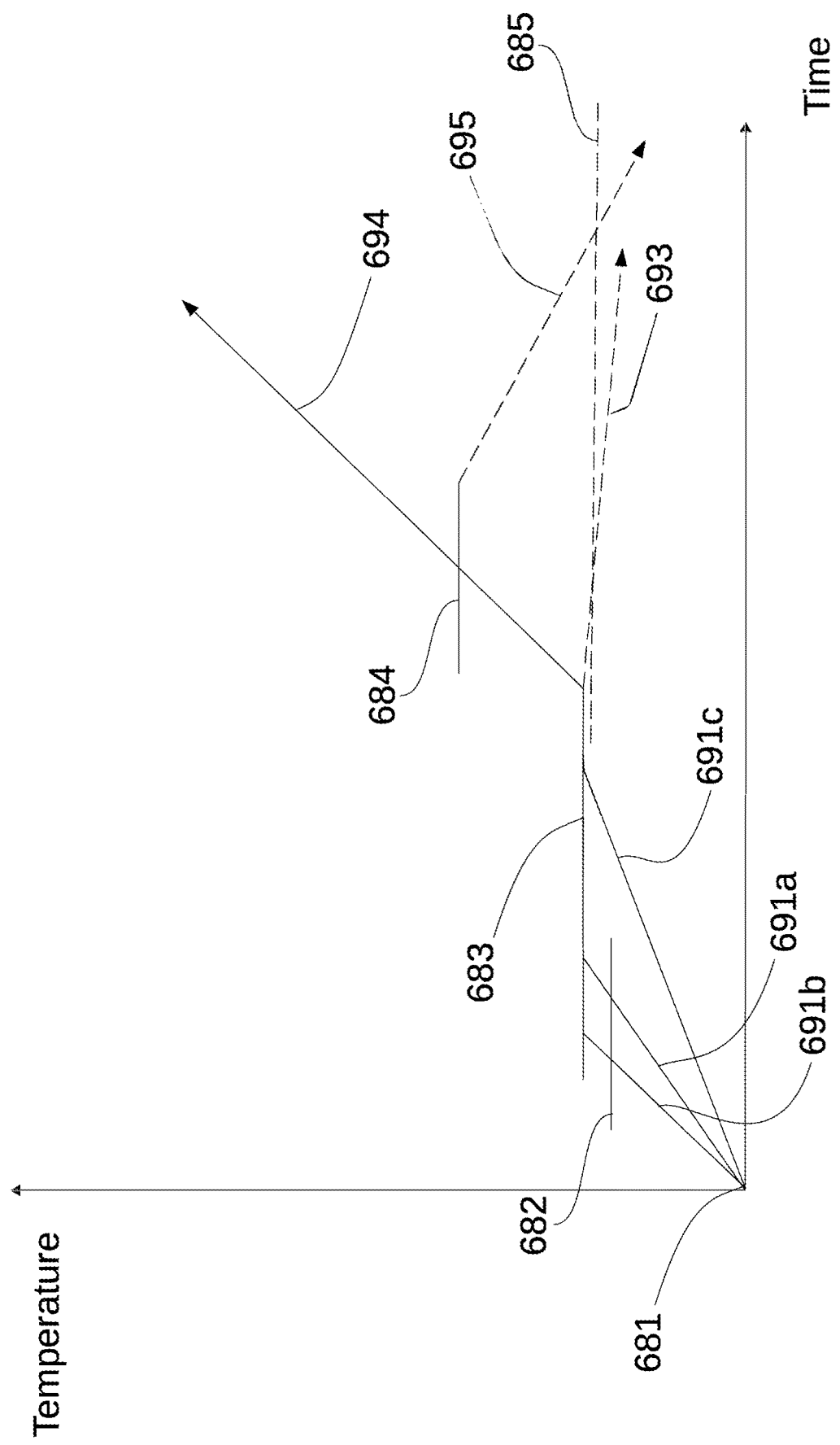

Turning to FIG. 6, a time-temperature graph is shown for a single substrate in an exemplary adjustable device at three different heating rates. The illustrated transformations in the figures provided herein are exemplary possible transformations and do not necessarily occur in all uses of each device described herein. While the same substrate can reach the same phases or transformations (e.g., vapor phase, mist, heavy mist, etc.), depiction of these transformations on the same line or temperature level does not indicate that the products produced by different processes (in the FIG. 6 example, different heating rates), necessarily have all of the same properties or characteristics. In the process described in FIG. 6, a liquid solution product substrate 681 is provided with heat at a first, second, or third heating rate, illustrated by 691*a*, 691*b*, and 691*c*, respectively. For example, turning to the device described in FIG. 2, the one or more heating plates 221*a* and 221*b*, the heating coil 230, or a combination thereof can be activated to begin heating, at heating rate 691*a*, 691*b*, or 691*c*. As can be seen in FIG. 6, the heating rate associated with 691*b* is faster than the heating rates associated with 691*a* and 691*c*, and the heating rate associated with 691*c* is slower than the heating rates associated with 691*a* and 691*b*. The heating elements slowly heat the product substrate liquid solution 681, as illustrated by 691*a*, 691*b*, or 691*c*, until the substrate becomes a combination 682 of liquid and gas (vapor phase of the solution) products or an equilibrated product vapor phase 683. In some embodiments, certain heating rates, e.g., 691*c*, can result in bypass of the mixed liquid/steam state 682, directly to the equilibrated vapor phase 683. While FIG. 6 depicts different heating rates of a single substrate, some advantages of adjustable heating rates include generating different products of a single substrate (e.g., vapor, aerosol, fine aerosol, or heavy mist), and accommodating different types of therapeutic, prophylactic, or diagnostic agents that can each, in some embodiments, require different heating rates. While FIG. 6 depicts different heating rates (e.g., 691*a*, 691*b*, and 691*c*) for a first transformation for simplification, one skilled in the art can readily understand that, in some embodiments, heating rates can differ between adjustable settings for other transformations, such as variable iterations of 694 from the equilibrated vapor phase 683 to the high heat vapor phase 684. Additionally, adjustable cooling rates, such as variable iterations of 693 from the equilibrated vapor phase 683 to the mist or heavy mist products 685, or variable iterations of 695 from the high heat vapor phase 684 to the mist or heavy mist products 685, can also be provided in some embodiments of devices having an optional second chamber.

Inhalation-based therapy and prophylaxis is used for various reasons. For example, the nature of certain conditions such as respiratory infection, respiratory inflammation, or bronchospasm, can make inhalation an optimal route of administration to achieve sufficiently high levels of the drug in affected tissue or tissues. For example, antibiotics can be delivered to the lung tissue of a subject to treat bacterial infections of the lung. As another example, certain agents or products can be applied locally to respiratory tissue to prevent or alleviate symptoms such as bronchial spasm, e.g., in the case of conditions such as asthma or chronic obstructive pulmonary disease (COPD). In some cases, delivery of certain therapeutic, prophylactic, or diagnostic agents by inhalation can produce fewer side effects (e.g., fewer systemic side effects), without limiting effectiveness. In other cases, agents intended for systemic action can be successfully delivered by inhalation, in part because of the large surface area of the lungs, which allows the drug to be rapidly absorbed into systemic circulation without the metabolic effects sometimes associated with oral administration. In some cases, delivery of an agent or product to the lungs or respiratory system of a subject can be more convenient for the subject or the those treating the subject. Additionally, pulmonary delivery has shown promise as a vaccine delivery route for, e.g., routine vaccination.

There are currently three main methods known in the art for delivering agents to a subject's respiratory system. A first method includes aerosolization of an agent dissolved or dispersed in a liquid or gaseous propellant, such as chlorofluorocarbon (CFC) or hydrofluorocarbon (e.g., HFA 134a, HFA 227 and mixtures thereof). These systems are typically used with an inhaler, such as a pressurized metered dose inhaler (pMDI), which dispenses the agent and propellant mixture through a metering valve. With aerosolization inhalers, patients should coordinate their breath with the actuation of the device during administration for optimal delivery of the desired agent. Activation of the inhaler aerosolizes the agent using the propellant. These inhalers can have drawbacks that make them suboptimal for delivering a drug to lung. For example, the propellants can be environmentally hazardous. Additionally, most of a delivered dose of an agent is delivered to a subject's throat or oral cavity rather than lung or respiratory tissue because the aerosolized particles of the agent leave the inhaler at high speeds after actuation due to the pressure created by the propellants. This leads to swallowing a majority of the dosage delivered into the subject rather than delivering it to the desired respiratory tissue. Additionally, because pressurized inhalers require coordination of the subject's breathing with actuation of the device, many patients can have difficulty using pressurized inhalers. For the above reasons, metered-dose inhalers are not optimal for delivering a drug to the lung.

A second method for delivering inhaled agents involves dissolving or dispersing the agent in water, followed by spraying (e.g. creating droplets of) the solution or suspension with a nebulizer (e.g., a compressed air nebulizer or an ultrasonic inhaler). This approach is often preferred for subjects who have difficulty coordinating their breathing with the actuation of a pMDI. Nebulizer delivery has the disadvantage of slow speed. Conventional commercially available nebulizers have delivery rates in the range of about 0.25 to 0.50 ml/min, leading to a drug administration time of 6 to 7 minutes or longer. Nebulizer therapy can be inconvenient and can require a high level of discipline from the user, such as washing and disinfecting after each use. Nebulizers also typically have larger equipment for operating the device and typically require access to a wall outlet. Some nebulizers can contain strainers are only suitable for the delivery of solutions and cannot be used for suspensions due to particle size issues. Therefore, nebulizer usage is generally limited to subjects with difficulty coordinating breathing with device actuation, and subjects with an installed breathing tube.

A third method for delivering agents by inhalation is by inhalation of a dry powder formulation. The agent is delivered to the lungs when the subject inhales the powder from a delivery vehicle located in or on the subject's mouth. Typical dry powder formulations are comprised of carrier particles of an inert ingredient such as lactose mixed with a finely divided pharmaceutically active agent, although some devices are designed to deliver pure, finely divided active agents. For successful delivery of dry powder, the aerodynamic particle size of the drug in the aerosol is usually the most important property.

Aerodynamic size is a characteristic of how drug particles behave in the air stream, and can depend on a number of factors, including geometric particle size, shape, and density. The aerodynamic size can also depend on how easily the particles in the powder can be separated from each other to transition to an aerosol. Thus, small particles that are highly aggregated can behave like much larger particles upon an attempted transition to an aerosol. The aerodynamic size can determine how far particles can penetrate the lung. As a rule, the smaller the particle size, the deeper the particles penetrate the lung. Inhaled particles less than about 1 micron in diameter often do not accumulate in the lung, but exhale back out of a subject's lung. For agents intended for systemic absorption, deep penetration into the alveolar region of the lung is may be desired, and particles with an MMAD of 0.5 to 5 (or 1 to 3) microns are desirable for that purpose. For the treatment of COPD, asthma and other respiratory diseases, the goal can be local delivery to the upper respiratory tract. For this purpose, particles with a size of 3 to 5 μm are generally preferred, since they tend to accumulate in the upper respiratory tract. Most starting agents are significantly larger than 1 to 5 microns in diameter, so for dry powder inhalation formulations, micronization of the agent in an air stream is the typical method. Micronization can be an effective way to reduce the particle size of a drug, but can give particles excess electrostatic charge, which can lead to cohesion of the particles with each other, e.g., with carrier particles in the composition and with the surfaces of dry powder inhalation devices. As a result, the delivery efficiency of conventional dry powder formulations can be relatively low. In some cases of dry powder inhaler therapy, only one third of the aerosol material can reach the patient's airways.

There are several other important parameters for successful delivery of pharmaceutical agents (e.g., therapeutic, prophylactic, or diagnostic agents) through dry powder inhalation, such as aerodynamic diameter of the particles, which is a characteristic of how the particles behave when dispersed in an air stream. Additionally, in cases where an agent composition contains excipients in addition to the particles of the active agent, proper uniformity of the contents of the powder can be important property of the powder for accurate dose delivery. Another important parameter for dry powder inhalation is fluidity of the powder, so that the full appropriate dose of the composition of the powder leaves the device.

Despite advances in methods for preparing dry powder formulations, these devices remain suboptimal in delivering agents as dry powders with suitable properties, such as size, uniformity, and fluidity, to a subject's lung or respiratory tract. Advances in pMDIs and nebulizer technology also fall short of meeting respiratory delivery needs.

The devices described herein provide beneficial alternatives to these previously available methods of generating inhalable products. Instead, the devices described herein use a slow and gentle heating process to generate various different inhalable products, depending on the desired type of inhalable products (e.g., fine aerosol, mist, heavy mist, vapor), desired end use, product substrate used, desired delivery location within a subject, concerns about generation of infectious particles, and the like. In some embodiments, the devices can be designed or tuned to generate specific inhalable products, including aerosols, mists or heavy mists (e.g., mist or heavy mist aersosols), gas phase vapor, and combinations thereof.

In some embodiments, unlike typical known inhalation techniques, the devices described herein can generate and deliver to a desired location within a subject inhalable products without excessive loss of agent prior to delivery to the desired location. The devices described herein can, in some embodiments, generate inhalable products from agents that generally cannot undergo typical aerosolization techniques without substantial loss. In some embodiments, devices described herein can generate inhalable products from a product substrate with a loss in the active agent of the product substrate of less than about 1%, about 2%, about 3%, about 4%, about 5%, about 6%, about 7%, about 8%, about 9%, about 10%, about 15%, about 20% about 25%, about 30%, about 35%, about 40%, about 45%, or about 50%.

In some embodiments, the devices described herein utilize slow or gentle heating of a product substrate to generate variable density, phase, or size inhalable products. In some embodiments, the heating rate describes a rate at which a heating implement or element within the device is heated. For example, in some embodiments, the heating rate describes the rate at which a heating plate (for example, heating plates 121a and 121b in FIG. 1) is heated. In some embodiments, the heating rate describes the rate at which a heating coil (for example, heating coil 130 in FIG. 1) is heated. In some embodiments, the heating rate describes the rate at which a combination of heating elements within a device is heated (for example, a combination of heating coil 130 and heating plates 121a and 121b in FIG. 1). In some embodiments, a heating rate described a rate at which a vessel or chamber within a device increases in temperature during operation of a device. For example, in some embodiments, a heating rate describes the rate of increase in temperature of container 340, first chamber 310, or a combination thereof in FIG. 3.

In some embodiments, the heating rate, e.g., a first heating rate or a second heating rate, can be from 0.001° C./min to 150° C./min, from 0.1° C./min to 50° C./min, from 1° C./min to 80° C./min, or it can be any rate from 1° C./min to 150° C./min in 1° C. intervals. In some embodiments, the heating rate can be from about 50° C./min to about 150° C./min, from about 50° C./min to about 60° C./min, from about 50° C./min to about 70° C./min, from about 50° C./min to about 80° C./min, from about 50° C./min to about 90° C./min, from about 50° C./min to about 100° C./min, from about 50° C./min to about 110° C./min, from about 50° C./min to about 120° C./min, from about 50° C./min to about 130° C./min, from about 50° C./min to about 140° C./min, from about 60° C./min to about 70° C./min, from about 60° C./min to about 80° C./min, from about 60° C./min to about 90° C./min, from about 60° C./min to about 100° C./min, from about 60° C./min to about 110° C./min, from about 60° C./min to about 120° C./min, from about 60° C./min to about 130° C./min, from about 60° C./min to about 140° C./min, from about 70° C./min to about 80° C./min, from about 70° C./min to about 90° C./min, from about 70° C./min to about 100° C./min, from about 70° C./min to about 110° C./min, from about 70° C./min to about 120° C./min, from about 70° C./min to about 130° C./min, from about 70° C./min to about 140° C./min, from about 80° C./min to about 90° C./min, from about 80° C./min to about 100° C./min, from about 80° C./min to about 110° C./min, from about 80° C./min to about 120° C./min, from about 80° C./min to about 130° C./min, from about 80° C./min to about 140° C./min, from about 90° C./min to about 100° C./min, from about 90° C./min to about 110° C./min, from about 90° C./min to about 120° C./min, from about 90° C./min to about 130° C./min, from about 90° C./min to about 140° C./min, from about 100° C./min to about 110° C./min, from about 100° C./min to about 120° C./min, from about 100° C./min to about 130° C./min, from about 100° C./min to about 140° C./min, from about 110° C./min to about 120° C./min, from about 110° C./min to about 130° C./min, from about 110° C./min to about 140° C./min, from about 120° C./min to about 130° C./min, from about 120° C./min to about 140° C./min, from about 130° C./min to about 140° C./min, from about 140° C./min to about 150° C./min, about 50° C./min, about 55° C./min, about 60° C./min, about 65° C./min, about 70° C./min, about 71° C./min, about 72° C./min, about 73° C./min, about 74° C./min, about 75° C./min, about 76° C./min, about 77° C./min, about 78° C./min, about 79° C./min, about 80° C./min, about 81° C./min, about 82° C./min, about 83° C./min, about 84° C./min, about 85° C./min, about 86° C./min, about 87° C./min, about 88° C./min, about 89° C./min, about 90° C./min, about 91° C./min, about 92° C./min, about 93° C./min, about 94° C./min, about 95° C./min, about 96° C./min, about 97° C./min, about 98° C./min, about 99° C./min, about 100° C./min, about 101° C./min, about 102° C./min, about 103° C./min, about 104° C./min, about 105° C./min, about 106° C./min, about 107° C./min, about 108° C./min, about 109° C./min, about 110° C./min, about 115° C./min, about 120° C./min, about 125° C./min, about 130° C./min, about 135° C./min, about 140° C./min, about 145° C./min, or about 150° C./min.

In some embodiments, the heating rate can be from about 0.1° C./sec to about 10° C./sec, from about 0.2° C./sec to about 10° C./sec, from about 0.3° C./sec to about 10° C./sec, from about 0.4° C./sec to about 10° C./sec, from about 0.5° C./sec to about 10° C./sec, from about 0.6° C./sec to about 10° C./sec, from about 0.7° C./sec to about 10° C./sec, from about 0.8° C./sec to about 10° C./sec, from about 0.9° C./sec to about 10° C./sec, from about 1° C./sec to about 10° C./sec, from about 1° C./sec to about 1.5° C./sec, from about 1° C./sec to about 2° C./sec, from about 1° C./sec to about 3° C./sec, from about 1° C./sec to about 4° C./sec, from about 1° C./sec to about 5° C./sec, from about 1° C./sec to about 2.5° C./sec, from about 1° C./sec to about 3.5° C./sec, from about 1° C./sec to about 4.5° C./sec, from about 1° C./sec to about 6° C./sec, from about 1° C./sec to about 6.5° C./sec, from about 1° C./sec to about 7.5° C./sec, from about 1° C./sec to about 7° C./sec, from about 1° C./sec to about 8° C./sec, from about 1° C./sec to about 8.5° C./sec, from about 1° C./sec to about 9° C./sec, from about 1° C./sec to about 9.5° C./sec, from about 1° C./sec to about ° C./sec, from about 2° C./sec to about 5° C./sec, from about 3° C./sec to about 5° C./sec, or from about 4° C./sec to about 5° C./sec.

In some embodiments, the devices described herein are designed to heat to a specified temperature. For example, in some embodiments, the devices described herein are designed to heat a heating plate or a heating coil or a heating chamber to from about 60° C. to about 120° C., from about 70° C. to about 110° C., from about 75° C. to about 105° C., from about 80° C. to about 110° C., from about 75° C. to about 110° C., from about 80° C. to about 105° C., from about 85° C. to about 110° C., from about 85° C. to about 105° C., from about 75° C. to about 101° C., from about 80° C. to about 101° C., from about 85° C. to about 101° C., from about 90° C. to about 110° C., from about 90° C. to about 105° C., from about 90° C. to about 101° C., from about 95° C. to about 110° C., from about 95° C. to about 105° C., from about 95° C. to about 101° C., from about 95° C. to about 100° C., from about 96° C. to about 110° C., from about 96° C. to about 105° C., from about 96° C. to about 101° C., from about 96° C. to about 100° C., from about 97° C. to about 110° C., from about 97° C. to about 105° C., from about 97° C. to about 101° C., from about 97° C. to about 100° C., from about 98° C. to about 110° C., from about 98° C. to about 105° C., from about 98° C. to about 101° C., from about 98° C. to about 100° C., from about 99° C. to about 110° C., from about 99° C. to about 105° C., from about 99° C. to about 101° C., or from about 99° C. to about 100° C. In some embodiments, the devices described herein are designed to maintain the temperature of a heating plate, a heating coil, or a heating chamber at the specified temperature for from about 1 sec to about 5 min, from about 1 sec to about 4 min, from about 1 sec to about 3 min, from about 1 sec to about 2 min, from about 1 sec to about 1 min, from about 5 sec to about 5 min, from about 5 sec to about 4 min, from about 5 sec to about 3 min, from about 5 sec to about 2 min, from about 5 sec to about 1 min, from about 10 sec to about 5 min, from about 10 sec to about 4 min, from about 10 sec to about 3 min, from about 10 sec to about 2 min, from about 10 sec to about 1 min, from about 15 sec to about 5 min, from about 15 sec to about 4 min, from about 15 sec to about 3 min, from about 15 sec to about 2 min, from about 15 sec to about 1 min, from about 20 sec to about 5 min, from about 20 sec to about 4 min, from about 20 sec to about 3 min, from about 20 sec to about 2 min, from about 20 sec to about 1 min, from about 30 sec to about 5 min, from about 30 sec to about 4 min, from about 30 sec to about 3 min, from about 30 sec to about 2 min, or from about 30 sec to about 1 min.

In some embodiments, the devices described herein generate variable density, phase, or size inhalable products. In some embodiments, the products can be in a solid or liquid phase, such as part of an aerosol or mist. In some embodiments, the products can be in a gaseous or vapor phase. In some embodiments, the products generated by the devices described herein can comprise fine aerosol (1-3.5 microns) or ultra fine aerosol (10-100 nm) particles. In some embodiments, the products generated by the devices described herein can comprise mist (e.g., droplets of liquid having a particle size of from 2.5-4.5 microns suspended or dispersed in a gas). In some embodiments, the products generated by the devices described herein can comprise heavy mist (e.g., droplets of liquid having a particle size of from 3.5 to 50 micron suspended or dispersed in a gas). In some embodiments, the products generated by the devices described herein can comprise vapor phase solutions. In some embodiments, the products can be a mixture of two or more phases (e.g., liquid droplets and vapor), two or more particle sizes, and the like. In some embodiments, the products generated by the devices described herein can be solid or liquid particles ranging in size from about 1 to about 10 microns, from about 1 to about 8 microns, from about 1 to about 5 microns, from about 1 to about 4.5 microns, from about 2 to about 10 microns, from about 2 to about 8 microns, from about 2 to about 5 micron, from about 2 to about 4.5 microns, from about 2.5 to about 10 microns, from about 2.5 to about 8 microns, from about 2.5 to about 5 microns, from about 2.5 to about 4.5 microns, from about 3 to about 10 microns, from about 3 to about 8 microns, from about 3 to about 5 microns, from about 3 to about 4.5 microns, 3.5 to about 10 microns, from about 3.5 to about 8 microns, from about 3.5 to about 5 microns, from about 3.5 to about 4.5 microns, 4 to about 10 microns, from about 4 to about 8 microns, from about 4 to about 5 microns, from about 4 to about 4.5 microns, from about 2.5 to about 4.25 microns, from about 2.5 to about 4 microns, from about 2.5 to about 3.75 microns, from about 2.5 to about 3.5 microns, from about 2.5 to about 3.25 microns, from about 2.5 to about 3 microns, from about 2.5 to about 2.75 microns, from about 2.75 to about 4.25 microns, from about 2.75 to about 4 microns, from about 2.75 to about 3.75 microns, from about 2.75 to about 3.5 microns, from about 2.75 to about 3.25 microns, from about 2.75 to about 3 microns, 3 to about 4.25 microns, from about 3 to about 4 microns, from about 3 to about 3.75 microns, from about 3 to about 3.5 microns, from about 3 to about 3.25 microns, 3.25 to about 4.25 microns, from about 3.25 to about 4 microns, from about 3.25 to about 3.75 microns, from about 3.25 to about 3.5 microns, from about 3.5 to about 4.25 microns, from about 3.5 to about 4 microns, from about 3.5 to about 53.75 microns, from about 3.75 to about 4.5 microns, from about 3.75 to about 4.25 microns, or from about 3.75 to about 4 microns.

In some embodiments, the density of the individual particles, products, or droplets generated by a device can be tunable based on selected operation parameters on a given embodiment of the devices described herein. For example, in some embodiments, a desired fraction of the total particles, products, or droplets generated by a device (e.g., in some embodiments, a fraction of at least 10%, 20%, at least 30%, at least 40%, at least 50%, at least 60%, at least 70%, at least 80%, at least 90%, or more than 90% of the total particles, products, or droplets generated by a device) can be provided at a desired density. For example, in some embodiments, the generated products can have a product density describing the average density of the described fraction (e.g., at least 50%, at least 60%, at least 80%, etc.) of the products (e.g., particle or droplet) generated by a device having an average diameter of from about 2.5 to about 4.5 microns. In some embodiments of the devices described herein, at least 50%, at least 60%, at least 70%, at least 80%, at least 85%, at least 90%, or at least 95% or the products generated by the device have an average diameter of from about 2.5 microns to about 4.5 microns with a particle density or droplet density of at least $10^4$ particles or droplets per mL, at least $10^6$ particles or droplets per mL, at least $10^8$ particles or droplets per mL, at least $10^{10}$ particles or droplets per mL, or from about $10^4$ particles or droplets per mL to about $10^{12}$ particles or droplets (having an average diameter of from about 2.5 microns to about 4.5 micron) per mL (e.g., from about $10^4$ particles or droplets per mL to about $10^{11}$ particles or droplets per mL, from about $10^4$ particles or droplets per mL to about $10^{10}$ particles or droplets per mL, from about $10^4$ particles or droplets per mL to about $10^9$ particles or droplets per mL, from about $10^4$ particles or droplets per mL to about $10^8$ particles or droplets per mL, from about $10^4$ particles or droplets per mL to about $10^7$ particles or droplets per mL, from about $10^4$ particles or droplets per mL to about $10^6$ particles or droplets per mL, from about $10^4$ particles or droplets per mL to about $10^5$ particles or droplets per mL, from about $10^5$ particles or droplets per mL to about $10^{12}$ particles or droplets per mL, from about $10^5$ particles or droplets per mL to about $10^{11}$ particles or droplets per mL, from about $10^5$ particles or droplets per mL to about $10^{10}$ particles or droplets per mL, from about $10^5$ particles or droplets per mL to about $10^9$ particles or droplets per mL, from about $10^5$ particles or droplets per mL to about $10^8$ particles or droplets per mL, from about $10^5$ particles or droplets per mL to about $10^7$ particles or droplets per mL, from about $10^5$ particles or droplets per mL to about $10^6$ particles or droplets per mL, from about $10^6$ particles or droplets per mL to about $10^{12}$ particles or droplets per mL, from about $10^6$ particles or droplets per mL to about $10^{11}$ particles or droplets per mL, from about $10^6$ particles or droplets per mL to about $10^{10}$ particles or droplets per mL, from about $10^6$ particles or droplets per mL to about $10^9$ particles or droplets per mL, from about $10^6$ particles or droplets per mL to about $10^8$ particles or droplets per mL, from about $10^6$ particles or droplets per mL to about $10^7$ particles or droplets per mL, from about $10^7$ particles or droplets per mL to about $10^{12}$ particles or droplets per mL, from about $10^7$ particles or droplets per mL to about $10^{11}$ particles or droplets per mL, from about $10^7$ particles or droplets per mL to about $10^{10}$ particles or droplets per mL, from about $10^7$ particles or droplets per mL to about $10^9$ particles or droplets per mL, from about $10^7$ particles or droplets per mL to about $10^8$ particles or droplets per mL, from about $10^8$ particles or droplets per mL to about $10^{12}$ particles or droplets per mL, from about $10^8$ particles or droplets per mL to about $10^{11}$ particles or droplets per mL, from about $10^8$ particles or droplets per mL to about $10^{10}$ particles or droplets per mL, from about $10^8$ particles or droplets per mL to about $10^9$ particles or droplets per mL, from about $10^9$ particles or droplets per mL to about $10^{12}$ particles or droplets per mL, from about $10^9$ particles or droplets per mL to about $10^{11}$ particles or droplets per mL, from about $10^9$ particles or droplets per mL to about $10^{10}$ particles or droplets per mL, from about $10^{10}$ particles or droplets per mL to about $10^{12}$ particles or droplets per mL, from about $10^{10}$ particles or droplets per mL to about $10^{11}$ particles or droplets per mL, or from about $10^{11}$ particles or droplets per mL to about $10^{12}$ particles or droplets per mL).

In some embodiments, the generated products can have an inhalable product particle density of at least $10^4$ particles or droplets per mL, at least $10^6$ particles or droplets per mL, at least $10^8$ particles or droplets per mL, at least $10^{10}$ particles or droplets per mL, or from about $10^4$ particles or droplets per mL to about $10^{12}$ particles or droplets (having an average diameter of from about 2.5 microns to about 4.5 micron) per mL (e.g., from about $10^4$ particles or droplets per mL to about $10^{11}$ particles or droplets per mL, from about $10^4$ particles or droplets per mL to about $10^{10}$ particles or droplets per mL, from about $10^4$ particles or droplets per mL to about $10^9$ particles or droplets per mL, from about $10^4$ particles or droplets per mL to about $10^8$ particles or droplets per mL, from about $10^4$ particles or droplets per mL to about $10^7$ particles or droplets per mL, from about $10^4$ particles or droplets per mL to about $10^6$ particles or droplets per mL, from about $10^4$ particles or droplets per mL to about $10^5$ particles or droplets per mL, from about $10^5$ particles or droplets per mL to about $10^{12}$ particles or droplets per mL, from about $10^5$ particles or droplets per mL to about $10^{11}$ particles or droplets per mL, from about $10^5$ particles or droplets per mL to about $10^{10}$ particles or droplets per mL, from about $10^5$ particles or droplets per mL to about $10^9$ particles or droplets per mL, from about $10^5$ particles or droplets per mL to about $10^8$ particles or droplets per mL, from about $10^5$ particles or droplets per mL to about $10^7$ particles or droplets per mL, from about $10^5$ particles or droplets per mL to about $10^6$ particles or droplets per mL, from about $10^6$ particles or droplets per mL to about $10^{12}$ particles or droplets per mL, from about $10^6$ particles or droplets per mL to about $10^{11}$ particles or droplets per mL, from about $10^6$ particles or droplets per mL to about $10^{10}$ particles or droplets per mL, from about $10^6$ particles or droplets per mL to about $10^9$ particles or droplets per mL, from about $10^6$ particles or droplets per mL to about $10^8$ particles or droplets per mL, from about $10^6$ particles or droplets per mL to about $10^7$ particles or droplets per mL, from about $10^7$ particles or droplets per mL to about $10^{12}$ particles or droplets per mL, from about $10^7$ particles or droplets per mL to about $10^{11}$ particles or droplets per mL, from about $10^7$ particles or droplets per mL to about $10^{10}$ particles or droplets per mL, from about $10^7$ particles or droplets per mL to about $10^9$ particles or droplets per mL, from about $10^7$ particles or droplets per mL to about $10^8$ particles or droplets per mL, from about $10^8$ particles or droplets per mL to about $10^{12}$ particles or droplets per mL, from about $10^8$ particles or droplets per mL to about $10^{11}$ particles or droplets per mL, from about $10^8$ particles or droplets per mL to about $10^{10}$ particles or droplets per mL, from about $10^8$ particles or droplets per mL to about $10^9$ particles or droplets per mL, from about $10^9$ particles or droplets per mL to about $10^{12}$ particles or droplets per mL, from about $10^9$ particles or droplets per mL to about $10^{11}$ particles or droplets per mL, from about $10^9$ particles or droplets per mL to about $10^{10}$ particles or droplets per mL, from about $10^{10}$ particles or droplets per mL to about $10^{12}$ particles or droplets per mL, from about $10^{10}$ particles or droplets per mL to about $10^{11}$ particles or droplets per mL, or from about $10^{11}$ particles or droplets per mL to about $10^{12}$ particles or droplets per mL).

In some embodiments, the generated products can have a product mass density of from about 0.1 mg/L to about 100 mg/L.

In some embodiments, the generated products can have an active agent mass density of from about 0.1 mg/L to about 50 mg/L, from about 0.5 mg/L to about 40 mg/L, from about 0.5 mg/L to about 30 mg/L, from about 0.5 mg/L to about 20 mg/L, from about 0.5 mg/L to about 15 mg/L, from about 0.5 mg/L to about 10 mg/L, from about 1 mg/L to about 20 mg/L, from about 1 mg/L to about 18 mg/L, from about 1 mg/L to about 15 mg/L, from about 1 mg/L to about 14 mg/L, from about 1 mg/L to about 13 mg/L, from about 1 mg/L to about 12 mg/L, from about 1 mg/L to about 11 mg/L, from about 1 mg/L to about 10 mg/L, from about 1 mg/L to about 9 mg/L, from about 1 mg/L to about 8 mg/L, from about 1 mg/L to about 7 mg/L, from about 1 mg/L to about 6 mg/L, from about 1 mg/L to about 5 mg/L, from about 1 mg/L to about 4 mg/L, from about 1 mg/L to about 3 mg/L, from about 1 mg/L to about 2 mg/L, from about 1 mg/L to about 1.5 mg/L, from about 1.5 mg/L to about 10 mg/L, from about 2 mg/L to about 10 mg/L, from about 2.5 mg/L to about 10 mg/L, from about 3 mg/L to about 10 mg/L, from about 3.5 mg/L to about 10 mg/L, from about 4 mg/L to about 10 mg/L, from about 4.5 mg/L to about 10 mg/L, from about 5 mg/L to about 10 mg/L, from about 5.5 mg/L to about 10 mg/L, from about 6 mg/L to about 10 mg/L, from about 6.5 mg/L to about 10 mg/L, from about 7 mg/L to about 10 mg/L, from about 7.5 mg/L to about 10 mg/L, from about 8 mg/L to about 10 mg/L, from about 8.5 mg/L to about 10 mg/L, from about 1.2 mg/L to about 5 mg/L, from about 1.5 mg/L to about 5 mg/L, from about 2 mg/L to about 5 mg/L, from about 2.5 mg/L to about 5 mg/L, from about 3 mg/L to about 5 mg/L, from about 3.5 mg/L to about 5 mg/L, from about 4 mg/L to about 5 mg/L, or from about 4.5 mg/L to about 5 mg/L.

In some embodiments, the generated products can have an inhalable active agent mass density of from about 0.1 mg/L to about 50 mg/L, of from about 0.2 mg/L to about 50 mg/L, from about 0.5 mg/L to about 40 mg/L, from about 0.5 mg/L to about 30 mg/L, from about 0.5 mg/L to about 20 mg/L, from about 0.5 mg/L to about 15 mg/L, from about 0.5 mg/L to about 10 mg/L, from about 1 mg/L to about 20 mg/L, from about 1 mg/L to about 18 mg/L, from about 1 mg/L to about 15 mg/L, from about 1 mg/L to about 14 mg/L, from about 1 mg/L to about 13 mg/L, from about 1 mg/L to about 12 mg/L, from about 1 mg/L to about 11 mg/L, from about 1 mg/L to about 10 mg/L, from about 1 mg/L to about 9 mg/L, from about 1 mg/L to about 8 mg/L, from about 1 mg/L to about 7 mg/L, from about 1 mg/L to about 6 mg/L, from about 1 mg/L to about 5 mg/L, from about 1 mg/L to about 4 mg/L, from about 1 mg/L to about 3 mg/L, from about 1 mg/L to about 2 mg/L, from about 1 mg/L to about 1.5 mg/L, from about 1.5 mg/L to about 10 mg/L, from about 2 mg/L to about 10 mg/L, from about 2.5 mg/L to about 10 mg/L, from about 3 mg/L to about 10 mg/L, from about 3.5 mg/L to about 10 mg/L, from about 4 mg/L to about 10 mg/L, from about 4.5 mg/L to about 10 mg/L, from about 5 mg/L to about 10 mg/L, from about 5.5 mg/L to about 10 mg/L, from about 6 mg/L to about 10 mg/L, from about 6.5 mg/L to about 10 mg/L, from about 7 mg/L to about 10 mg/L, from about 7.5 mg/L to about 10 mg/L, from about 8 mg/L to about 10 mg/L, from about 8.5 mg/L to about 10 mg/L, from about 1.2 mg/L to about 5 mg/L, from about 1.5 mg/L to about 5 mg/L, from about 2 mg/L to about 5 mg/L, from about 2.5 mg/L to about 5 mg/L, from about 3 mg/L to about 5 mg/L, from about 3.5 mg/L to about 5 mg/L, from about 4 mg/L to about 5 mg/L, or from about 4.5 mg/L to about 5 mg/L.

In some embodiments, the product substrate comprises at least 10% by weight of one or more active agents. In some embodiments, at least 20%, 30%, 40%, 50%, 60%, 70%, 80%, 90%, 95%, 97%, 99%, 99.5%, 99.9% or 99.97% by weight of one or more active agents.

In some embodiments, the generated products are formed, following activation of a device described herein, at a rate greater than 0.5 mg/sec, greater than 0.75 mg/sec, greater than 1 mg/second, greater than 1.5 mg/second or greater than 2 mg/second. In some embodiments, the rate of inhalable product particle formation of the generated products, following activation of a device described herein, is greater than $10^4$ particles/second, greater than $10^6$ particles/second, greater than $10^8$ particles/second, greater than $10^9$ particles/second, or greater than $10^{10}$ particles/second. In some embodiments, a single inhalable dose of generated products is generated in less than about 5 minutes from actuation of a device described herein, less than about 4 minutes from actuation, less than about 3 minutes from actuation, less than about 2 minutes from actuation, less than about 90 seconds from actuation, less than about 75 seconds from actuation, less than about 60 seconds from actuation, less than about 45 seconds from actuation, less than about 30 seconds from actuation, less than about 15 seconds from actuation, or less than about 10 seconds from actuation. In some embodiments, a single inhalable dose of generated products is generated in from about 1 second to about 4 minutes from actuation of a device described herein, from about 1 second to about 3 minutes from actuation, from about 1 second to about 2 minutes from actuation, from about 10 seconds to about 4 minutes from actuation, from about 10 seconds to about 3 minutes from actuation, from about 10 seconds to about 2 minutes from actuation, from about 20 seconds to about 4 minutes from actuation, from about 20 seconds to about 3 minutes from actuation, from about 20 seconds to about 2 minutes from actuation, from about 30 seconds to about 4 minutes from actuation, from about 30 seconds to about 3 minutes from actuation, or from about 30 seconds to about 2 minutes from actuation. The rate of inhalable product particle formation can be determined, for example, by delivering a sample of generated products into a restricted chamber via device described herein over a set time period (e.g. 10 seconds, 1 min, etc.) and the number of particles of a given size collected in the chamber is determined as per known methods in the art. The rate of particle formation is equal to the number of collected inhalable product particles divided by the set collection time. Delivery time of a desired dose can be determined similarly. For example, generated products can be collected in a restricted chamber until the desired product mass is achieved, and the time for collection of the desired mass can be measured.

In some embodiments, inhalers are provided herein, comprising a delivery device as described herein for generating variable density, phase, or size products. For example, standard inhaler housings can be used, and the devices described herein for generating variable density, phase, or size products can be placed within the standard inhaler housing. In some embodiments, the inhaler can be an inhaler used for delivering an inhalable composition or inhalable products to an ambulatory subject that does not require mechanical breathing assistance. In some embodiments, the inhaler can be an inhaler used for delivering an inhalable composition to a subject that requires mechanical breathing assistance, including non-ambulatory subjects. For example, the inhaler can, in some embodiments, be an inhaler that can be operably connected to a breathing system that includes a pressure-assisted breathing device. In some embodiments, a breathing system can include an inhaler comprising an inhalable composition comprising amniotic fluid or an amnion tissue preparation.

In some embodiments, exemplary inhalation devices can include a unit dose inhaler or a multiple dose inhaler. As used herein a "unit dose" refers to a pre-metered formulation (e.g., a substrate) for inhalation. In some embodiments, a unit dose can be a single container having multiple doses of formulation that can be delivered by inhalation as metered single amounts, provided that the contained allows for heating of only the single dose in use at any given time. A unit dose cartridge/container can contain a single dose. In some embodiments, it can include multiple individually accessible compartments, each containing a unit dose. The term "unit dose inhaler" refers to an inhaler that delivers a single dose of a composition or formulation by inhalation to a subject user. Typically, a unit dose inhaler contains a single container that holds or contains an inhalable formulation. Thus, in some embodiments, an inhalation device described herein can contain, or have a receiving portion for, a single vessel for a single unit dose. The vessel can be refillable or rechargeable through an access port (such as an access aperture in the sidewall of the device, to be refilled by insertion of a liquid substrate-filled syringe. In some embodiments, the vessel can be removable or replaceable such that when empty, the vessel can be replaced with another vessel containing a single unit dose of product substrate.

It will be appreciated that in some cases, multiple unit doses are required to provide a user with a specified dosage or treatment protocol. In such cases, embodiments such as the refillable or replaceable-vessel unit dose inhalation devices can be utilized. Alternatively, in another embodiments, a device described herein can be a multiple dose inhaler. The term "multiple dose inhaler" refers to an inhaler having two or more containers, each container comprising a pre-metered dose of an inhalable composition (e.g., substrate), and the inhaler delivers a single dose of the inhalable composition by inhalation at any one time. In one exemplary embodiment, an inhalation device described herein can be configured to contain multiple vessels containing substrate, each vessel containing a unit dose. A means for cycling the vessels through a heating region to deliver each dose can be used to create an inhalation device that carries multiple unit doses, provided that the vessels of substrate not in use at a given time are insulated from the region providing heat the substrate vessel in use.

In some embodiments, the inhaler comprising a delivery device as described herein for generating variable density, phase, or size products can comprise any of the medicaments or product substrate compositions described herein. In some embodiments, an inhaler comprising a delivery device as described herein for generating variable density, phase, or size products can comprise two or more product substrates or two or more medicaments (e.g., therapeutic, prophylactic, or diagnostic agents) combined in a single product substrate.

In some embodiments, an inhaler is provided, comprising a delivery device as described herein for generating variable density, phase, or size products, and a product substrate comprising amniotic fluid, an amnion tissue preparation, or a combination thereof as described further herein.

In some embodiments, an inhaler is provided, comprising a delivery device as described herein for generating variable density, phase, or size products, and a product substrate comprising amniotic fluid, an amnion tissue preparation, or a combination thereof as described further herein, wherein the inhaler is an equine inhaler, a canine inhaler, or a feline inhaler.

In some embodiments, an inhaler is provided, comprising a delivery device as described herein for generating variable density, phase, or size products, and a product substrate comprising one or more active agents. In some embodiments, the one or more active agents are selected from acetyl cysteine, aclidinium bromide, albuterol, albuterol sulfate, amikacin sulfate, amniotic fluid, an amnion tissue preparation, arformoterol sulfate, atropine sulfate, aztreonam, beclomethasone dipropionate, bitolterol mesylate, budesonide, ciclesonide, cromolyn sodium, desflurane, dexamethasone sodium phosphate, dornase alfa, enflurane, epinephrine, ergotamine tartrate, flunisolide, fluticasone propionate, fomoterol fumarate, glycopyrrolate, halothane, indacaterol maleate, iloprost, insulin, ipratropium bromide, isoetharine hydrochloride, isoflurane, isoproterenol hydrochloride, levalbuterol hydrochloride, levodopa, loxapine, mannitol, metaproterenol sulfate, methacholine chloride, mometasone furoate, nedocromil sodium, nicotine, nitric oxide, olodaterol hydrochloride, pentamidine isethionate, pentetate calcium trisodium, pentetate zinc trisodium, pirbuterol acetate, revefenacin, ribavirin, salmeterol xinafoate, sevoflurane, stem cells, a stem cell preparation, terbutaline sulfate, tetrahydrocannabinol, cannabidiol, tiotropium bromide, tobramycin, trimcinolone acetonide, umeclidinium bromide, vilanterol trifenatate, xenon xe-133, zanamivir, epinephrine, sodium chloride, and combinations thereof.

In some embodiments, an inhaler is provided, comprising a delivery device as described herein for generating variable density, phase, or size products, and a product substrate comprising one or more active agents selected from AF, an amnion tissue preparation, stem cells, a stem cell preparation, or combinations thereof. In some embodiments, one or more additional active agents can be included in the product substrate of the inhaler. The one or more additional active agents can be selected from a drug, vaccine, DNA fragment, hormone or other treatment. The amount of medicament(s) in the inhaler can be determined by the required dose per puff, and can be determine by, e.g., a physician. Suitable agents for use as one or more additional agents include, e.g., bronchodilators, anti-inflammatories (e.g. corticosteroids), anti-allergics, anti-asthmatics, anti-histamines, and anti-cholinergic agents. Therapeutic proteins and peptides may also be employed for delivery by inhalation as one or more additional agents. Exemplary drugs which may be employed for delivery by inhalation as one or more additional agents (additional to the one or more initial active agents selected from AF, and amnion tissue preparation, stem cells, a stem cell preparation, and combinations thereof) include but are not limited to: albuterol, terbutaline, ipratropium, oxitropium, tiotropium, beclomethasone, flunisolide, budesonide, mometasone, ciclesonide, cromolyn sodium, nedocromil sodium, ketotifen, azelastine, ergotamine, cyclosporine, salmeterol, fluticasone, formoterol, procaterol, indacaterol, TA2005, omalizumab, zileuton, insulin, pentamidine, calcitonin, leuprolide, alpha-1-antitrypsin, interferons, triamcinolone, and pharmaceutically acceptable salts and esters thereof such as albuterol sulfate, formoterol fumarate, salmeterol xinafoate, beclomethasone dipropionate, triamcinolone acetonide, fluticasone propionate, tiotropium bromide, leuprolide acetate and mometasone furoate.

In some embodiments, a breathing system is provided herein, comprising a breathing device and a delivery device or inhaler described herein for generating inhalable products, e.g., variable density, size, or phase inhalable products. A breathing system is a medical system used to deliver inhalation assistance, and optionally, one or more inhalable medications. For example, a breathing system can deliver inhalation assistance by providing pressure assistance, oxygen delivery (including oxygen or a gas containing oxygen), carbon dioxide removal, or a combination thereof.

In some embodiments, the breathing device (e.g., a pressure-assisted breathing device or other device for providing inhalation assistance) and the delivery device or inhaler described herein for generating inhalable products (e.g., variable density, size, or phase inhalable products) are connected to a subject's airway or through one or more elements such as tubes. In some embodiments, a breathing system can include one or more elements, such as one or more tubes, a source of gas flow, one or more valves (such as an adjustable pressure-limiting valve), a reservoir bag, a patient interface device (including but not limited to nasal prongs or a cannula, nasopharyngeal tubes or prongs, an endotracheal tube, a tracheostomy tube, a mask) and the like. In some embodiments the breathing system is an invasive system (e.g., using an endotracheal tube or a tracheostomy tube for assisted breathing), such as in subjects or patients that require full mechanical breathing assistance, or in subjects or patients under anesthesia. In some embodiments, the breathing system is a non-invasive system (e.g., systems using nasal prongs or masks). In some embodiments, the breathing system can include a breathing circuit. For example, in some embodiments, the breathing system can comprise a ventilator circuit.

In some embodiments, the breathing system comprises a pressure-assisted breathing device. In some embodiments, the pressure-assisted breathing device can be selected from the group consisting of a mechanical ventilator, a continuous positive airway pressure system ("CPAP"), a bi-level positive airway pressure system ("BiPAP"), an automatic positive airway pressure system ("APAP"), and an adaptive servo ventilation system ("AVS"). A pressure-assisted breathing device is a device used for artificial ventilation that applies pressure to gases in or around a subject's airway to move, or assist in moving, gases into the lungs, out of the lungs, or a combination thereof. A pressure-assisted breathing device can increase or maintain lung volume, decrease the work of breathing for a subject, expand or prevent collapse of the subject's airways. Pressure, usually positive pressure, can be applied during or to assist in inhalation, or, in some embodiments, pressure can be applied during or to assist in exhalation, and combinations thereof.

In some embodiments, the breathing system can be an open system, a closed system, a semi-open system, or a semi-closed system. Open systems and semi-open systems use ambient air as the gas source and do not provide for rebreathing. An open system is unrestricted and provides no boundary between the subject's airway and the atmosphere. Semi-open systems utilize a restriction means, such as a reservoir or valve, that provides a partial boundary between the subject's airway and the atmosphere. Closed and semi-closed systems utilize a controlled gas source, such as oxygen or a non-ambient gas blend containing oxygen. A semi-closed system, such as a Mapelson A, B, C, D, E, or F system or a Humphrey ADE system, provides a full boundary between the subject's airway and the atmosphere for intake but allows venting of excess fresh gas into the atmosphere such that only partial rebreathing of exhaled air is possible. A closed system, such as a circle system, provides a fully closed boundary between the subject's airway and the atmosphere, preventing both air intake and venting and thus requiring complete rebreathing of exhaled gas.

In some embodiments, a breathing system is provided herein, comprising a pressure-assisted breathing device and the delivery device or inhaler described herein for generating inhalable products, e.g., variable density, size, or phase inhalable products. In some embodiments, the pressure-assisted breathing device can be a mechanical ventilator, such as a positive pressure ventilator, a negative pressure ventilator, or an intermittent abdominal pressure ventilator. Modes of mechanical ventilation can include volume modes (such as assist-control ventilation and synchronized intermittent-mandatory ventilation), pressure modes (such as pressure-controlled ventilation, pressure support ventilation, pressure controlled inverse ratio ventilation, and airway pressure release ventilation), dual modes (such as pressure regulated volume control), interactive modes (such as proportional assist ventilation and neurally adjusted ventilatory assist ventilation), inverse ratio ventilation, adaptive support ventilation, tube compensation, prone ventilation, high frequency oscillatory ventilation, high frequency percussive ventilation, positive end expiratory pressure, and combinations thereof. In some embodiments, a breathing system is provided herein, comprising a mechanical ventilator and an inhalable composition comprising amniotic fluid or an amnion tissue preparation. In some embodiments, the mechanical ventilator is an invasive mechanical ventilator.

Examples of invasive mechanical ventilators include, but are not limited to, transport or mobile ventilators, intensive care ventilators, bubble ventilators, and neonatal ventilators. In some embodiments, a breathing system is provided herein, comprising a non-invasive mechanical ventilation device, and an inhalable composition comprising amniotic fluid or an amnion tissue preparation. Examples of non-invasive mechanical ventilation devices include, but are not limited to, a CPAP, a BiPAP, an APAP, or an ASV. In some embodiments, breathing system is provided herein, comprising a non-invasive mechanical ventilation device selected from a CPAP, a BiPAP, an APAP, or an ASV, and an inhalable composition comprising amniotic fluid or an amnion tissue preparation.

Breathing systems described herein can include accessory devices, such as gas heating devices, gas humidifying devices, pressure regulators, pressure monitors, alarm systems, microprocessors, valves such as one-way valves, reservoirs such as gas reservoirs, and devices and structures for the introduction of inhalable medications (e.g., devices and structures in addition to the delivery devices or inhalers described herein for producing variable phase, size, or density products) into the breathing system. Additional devices and structures for introducing inhalable medications into the breathing system, other than the delivery devices or inhalers described herein for producing variable phase, size, or density products, can include, without limitation, nebulizers, pressurized metered dose inhalers, dry powder inhalers, tube joints, valves, spacers, and the like.

In some embodiments, a breathing system is provided, comprising a delivery device or inhaler as described herein for generating variable density, phase, or size products, and a product substrate comprising amniotic fluid, an amnion tissue preparation, or a combination thereof as described further herein.

In some embodiments, a breathing system is provided, comprising a delivery device or inhaler as described herein for generating variable density, phase, or size products, and a product substrate comprising one or more active agents. In some embodiments, the one or more active agents are selected from acetyl cysteine, aclidinium bromide, albuterol, albuterol sulfate, amikacin sulfate, amniotic fluid, an amnion tissue preparation, arformoterol sulfate, atropine sulfate, aztreonam, beclomethasone dipropionate, bitolterol mesylate, budesonide, ciclesonide, cromolyn sodium, desflurane, dexamethasone sodium phosphate, dornase alfa, enflurane, epinephrine, ergotamine tartrate, flunisolide, fluticasone propionate, fomoterol fumarate, glycopyrrolate, halothane, indacaterol maleate, iloprost, insulin, ipratropium bromide, isoetharine hydrochloride, isoflurane, isoproterenol hydrochloride, levalbuterol hydrochloride, levodopa, loxapine, mannitol, metaproterenol sulfate, methacholine chloride, mometasone furoate, nedocromil sodium, nicotine, nitric oxide, olodaterol hydrochloride, pentamidine isethionate, pentetate calcium trisodium, pentetate zinc trisodium, pirbuterol acetate, revefenacin, ribavirin, salmeterol xinafoate, sevoflurane, stem cells, a stem cell preparation, terbutaline sulfate, tetrahydrocannabinol, cannabidiol, tiotropium bromide, tobramycin, trimcinolone acetonide, umeclidinium bromide, vilanterol trifenatate, xenon xe-133, zanamivir, epinephrine, sodium chloride, and combinations thereof. In some embodiments, water can be an active agent. In some embodiments, water can be the sole active agent.

The devices and inhalers described herein can be used to generate variable density, size, or phase products, e.g., for delivery to a subject. The products are generated from a product substrate. In some embodiments, the product substrate is a suspension or solution comprising one or more therapeutic, prophylactic, or diagnostic agents, alone or in combination with one or more appropriate excipients, to be delivered as products generated by the devices or inhalers described herein. In some embodiments, the product substrate can be a solid or powder form of a therapeutic, prophylactic, or diagnostic agents, alone or in combination with one or more appropriate excipients.

In some embodiments, two or more product substrates may be present in multiple containers within a device or inhaler described herein. For example, a single product substrate may be provided per container in two or more containers within the device, or two product substrates may be contained within the same product substrate container. In some embodiments, a solid or powdered product substrate (e.g., a product substrate in particulate form such as a powder having a median size in the range of 1 to 10 microns) can be provided in a first substrate container and a solution (e.g., dissolved) or liquid product substrate for dissolving or suspending the solid or powder during operation of the device can be provided in a second container. For example, in some embodiments, a second container containing a liquid or solution product substrate can be positioned upstream of and in fluid communication with a first container containing a solid or powdered product substrate. Upon actuation of the device, the contents of the second container can enter the first container and dissolve or suspend the solid substrate in liquid substrate just prior to or during heating of one or more heating elements within the device. In some embodiments, the solid substrate can comprise one or more t therapeutic, prophylactic, or diagnostic agents and the liquid substrate can comprise one or more active therapeutic, prophylactic, or diagnostic agents. In some embodiments, the solid substrate can comprise one or more therapeutic, prophylactic, or diagnostic agents and the liquid substrate can contain no active therapeutic or prophylactic agents. In some embodiments, the solid substrate can comprise one or more active therapeutic, prophylactic, or diagnostic agents and the liquid substrate can consist essentially of water, a buffer, a salt, a surfactant, a pH adjusting agent, an excipient, or a combination thereof.

In some embodiments, a product substrate can be in the form of a liquid, a suspension, or a solution. In some embodiments, a product substrate liquid or solution can contain one or more active agents (e.g., therapeutic agents, prophylactic agents, or diagnostic agents). In some embodiments, a product substrate liquid or solution can consist essentially of the one more active agents. Representative therapeutic (including prodrugs), prophylactic, or diagnostic agents can include peptides, proteins, carbohydrates, nucleotides or oligonucleotides, small molecules, salts, or combinations thereof. Non-limiting examples of therapeutic, prophylactic, or diagnostic agents can include amniotic fluid, an amnion tissue preparation, a bronchodilator, a corticosteroid, a methylxanthine, a phosphodiesterase-4 inhibitor, an antimicrobial agent, an antibiotic, an antioxidant, an antiviral agent, an anti-fungal agent, an analgesic, a local anesthetic, an anti-inflammatory agent, an immunosuppressant agent, an anti-angiogenesis agent, an anti-allergenic agent, an anti-asthmatic, an anti-histamine, an anti-cholinergic agent, an enzyme cofactor, an essential nutrient, a growth factor, combinations thereof, and the like.

The active agents can be a small molecule active agent or a biomolecule such as an enzyme or protein, polypeptide, lipid, lipoprotein or nucleic acid. Suitable small molecule active agents include organic and organometallic compounds. In some instances, the small molecule active agent has a molecular weight of less than about 2000 g/mol, more preferably less than about 1500 g/mol, most preferably less than about 1200 g/mol. The small molecule active agent can be a hydrophilic, hydrophobic, or amphiphilic compound.

In some embodiments, a product substrate liquid or solution can comprise one or more active agents and one or more pharmaceutically acceptable excipients, such as water, solvents, diluents, pH modifying agents, preservatives, antioxidants, suspending agents, wetting agents, viscosity modifiers, tonicity agents, stabilizing agents, and combinations thereof. Suitable pharmaceutically acceptable excipients are preferably selected from materials which are generally recognized as safe (GRAS) for use in respiratory administration.

In some embodiments, product substrate solutions can include pH adjusting agents or buffers to maintain a desired pH for the product substrate for storage, delivery into a subject, or a combination thereof. In some embodiments, the desired pH can be based on the conditions necessary to maximize stability of an active agent in the product substrate. In some embodiments, the product substrate or substrates can have a pH ranging from 3.5 to 10.0. In some embodiments, the product substrate or substrates can have a pH ranging from 5.5 to 8.5. In some embodiments, the product substrate or substrates can have a pH ranging from about pH 4.0 to about pH 8.5, from about pH 4.5 to about pH 7.5, from about pH 5.0 to about pH 6.5, from about pH 5.6 to about pH 6.3, from about pH 5.7 to about pH 6.2. In some embodiments, suitable pH values for the product substrate or substrates include about 4.0, about 4.5, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6. About 6.7, about 6.8, about 6.9, about 7.0, about 7.1, about 7.2, about 7.3, about 7.4, about 7.5, or about 8.5. In some embodiments, the pH of the product substrate or substrates is about 5.8. Suitable buffers include buffers generally recognized as safe (GRAS) for usage in lung tissue. Exemplary suitable buffers can include buffers selected from acetate, borate, carbonate, citrate, succinate, and phosphate buffers. In some embodiments, the buffer can be sodium citrate/citric acid. Alternatively, imidazole or histidine or another base or acid that maintains the pH in the range of about pH 3.0 to about 10.0 or about pH 4.5 to about pH 8.5 can be used.

In some embodiments, product substrate solutions can have a tonicity equivalent to a 0.5-7.0% solution of sodium chloride. In some embodiments, the product substrate solutions can be isotonic (e.g., have a tonicity equal to that of a 0.9% solution of sodium chloride). In some embodiments, product substrate solutions can include one or more tonicity agents to adjust the tonicity range of the substrate formulation. Exemplary suitable tonicity agents can include tonicity agents selected from glycerin, mannitol, sorbitol, sodium chloride, and other electrolytes.

In some embodiments, product substrate solutions can contain one or more preservatives, e.g., to prevent bacterial contamination. Non-limiting exemplary suitable preservatives include polyhexamethylenebiguanidine (PHMB), benzalkonium chloride (BAK), stabilized oxychloro complexes, phenylmercuric acetate, chlorobutanol, sorbic acid, chlorhexidine, benzyl alcohol, parabens, thimerosal, and the like, and combinations thereof.

In some embodiments, a product substrate solutions can contain one or more surfactants to facilitate inhalation or absorption of the products generated by the devices described herein. Non-limiting exemplary surfactants polyoxyethylene sorbitol esters such as polysorbate 80 (Tween 80) and polysorbate 20 (Tween 20); propylene-polyoxyethylene esters such as poloxamer 188, polyoxyethylene alcohols such as Brij35, mixtures of polysorbate surfactants with phospholipids such as phosphatidylcholine and derivatives (e.g., dipalmitoyl, dioleoyl, dimyristyl, or 1-palmitoyl), phospholipid glycerols such as dimyristol glycerol, lysophosphatidylcholine and derivatives thereof, lysolecithin, a mixture of polysorbate with cholesterol, a mixture of polysorbate surfactant with sorbitan surfactant (such as sorbitan monooleate, dioleate, trioleate, and the like), poloxamer surfactants, and combinations thereof. In some embodiments, the product substrate or product substrate solution can be free of surfactant.

In some embodiments, product substrate solutions can contain one or more pharmaceutically acceptable excipients or carriers such as dispersing agents, wetting agents, stabilizing agents, suspending agents, adjuvants, preservatives, flavorants, lipids, amino acids, surfactants, polymers, absorption enhancers, and the like, or combinations thereof. Exemplary excipients for use as stabilizing agents can include any sugar or sugar alcohol or any amino acid, such as, e.g., lactose, anhydrous lactose, mannitol, glucose, sucrose, trehalose, sorbitol, 1-O-alpha-D-glucopyranosyl-D-mannitol (e.g., Isomalt), xylitol, maltitol, lactitol, erythritol, arabitol, ribitol, fructose, mannose, galactose, raffinose, maltose, sorbose, cellobiose, inulin, sucrose, trehalose, raffinose, stachyose, sorbitol, dextrose, and combinations thereof. Additional optional excipients can include comprises one or more materials selected from an organic acid, organic base, polyol, peptide, protein, fat, fatty acid, amino acid (aspartic acid, glutamic acid, leucine, L-leucine, isoleucine, lysine, valine, methionine, phenylalanine, glycine, arginine, cysteine, alanine, serine, phenylalanine, lysine, N-acetyl-L-cysteine or a pharmaceutically acceptable salt, solvate, hydrate, or polymorph thereof), carbohydrate (e.g. mannitol, sorbitol, xylitol, mal ita, lactitol, erythritol, arabitol, ribitol, glucose, fructose, mannose, galactose, lactose, sucrose, raffinose, maltose, sorbose, cellobiose, trehalose, maltodextrins, dextrans, inulin, 1-O-alpha-D-glucopyranosyl-D-mannitol (Isomalt)), or their pharmaceutically acceptable solvate, hydrate or polymorph, phospholipid, triglyceride, detergent, polymer, sodium citrate, sodium ascorbate, lecithin, soya lecithin, dipalmitoylphosphatidyl diphospholidilipholina, ethanolamine, dipalmitoylphosphatidylinositol, phosphatidylcholines, phosphatidylethanolamine, phosphatidylglycerols, phosphatidylinositol, phosphatidylserine, sodium lauryl sulfate, magnesium lauryl sulfate; PEG 6000, PEG 3000 Tween 80, Poloxamer 188, leucine, L-leucine, isoleucine, lysine, valine, methionine, phenylalanine, glycine, arginine, aspartic acid, glutamic acid, cysteine, alanine, serine, or their pharmaceutically acceptable salt, solvate, hydrate or polymorph, and combinations thereof.

A product substrate can comprise one or more active agents (e.g., therapeutic agents, prophylactic agents, or diagnostic agents). The active agent can be present in its neutral form, or in the form of a pharmaceutically acceptable salt. In some embodiments, the product substrate can be a formulation containing a salt of an active agent due to one or more of advantageous physical properties, such as enhanced stability or a desirable solubility or dissolution profile.

The one or more active agents can be any appropriate active agent (e.g., therapeutic agents, prophylactic agents, or diagnostic agents). For example, in some embodiments, the one or more active agents can be any active agent suitable for respiratory administration to a subject. In some embodiments, the one or more active agents can be an active agent for treating or preventing a respiratory disorder or for treating a tissue of the respiratory tract. For example, in some embodiments, the one or more active agents can be an active agent for treating or preventing a respiratory disorder selected from chronic obstructive pulmonary disease (COPD), asthma, acute asthma, chronic asthma, severe asthma, allergic asthma, bronchial asthma, intrinsic asthma (e.g., late asthma and airway hyper-responsiveness), respiratory distress syndrome of the newborn, reversible respiratory disease, cystic fibrosis, bronchospasms, bronchitis, chronic bronchitis, bronchiectasis, alpha-1 antitrypsin emphysema, emphysema, associated cor pulmonale (heart disease secondary to disease of the lungs and respiratory system) with pulmonary hypertension, right ventricular hypertrophy and right heart failure, pulmonary hypertension, interstitial lung disease, pulmonary fibrosis, pneumonia, interstitial pneumonia, lung infections, idiopathic pulmonary fibrosis, cystic fibrosis, tuberculosis, pneumonia, severe acute respiratory syndrome, infection, pulmonary embolus, tuberculosis, pulmonary arterial hypertension, pulmonary edema, *pneumocystis* pneumonia, covid-19, and acute respiratory distress syndrome. In some embodiments, the one or more active agents can be an active agent for treating or preventing lung injury related to systemic inflammatory response syndrome (SIRS), sepsis, severe sepsis, septic shock, and multiple organ dysfunction syndrome (MODS). In some embodiments, the one or more active agents can be an active agent for treating or preventing respiratory disorder such as a respiratory or respiratory-related infection. For example, in some embodiments, the one or more active agents can be an active agent for treating bacterial, fungal, or viral infections of the respiratory system. In some embodiments, the one or more active agents can be an active agent for treating infections such SARS-CoV-2, SARS-CoV, MERS, and Pertussis. In some embodiments, the one or more active agents can be an active agent for treating or preventing a lung injury, such as an acute inhalation injury, an injury from chemical irritants, asphyxiants, smoke, heat, riot control agents, chemical warfare agents, an similar exposures. In some embodiments, the one or more active agents can be a vaccine (e.g., a vaccine delivered through respiratory administration) for treating or preventing a respiratory disorder.

In some embodiments, the one or more active agents can be any active agent for treating or preventing a non-respiratory disorder or for treating a portion of the subject's body outside of the respiratory tract that is suitable for respiratory administration. For example, in some embodiments, the one or more active agents can be an active agent for treating or preventing a non-respiratory disorder selected from an autoimmune disease (e.g., rheumatoid arthritis, juvenile rheumatoid arthritis, and the like), a spondyloarthropathy (e.g., ankylosing spondylitis or psoriatic arthritis), an intestinal disease (e.g., Crohn's disease), diabetes, or a skin disease (psoriasis). In some embodiments, the one or more active agents can be an active agent for treating or preventing sarcoidosis, systemic inflammatory response syndrome (SIRS), sepsis, severe sepsis, septic shock, and multiple organ dysfunction syndrome (MODS). In some embodiments, the one or more active agents can be an active agent for treating or preventing a non-respiratory disorder that is a non-respiratory infection, such as a non-respiratory viral, bacterial, or fungal infection. In some embodiments, the one or more active agents can be an active agent for treating or preventing a non-respiratory disorder that is a pain disorder selected from neuropathic, nociceptive, acute, chronic and disease-specific pain (e.g., pain associated with osteoarthritis or fibromyalgia). In some embodiments, the one or more active agents can be a vaccine (e.g., a vaccine delivered through respiratory administration) for treating or preventing a non-respiratory disorder.

In some embodiments, the product substrate can comprise from about 0.001% to about 100% of one or more active agents. In some embodiments, the active agents can be present in an amount of from about 50% to about 100%, from about 55% to about 100%, from about 65% to about 100%, from about 75% to about 100%, from about 80% to about 100%, from about 85% to about 100%, from about 90% to about 100%, from about 95% to about 100%, from about 96% to about 100%, from about 97% to about 100%, from about 98% to about 100%, from about 99% to about 100%, from about 25% to about 90%, from about 35% to about 90%, from about 40% to about 90%, from about 45% to about 80%, from about 50% to about 70%, from about 55% to about 75%, from about 1% to about 20%, from about 5% to about 20%, from about 10% to about 20%, from about 15% to about 20%, from about 0.01% to about 10%, from about 0.01% to about 5%, from about 0.01% to about 1%, from about 0.1% to about 10%, from about 0.5% to about 5%, from about 1% to about 5%, from about 1% to about 10%, from about 0.1% to about 4%, from about 0.1% to about 2%, from about 0.1% to about 1%, from about 0.01% to about 0.1%, from about 0.01% to about 0.5%, from about 10% to about 20%, from about 15% to about 20%, from about 20% to about 30%, from about 90% to about 98%, from about 90% to about 97%, from about 95% to about 99%, from about 90% to about 95%, or from about 93% to about 98% of the product substrate.

In some embodiments, the one or more active agents can be one or more bronchodilators. Bronchodilators assist in opening a subject's airways to make breathing easier. Bronchodilators can be short-acting or long-acting. Short-acting bronchodilators are often used for emergency situations or as needed for fast relief of symptoms. Long-acting bronchodilators are used to treat chronic conditions (e.g., COPD) over an extended period of time. Long-acting bronchodilators are usually taken once or twice daily over a long period of time (e.g., weeks, months, or years). Exemplary short-acting bronchodilators include, but are not limited to, anti-cholinergics such as ipratropium (e.g., ATROVENT®, in COMBIVENT®, in DUONEB®), beta2-agonists such as albuterol (e.g., VOSPIRE ER®, in COMBIVENT®, in DUONEB®), and levalbuterol (e.g., XOPENEX®). Exemplary long-acting bronchodilators include, but are not limited to, anticholinergics such as aclidinium (e.g., TUDORZA®), tiotropium (e.g., SPIRIVA®), or umeclidinium (e.g., INCRUSE ELLIPTA®), beta2-agonists such as arfonnoterol (e.g., BROVANA®), formoterol (e.g., FORADIL®, PERFOROMIST®), indacaterol (e.g., ARCAPTA®), salmeterol (e.g., SEREVENT®), and olodaterol (e.g., STRIVERDI RESPIMAT®).

In some embodiments, the one or more active agents can be one or more corticosteroids. Corticosteroids can reduce inflammation, making breathing and air flow to the lungs easier. There are several corticosteroids. Non-limiting exemplary corticosteroids include fluticasone (e.g., FLOVENT®), budesonide (e.g., PULMICORT®), prednisolone, and combinations thereof. In some embodiments, one or more corticosteroids can be included in a combination with one ore more bronchodilators.

In some embodiments, the one or more active agents can be one or more methylxanthines. Methylxanthines are some-time used in cases where a subject has severe difficulty with COPD and regular or first-line treatments alone do not provide adequate relief. A non-limiting exemplary methylxanthines is theophylline (e.g., THEO-24®, THEOLAIR®, ELIXOPHYLLINE®, QUIBRON-T®, UNIPHYL®, and ELIXOPHYLLIN®). In some embodiments, one or more methylxanthines can be included in a combination with one ore more bronchodilators.

In some embodiments, the one or more active agents can be one or more phosphodiesterase-4 inhibitors such as, e.g., roflumilast (e.g., DALIRESP®). In some embodiments, one or more phosphodiesterase-4 inhibitors can be included in a combination with one or more long-acting bronchodilators.

In some embodiments, the one or more active agents can be one or more vasodilators or pulmonary vasodilators. Non-limiting exemplary vasodilators include nitric oxide, phosphodiesterase inhibitors, prostacyclin ($PGI_2$) analogs, prostaglandin $E_1$ ($PGE_1$), endothelin receptor antagonists, epoprostenol, and iloprost.

In some embodiments, the one or more active agents can be one or more antimicrobial agents to kill or inhibit the growth of microbes such as bacteria, fungi, viruses, or parasites. Antimicrobial agents include antiviral agents, antibacterial agents, antiparasitic agents, and anti-fungal agents. Non-limiting exemplary antiviral agents include ganciclovir Sand acyclovir. Non-limiting exemplary antibiotic agents include aminoglycosides such as streptomycin, amikacin, gentamicin, and tobramycin, ansamycins such as geldanamycin and herbimycin, carbacephems, carbapenems, cephalosporins, glycopeptides such as vancomycin, teicoplanin, and telavancin, lincosamides, lipopeptides such as daptomycin, macrolides such as azithromycin, clarithromycin, dirithromycin, and erythromycin, monobactams, nitrofurans, penicillins, polypeptides such as bacitracin, colistin and polymyxin B, quinolones, sulfonamides, and tetracyclines. Other non-limiting exemplary antimicrobial agents can include antimicrobial peptides, iodine, silver compounds, moxifloxacin, ciprofloxacin, levofloxacin, cefazolin, tigecycline, gentamycin, ceftazidime, ofloxacin, gatifloxacin, amphotericin, voriconazole, and natamycin.

In some embodiments, the one or more active agents can be one or more local anesthetics for causing reversible local anesthesia and loss of the sensation of pain. Non-limiting exemplary local anesthetics include ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethysoquin, dimethocaine, diperodon, dycyclonine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, psuedococaine, pyrrocaine, ropivacaine, salicyl alcohol, tetracaine, tolycaine, trimecaine, zolamine, and combinations thereof. In some embodiments, a hyaluronidase enzyme, can be present in combination with the one or more local anesthetics to accelerate and improves dispersal of the local anesthetic.

In some embodiments, the one or more active agents can be one or more anti-inflammatory agents. Anti-inflammatory agents reduce inflammation and include steroidal and non-steroidal drugs. Non-limiting exemplary steroidal anti-inflammatory agents include glucocorticoids, progestins, mineralocorticoids, and corticosteroids. Other non-limiting exemplary anti-inflammatory agents include triamcinolone acetonide, fluocinolone acetonide, prednisolone, dexamethasone, loteprednol, fluorometholone, ibuprofen, aspirin, and naproxen. Non-limiting exemplary immune-modulating anti-inflammatory agents include cyclosporine, tacrolimus and rapamycin. Non-limiting exemplary non-steroidal anti-inflammatory drugs (NSAIDs) include mefenamic acid, aspirin, Diflunisal, Salsalate, Ibuprofen, Naproxen, Fenoprofen, Ketoprofen, Deacketoprofen, Flurbiprofen, Oxaprozin, Loxoprofen, Indomethacin, Sulindac, Etodolac, Ketorolac, Diclofenac, Nabumetone, Piroxicam, Meloxicam, Tenoxicam, Droxicam, Lornoxicam, Isoxicam, Meclofenamic acid, Flufenamic acid, Tolfenamic acid, elecoxib, Rofecoxib, Valdecoxib, Parecoxib, Lumiracoxib, Etoricoxib, Firocoxib, Sulphonanilides, Nimesulide, Niflumic acid, and Licofelone. In some embodiments, anti-inflammatory agents can include anti-inflammatory cytokines. Non-limiting exemplary cytokines include IL-10, IL-17, IL-25, TGF-β, and IL-35.

In some embodiments, the one or more active agents can be one or more biologics.

In some embodiments, the one or more active agents can be one or more eukaryotic cells, such as stem cells (e.g., mesenchymal stem cells), immune cells (e.g., T lymphocytes, B lymphocytes, natural killer cells, and dendritic cells), or combinations thereof. In some embodiments, the one or more active agents can be one or more stem cells or stem cell preparations. Non-limiting exemplary stem cells include those obtained from lungs (e.g., lung epithelial progenitor cells), fat tissue (e.g., mesenchymal stem cells), bone tissue (e.g., mesenchymal stem cells), umbilical cord blood, embryos or amniotic fluid or amniotic tissue, and bone marrow (induced pluripotent stem cells), and combinations thereof. Non-limiting exemplary stem cell preparations include a lung stem cell preparation such as a lung epithelial progenitor cell preparation, a mesenchymal stem cell (MSC) preparation (e.g., a MSC preparation obtained from fat tissue or bone marrow), an umbilical cord blood stem cell preparation, an embryonic stem cell preparation, and a human induced pluripotent stem cell preparation, or combinations thereof.

In some embodiments, the one or more active agents can be one or more growth factors. Growth factors, also known as a cytokines, are proteins capable of stimulating cellular growth, proliferation, and/or cellular differentiation. Non-limiting exemplary growth factors include transforming growth factor beta (TGF-β), transforming growth factor alpha (TGF-α), granulocyte-colony stimulating factor (GCSF), granulocyte-macrophage colony stimulating factor (GM-CSF), nerve growth factor (NGF), neurotrophins, platelet-derived growth factor (PDGF), erythropoietin (EPO), thrombopoietin (TPO), myostatin (GDF8), growth differentiation factor-9 (GDF9), acidic fibroblast growth factor (aFGF or FGF-1), basic fibroblast growth factor (bFGF or FGF-2), epidermal growth factor (EGF), vascular endothelial growth factor (VEGF) and hepatocyte growth factor (HGF).

In some embodiments, the one or more active agents can be one or more therapeutic or prophylactic peptides, such as, e.g., insulin (e.g., AFREZZA®). In some embodiments, the insulin can be selected from recombinant insulin, insulin isolated from a mammal, substituted insulin, pro-insulin, semi-synthetic insulin, synthetic insulin, or a pharmaceutically acceptable salt, solvate, hydrate or polymorph thereof, and combinations thereof. In some embodiments, the insulin can be selected from recombinant human insulin, simple insulin, insulin aspart, protamine insulin aspart, insulin detemir, insulin glargine, insulin glulisin, isofan insulin, insulin lispro or a pharmaceutically acceptable salt, solvate, hydrate or polymorph thereof, and combinations thereof.

In some embodiments, the one or more active agents can be one or more growth hormones (e.g. human growth hormone).

In some embodiments, the one or more active agents can be one or more therapeutic or prophylactic enzymes, such as enzymes such as dornase alfa (PULMOZYME®).

In some embodiments, the one or more active agents can be one or more antibodies, including, for example, daclizumab, bevacizumab (e.g., Avastin®), ranibizumab (e.g., Lucentis®), basiliximab, ranibizumab, and pegaptanib sodium or peptides like SN50, and antagonists of NF.

In some embodiments, the one or more active agents can be one or more TNFα inhibitors. TNFα inhibitors are agents that interfere with TNFα activity. Non-limiting exemplary TNFα inhibitors include anti-TNFα human antibodies and antibody portions such as those described in U.S. Pat. Nos. 6,090,382; 6,258,562; 6,509,015; and U.S. patent application Ser. Nos. 09/801,185 and 10/302,356, each of which is incorporated herein by reference. In some embodiments, a TNFα inhibitor can be infliximab (Remicade®) described in U.S. Pat. No. 5,656,272 (incorporated herein by reference), CDP571 (humanized monoclonal anti-TNF-α IgG4 antibody), CDP870 (humanized monoclonal anti-TNF-α antibody fragment), anti-TNF dAb, CNTO148 (e.g., golimumab, Medarex, Centocor), adalimumab (e.g., HUMIRA®), C2E7, an anti-TNFα antibody or fragment thereof. Additional TNF antibodies that can be used as active agents herein include those described in U.S. Pat. Nos. 6,593,458; 6,498,237; 6,451,983; and 6,448,380, each of which is incorporated herein by reference. Other TNFα inhibitor can include a TNF fusion protein, e.g., etanercept (e.g., Enbrel®), or a recombinant TNF binding protein (e.g., r-TBP-I).

In some embodiments, the one or more active agents can be one or more oligonucleotides. Non-limiting exemplary oligonucleotides include siRNAs, microRNAs, DNA, and RNA.

In some embodiments, the one or more active agents can be one or more enzyme cofactors, and/or one or more essential nutrients. Exemplary cofactors include vitamin C, biotin, vitamin E, and vitamin K. Exemplary essential nutrients are amino acids, fatty acids, and the like.

In some embodiments, the one or more active agents can be one or more anti-proliferative drugs such as paclitaxel and derivatives. Non-limiting exemplary anti-proliferative drugs include, but are not limited to, amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epipodophyllotoxins, epirubicin, etoposide, etoposide phosphate, fludarabine, fluorouracil, gemcitabine, hydroxycarb amide, idarubicin, ifosfamide, innotecan, leucovorin, liposomal doxorubicin, liposomal daunorubici, lomustine, mechlorethamine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, teniposide, tegafur-uracil, temozolomide, teniposide, thiotepa, tioguanine, topotecan, treosulfan, vinblastine, vincristine, vindesine, vinorelbine, taxol and derivatives thereof, trastuzumab (e.g., HERCEPTIN®), cetuximab, and rituximab (e.g., RITUXAN® or MABTHERA®), bevacizumab (e.g., AVASTIN®), and combinations thereof. Non-limiting exemplary pro-apoptotic agents include, but are not limited to, fludarabinetaurosporine, cycloheximide, actinomycin D, lactosylceramide, 15 d-PGJ(2)5, and combinations thereof.

In some embodiments, the one or more active agents can be one or more selective enzyme inhibitors, such as, e.g., sildenafil (e.g., Viagra®), vardenafil HCl (e.g., Levitra®), tadalafil (e.g., Cialis®) and yohimbine (e.g., Yohimbine®).

In some embodiments, the one or more active agents can be water. In some embodiments, water can be the sole active agent. For example, in some embodiments of the devices described herein, a device can be used to provide a humidifying effect to a subject. For example, in some embodiments of the devices described herein, a device can be used to provide a humidifying effect to at least a portion of a subject's respiratory tract by providing variable density, size, or phase water.

In some embodiments, the one or more active agents can be one or more diagnostic agent for, e.g., imaging or otherwise assessing a site of application (e.g., lung tissue). Non-limiting exemplary diagnostic agents include paramagnetic molecules, fluorescent compounds, magnetic molecules, and radionuclides, x-ray imaging agents, and contrast media. Diagnostic agents can also include ligands or antibodies which are labelled with the foregoing or bind to labelled ligands or antibodies which are detectable by methods known to those skilled in the art.

In some embodiments, the one or more active agents can be one or more agents suitable for pulmonary delivery. Some exemplary active agents that can be administered through pulmonary delivery, or are under investigation for possible pulmonary delivery include 1018-iss, 1311-hua33, 13-cis-retinoic acid, 18f-fdg, 1d09c3, 2-pentenylpenicillin, 825780 dna antiviral vaccine, a/t/s, erythromycin, a-1 antitrypsin, abacivir; lamivudine, abarelix, abatacept, abciximab, abetiinus sodium, abn 912, abt 325/abt 874, abt 874, abx-i18, ac vaccine, ac162352, ac2592, acadesine, acamprosate, acarbore, acarbose, acatophenazine, acc-001, acebutolol, acebutolol hydrochloride, aceclofenac, acetamide, acetaminophen, acetaminophen; aspirin; caffeine, acetaminophen; butalbitol, acetaminophen; codeine phosphate, acetazolamide, acetazolamide sodium, acetic acid, acetic acid; hydrocortisone, acetohexamide, acetohydroxamic acid, acetophenazine, acetyl sulfisoxazole, acetylcholine chloride, acetylcysteine, acetylsalicylic acid, acid glycoprotein, acitretin, aclometasone, acrivastine; pseudoephedrine, actemra, acth, activated recombinant factor vii, acyclovir, acyclovir sodium, adalimumab, adapalene, adefovir dipivoxil, ademetionine, adenine, adeno associated viral vector, adenosine, adenoviral vector, adenovirus, adenovirus p53, adinazolam, adiponectin, adpedf, adrafinil, adrenaline, adrenocorticotropic hormone, advate antihemophilic factor plasma/albumin-free method, advexin, aeg 35156, afelimomab, ag-707, agalsidase alpha, agalsidase beta, aglucosidase alpha, agspsca mab, agtc 0106, almotriptan, albendazole, albumin iodinated i-125 serum, albumin iodinated i-131 serum, albumin, human, albuterol, albuterol sulfate, albuterol; ipatropium, alclometasone dipropionate, alcohol, aldesleukin, aldesleukin, i12, aldosterone, alefacept, alemtuzumab, alendronate, alendronic acid; colecalciferol, alfentanil, alfentanil hcl, alfentanil hydrochloride, alferon n injection, alfimeprase, alfuzosin, alfuzosin hcl, alglucerase, alicaforsen, alitretinoin, alizapride, allopurinol, allopurinol sodium, allovectin-7, allylprodine, alminoprofen, almotriptan, alosetron hcl, alperopride, alpha-1 antitrypsin, alpha-1 proteinase inhibitor, alpha-galactosidase a, alphaprodine, alpidem, alprazolam, alprostadil, alseroxion, alteplase (tpa), altretamine, altu-238, aluminum hydroxide, aluminum hydroxide; magnesium carbonate, alvac, alvac gp100, alvac mn120 tmgmp, alvac-cea/b7.1, amantadine, amantadine hydrochloride, ambenonium chloride, ambrisentan, amcinonide, ame 527, amerscaen medronate ii, amerscam stannous agent, amerscan hepatate ii, amesergide, amfenac, amg 8/amg 531/amg 623/amg 714, amg 221, amg 317, amg 403, amg 517, amg102/amg 386/amg 479/amg 623/amg 655/amg 706, amifostine, amikacin sodium, amikacin sulfate, amiloride hydrochloride, amiloride hydrochloride dihydrate, amino acids, amino acids; glycerin; electrolytes, amino alcohol, aminoacetic acid, aminocaproic acid, aminoglutethimide, aminohippurate sodium, aminolevulinic acid, aminolevulinic acid hydrochloride, aminophylline, aminopropylon, aminosalicylic acid, amiodarone, amiodarone hcl, amiodarone hydrochloride, amisulpride, amitriptyline, amitriptyline hydrochloride, amitriptyline; chlordiazipoxide, amixetrine, amlexanox, amlodipine, amlodipine besylate, amlodipine; atorvastatin, amlodipine; benazepril, ammonium chloride, ammonium lactate, amobarbital sodium; ecobarbital sodium, amoxapine, amoxicillin, amoxicillin; clarithromycin; lansoprazole, amperozide, amphenidone, amphetamine, amphetamine; dextroamphetamine, amphotericin b, ampicillin, ampicillin, ampicillin and sulbactam, ampicillin sodium, ampicillin trihydrate, ampicillin; clavulonate, amprenavir, amrinone lactate, amylin, amylpenicillin, amytal sodium, anagrelide hydrochloride, anakinra, anastrazole, andropinirole, androstenedione, angiocol, angiotensinogen, anidulafungin, anileridine, anisindione, an-sulfur colloid, anti-cd16 mab, anti-cd23 mab, anti-cd3 mab, anti-cd80 mab, antidiuretic hormone, antihemophelic factor (factor viii), antihemophilic factor (recombinant), anti-hiv-1 mab, anti-hsp90 mab, anti-idiotype cancer vacccine, anti-ige, anti-il-4, anti-inhibitor coagulant complex, anti-interferon-gamma, anti-lfa-1, mouse, anti-human, monoclonal antibody, anti-lymphotoxin beta receptor mab, antimullerian hormone, anti-pem mab, antisense oligonucleotide, anti-staph mab, anti-tac(fv)-pe38 immunotixin, antivenin crotalidae polyvalent injection, antivenin lactrodectus mactans, antivenin micrurus fulvius, apazone, apc8024, aplidine, apo21/trial (amg 951), apo-cilazapril/hctz, apo-digoxin, apo-etidronate, apo-feno-super, apo-flecainide, apokyn, apo-levetiracetam, apo-medroxy, apo-meloxicam, apo-methotrexate, apo-metoprolol sr, apo-midodrine, apo-mirtazapine, apomorphine, apomorphine hydrochloride, apomorphinediacetate, apo-omeprazole, apo-ondansetron, apo-oxcarbazepine, apo-ramipril, apo-ranitidine, apo-risperidone, apo-sumatriptan, apo-topiramate, apraclonidine, aprepitant, aprotinin bovine, argatroban, arginine hydrochloride, arimoclomol, aripiprazole, arsenic trioxide, articaine hydrochloride/epinephrine, asparaginase, aspirin, aspirin; caffeine; orphenadrine citrate, aspirin; dipyridamole, aspirin; hydrocodeine; caffeine, aspirin; hydrocodone, aspirin; meprobamate, aspirin; pravastatin, at-1001, atazanivir sulfate, atenolol, atenolol; chlorthalidone, atl 1101, atl 1102, atomoxetine, atorvastatin calcium, atovaquone, atovaquone; proguanil hcl, atracurium besylate, atrial natriuretic peptide, atropine sulfate, atropine sulfate/edrophonium chloride, attenuated live measles vaccine, attenuated rotavirus vaccine, auranofin, aurexis tefibazumab, autologous renal cell tumor vaccine, autologous tumor, autologus gp100-reactive pbl and til plus rf-gp100p209, ave 0005, ave 9633 maytansin-loaded anti-cd 33 mab, avi-4065, aviptadil, avr 118, avx101, azacitidine, azacyclonol, azatadine, azathioprine, azathioprine sodium, azelaic acid, azelastine, azelastine hcl, azidocillin, azithromycin, azt; 3tc; abacavir, aztreonam, aztreonam lysinate, bacampicillin, bacille calmette-guerin, bacitracin, bacitracin zinc, bacitracin; polymyxin b sulfate, baclofen, bacterial lipase, bacteriostatic sodium chloride, bacteriostatic water, bapineuzumab, barium sulfate, basiliximab, bavituximab, bcl-2 antisense oligonucleotide, g-3139, becaplermin, becatecarin, beclomethasone dipropionate, belatacept, benactyzine, benazepril hydrochloride, benazepril; hydrochlorothiazide, bendroflumethiazide, bendroflumethiazide; nadolol, benmoxine, benoxaprofen, benperidol, benserazide, bentoquatam, benzamycin, benzoic acid, benzonatate, benzoyl peroxide, benzoyl peroxide; clindamycin, benzphetamine, benzphetamine; diethylproprion, benzpiperylon, benzquinamide, benzquinamide hydrochloride, benztropine, benztropine mesylate, benzydramine, benzylmorphine, benzylpenicillin, beractant, bertezomib, beta-2, betahistine, betaine, betaine anhydrous, betamethasone acetate, betamethasone dipropionate, betamethasone sodium phosphate, betamethasone valerate, betaseron, betaxolol, betaxolol hydrochloride, bethanechol chloride, bevacizumab, bexarotene, bezitramide, bicalutamide, bimatoprost, bimosiamose disodium, binedaline, biperiden, biphasic insulin aspart, bisoprolol fumarate, bitolterol, bitolterol mesylate, bivalirudin, bivatuzumab, bleomycin, bleomycin sulfate, blx 883, bortezomib, bosentan, botulinum toxin type a+b, bovine bile extract, br3-fc, bretylium tosylate, brimonidine tartrate, brinzolamide, brofaromine, bromelain; vit c; I glutamine; msm; quercetin, bromfenac, bromisovalum, bromocriptine, bromocriptine mesylate, bromodiphenhydramine; codeine, bromopheniramine; dextromethorphin; pseudoephedrine, bromopheniramine; pseudophedrine, bromopheniramine; pseuodophedrine, bromopride, bromperidol, brompheniramine, brompheniramine maleate, brucine, buclizine, budesonide, budesonide; formoterol fumarate, budesonide; formoterol, budipine, bufexamac, buffered intrathecal electrolytes/dextrose, bumetanide, bupivacaine hydrochloride, bupivacaine hydrochloride/epinephrine, bupivacaine hydrochloride/epinephrine bitartrate, bupivocaine; lidocaine, buprenorphine, buprenorphine hydrochloride, buprenorphine hydrochloride/naloxone hydrochloride, bupropion, bupropion hydrochloride, buramate, busalazide disodium, buserelin, buspirone, buspirone hydrochloride, busulfan, butabarbital, butaclamol, butalbital, butalbital; acetaminophen, butalbital; acetaininophen; caffeine, butalbital; apap, butalbital; asa, butanamide, butaperazine, butenafine hcl, butoconazole nitrate, butorphanol, butorphanol tartrate, butriptyline, ca4p, cabergoline, caffeine, caffeine citrate, caffeine; ergotamine, caiv-t, calciferol, calcipotriene, calcitonin, calcitonin, salmon, calcitriol, calcium acetate, calcium carbonate; residronate, calcium chloride, calcium disodium versenate, calcium gluconate, calcium-n-carboamoylaspartate, calfactant, candesartan, cannobinoids, capecitabine, capreomycin sulfate, capromab pendetide, captodiamine, captopril, captopril; hctz, capuride, carbachol, carbamazepine, carbamic acid, carbcloral, carbenicillin, carbidopa, carbidopa; levodopa, carbinoxamine maleate, carbiphene, carbocaine, carbon 13 urea, carbon 14 urea, carboplatin, carboprost tromethamine, carboxylic acid, carboxypeptidase, carbromal, cardioplegic solution, cardiotrophin-1, carfecillin, carindacillin, carisoprodol, carmustine, caroxazone, carphenazine, carpipramine, carprofen, carteolol hydrochloride, carvedilol, caspofungin acetate, caspofungin msd, cat 3888, catumaxomab, cb 001, cc10, ccr5 mab, cdp 791, cea, cefaclor, cefadroxil, cefamandole, cefazolin, cefazolin sodium, cefdinir, cefditoren pivoxil, cefepime hydrochloride, cefibutin, cefinetazole, cefixime, cefmetazole, cefoperazone, cefotaxime, cefotaxime sodium, cefotetan, cefoxitin, cefoxitin sodium, cefpodoxime proxetil, cefprozil, ceftazidime, ceftazidime sodium, ceftriaxone, ceftriaxone sodium, cefuroxime, cefuroxime axetil, cefuroxime sodium, celecoxib, cell therapy, cellular implant therapy, cephacetrile, cephalexin, cephaloglycin, cephaloridine, cephalosporin c, cephalosporins, cephalotin, cephamycin a, cephamycin b, cephamycin c, cephamycins, cepharin, cephradine, cere-110, cere-120, cerebro, ceredase, ceretec, cericlamine, certolizumab pegol, ceti-1 vaccine, cetrizine, cetrorelix, cetuximab, cevimeline hcl, cevimeline hcl, chimeric mab, chimeric monoclonal antibody, chimeric tumor-necrosis therapy (tnt), chimeric-anti-interleukin-6 monoclonal antibody, chir-12.12, chloralbetaine, chlorambucil, chloramphenicol, chloramphenicol sodium succinate, chlordiazepoxide, chlorhexidine gluconate, chlorobutinpenicillin, chloromycetin, chloroprocaine, chloroprocaine hydrochloride, chloroquine phosphate, chlorothiazide, chlorothiazide sodium, chloroxine, chlorpheniramine, chlorpheniramine; hydrocodone, chlorpromazine, chlorpromazine hydrochloride, chlorpromazine hydrochloride intensol, chlorpropamide, chlorprothixene, chlorthalidone, chlorthiazide; reserpine, chlorzoxazone, cholecystokinin, cholest-4-en-3-one, oxime, cholestyramine, cholic acid, choline, choriogonadotropin alfa, chorionic gonadotropin, chromic chloride, chromic phosphate p32, chromitope sodium, ciclesonide, ciclopirox, ciclopirox olamine, ciclopirilax, ciclosporin, cidofovir, cilazaprol, cilengitide, cilostazol, cimetidine, cimetidine hydrochloride, cinacalcet, cinchophen, cinmetacin, cinnarizine, cipramadol, ciprofloxacin, ciprofloxacin hydrochloride, ciprofloxacin; dexamtheasone, cisatracurium besylate, cis-mdp, cisplatin, cisplatin/5-fu therapy, citalopram, citalopram hydrobromide, cladribine, clarithromycin, clebopride, clemastine, clemastine fumarate, clindamycin hydrochloride, clindamycin injection, usp, clindamycin phosphate, clindamycin; benzoyl peroxide, clioquinol, clioquinol; hydrocortisone, clobenzepam, clobetasol, clobetasol propionate, clocapramine, clocortolone pivalate, clofarabine, clofibrate, cloinacran, clometacin, clometocillin, clomiphene citrate, clomipramine, clomipramine hydrochloride, clonazepam, clonidine, clonidine hydrochloride, clonidine; chlorthalidone, clonitazene, clonixin, clopenthixol, clopidogrel, clopriac, clorazepate dipotassium, clospirazine, clothiapine, clotrimazole, clotrimazole; betamethasone, clovoxamine, cloxacillin, cloxacillin sodium, clozapine, cmc-544, cmd-193, cnto 1275, cnto 328, co bicalutamide, co cilazapril, co fluconazole, co fosinopril, co ipra-sal, co risperidone, co salbut-iprat inhalation solution, co topiramate, cobalt chloride, codeine, codeine phosphate, codeine; chlorpheniramine, colchicines; probenicid, colesevelam hcl, colestipol hcl, colfosceril palmitate, colistimethate, colistimethate sodium, collagenase, compazine, conivaptan hydrochloride, copper, corticorelin ovine triflutate, corticotropin, corticotropin-releasing hormone, cortisone acetate, co-sertraline, cotinine, cp-547,632, cp-751,871, cpg 7909, cr0002, crisantaspase, cromolyn sodium, cromolyn sulfate, crotamiton, cs 1008, ctg cca cgt tct cct gc-, cupric chloride, cyamemazine, cyanocobalamin, cyclacillin, cyclizine, cyclobenzaprine, cyclobenzaprine hydrochloride, cyclopentolate hydrochloride, cyclopentolate; phenylephrine, cyclophosphamide, cyclosporin, cyclosporin a, cyclosporine, cyproheptadine, cyproheptadine hydrochloride, cysteinyl leukotrienes, cytarabine, cytomegalovirus immune globulin (cmv-igiv), dacarbazine, daclizumab, dactinomycin, dalteparin sodium, danazol, dantrolene sodium, dapsone, daptomycin, darbepoetin alpha, darifenacin hcl, darunavir, dasatinib, daunorubicin citrate, daunorubicin hydrochloride (plus liposomal), ddavp, decitabine, deferiprone, deferoxamine mesylate, defibrotide, dehydroepiandrosterone, delavirdine mesylate, demeclocycline hydrochloride, dendritic cell vaccine, denileukin diftitox, denosumab, denufosol tetrasodium, deoxygalactonojirimycin hydrochloride, deoxyribose phosphorothioate, deprenyl, desflurane, desipramine, desipramine hydrochloride, desirudin, desirudin recombinant, desloratadine, *Desmodus rotundus* salivary plasminogen activator (dspa), desmopressin acetate, desogestrel, desogestrel; ethinyl estradiol, desonide, desoximetasone, deuterium oxide, dexamethasone, dexamethasone intensol, dexamethasone sodium phosphate, dexchlorpheniramine maleate, dexfenfluramine, dexmedetomidine, dexmethylphenidate hcl, dexrazoxane, dexrazoxane hydrochloride, dextramethorphan; guafenisin; pseudophedrine, dextroamphetamine, dextroamphetamine saccharate, dextroamphetamine sulfate, dextromethorphan, dextromoramide, dextropropoxyphene, dextrose, dextrose dialysis solution, diaminopyridine phosphate, diamorphine, diatrizoate meglumine, diatrizoate sodium, diazepam, diazoxide, dibenzyline, dibotermin alpha, diclofenac, diclofenac; misoprostol, dicloxacillin, dicloxacillin sodium, dicyclomine hydrochloride, didanosine, diethylpropion, difenoxin; atropine, diflorasone diacetate, diflunisal, digoxin, dihydrocodeine, dihydroergokryptine, dihydroergotamine, dihydroergotamine mesylate, diltiazem, diltiazem hydrochloride, dimenhydrinate, dimercaprol, dimethyl sulfoxide, dimethylphenidate, dinaprostone, dinoprostone, diphenhydramine, diphenhydramine hydrochloride, diphenicillin, diphenidol, diphenoxylate, diphenoxylate; atropine, diphenylcyclopropenone, diphtheria/tetanus/pertussis/hepatitis b vaccine, diphtheria/tetanus/pertussis/hepatitis b/poliomylelitis vaccine, diphylline, dipipanone, dipivefrin hydrochloride, diptheria/tetanus/hepatitis b/poliomyelitis/hib/perutssis vaccine, dipyridamole, disopyramide phosphate, disulfiram, dmsa, dna nanoparticle gene therapy, dna vaccine, dnase, dobutamine hydrochloride, docetaxel, docosahexaenoic acid, docosanol, dofetilide, dolasetron mesylate monohydrate, dolasetronmethanesulfonate, dolophine hydrochloride, domalendronate, dom-alendronate, dom-anagrelide, dom-bicalutamide, dom-citalopram, dom-doxycycline, domeridone, dom-hydrochlorothiazide, dom-mirtazapine, dom-ondanssetron, dom-risperidone, dom-simvastatin, dom-ursodiol c, donepezil, dopamine, dopamine hydrochloride, dornase alfa, dorzolamide, dorzolamide; timolol, dosulepin, doxacalciferol, doxapram hydrochloride, doxazosin mesylate, doxepin, doxepin hydrochloride, doxorubicin, doxorubicin carbon/iron, doxorubicin hydrochloride, doxorubicin polyisohexylcyanoacrylate nanoparticles, doxycycline, doxycycline hyclate, doxylamine, doxylamine succinate, dronabinol, droperidol, droprenilamin hcl, drospirenone; estradiol, drosporenone; ethinyl estradiol, drotrecogin alpha, dtp vaccine, dtpa, duloxetine, duramycin, dutasteride, dx-88, dx-890, dyphylline, *E. coli* heat-shock protein 70 with bovine retinal s-antigen, e.e.s. erythromycin, ethylsuccinate, econazole nitrate, ecromeximab, ecteinascidin 743, eculizumab, edetate calcium disodium, edetate disodium, edrophonium chloride, efalizumab, efavirenz, eflornithine, egen-001, electrolyte irrigation solution, eletriptan, eliprodil, emd 273063, emedastine difumarate, emtricitabine, enalapril, enalapril maleate, enalapril maleate; felodipine, enalapril; diltiazem, enalaprilat, encirazine, endrophonium chloride, enflurane, enfuvirtide, engineered protein inhibitor of human neutrophil elastase, enoxaparin sodium, entacapone, entecavir, enzastaurin hydrochloride, ephedrine, epinastine hcl, epinephrine, epinephrine, epirubicin hydrochloride, eplerenone, epoetin alfa, epo-fc, epoprostenol sodium, epothilone b, eprosartan, epstein-barr virus vaccine, eptacog alfa, eptastigmine, eptifibatide, eptotermin alpha, ergocalciferol, ergolinepramipexole, ergoloid mesylates, ergotamine, ergotamine tartrate, ergotamine; caffeine, erlotinib, ertapenem sodium, erythrocin stearate, erythromycin, erythromycin base, erythromycin estolate, erythromycin ethylsuccinate, erythromycin lactobionate, erythromycin stearate, erythromycin; sulfisoxazole, erythropoietin, erythropoietin b, escitalopram, escitalopram oxalate, esmolol hydrochloride, esomeprazole sodium, estazolam, estradiol, estradiol acetate, estradiol cypionate, estradiol hemihydrate and progesterone, estradiol valerate, estradiol; norethindrone, estramustine phosphate, estriol, estrogen; progesterone, estrogens, conjugated, estrogens; medroxyprogesterone, estrone, estropipate, eszopiclone, etamiphyllin, etanercept, etaqualone, ethacrynate sodium, ethacrynic acid, ethambutol, ethambutol hydrochloride, ethanol, ethanolamine oleate, ethiinyl estradiol; ethynadiol acetate, ethinyl estradil; levonorgestrel, ethinyl estradiol, ethinyl estradiol; norethindrone, ethinyl estradiol; levonorgestrel, ethinylestradiol; levonorgestrel, ethiodized oil, ethionamide, ethoheptazine, ethosuximide, ethotoin, ethyl eicosopentaenoate, ethynylcytidine, eti-201, etidronate disodium, etilefrin, etodolac, etoposide, etoposide phosphate, eu/3/04/247, exemestane, exenatide lar, exenatide synthetic, extended phenytoin sodium, ezetimibe, factor ix complex (konyne 80, profilnine heat-treated, proplex sx-t, proplex-t), factor vii, factor viii, factor xi, famciclovir, famotidine, felbamate, felodipine, fenfluramine, fenofibrate, fenoldopam mesylate, fenoprofen calcium, fentanyl, fentanyl citrate, ferumoxides, ferumoxsil, fexofenadine, fexofenadine hydrochloride, fgf-1, fgf-5 peptides, fibrin sealant, flbroblast growth factor 1, fientanyl, filgrastim, finasteride, flavoxate hydrochloride, flecainide acetate, flesinoxan, floxuridine, fluconazole, flucytosine, fludarabine phosphate, fludeoxyglucose, fludeoxyglucose f-18, fludrocortisone acetate, flumazenil, flunisolide, fluocinolone acetonide, fluocinolone; tetrinoin; hydroquinone, fluocinonide, fluoromethalone acetate, fluorometholone, fluorouracil, fluoxetine, fluoxetine hydrochloride, fluoxymesterone, flupenthixol, fluphenazine, fluphenazine decanoate, fluphenazine hydrochloride, flupirtine, flurandrenolide, flurazepam, flurazepam hydrochloride, flurbiprofen, flurbiprofen sodium, fluspirilene, flutamide, fluticasone propionate, fluvastatin, fluvoxamine, fluvoxamine maleate, folic acid, follicle-stimulating hormone, follitropin alfa/beta, fomepizole, fondaparinux sodium, formivirsen, formoterol fumarate, fosamprenavir, fosamprenavir calcium, foscavir, fosfomycin; tromethamine, fosinopril, fosinopril sodium, fosphenytoin sodium, frovatriptan, fulvestrant, fumagillin, furosemide, g17(9) gastrin-diphtheria toxoid conjugate, gabapentin, gadobenate dimeglumine, gadodiamide, gadopentetate dimeglumine, gadoteridol, gadoversetamide, ga-gcb, galanthamine, gallium citrate ga 67, gallium nitrate, galsulfase, gamunex, ganciclovir, ganciclovir sodium, ganirelix acetate, garamycin, gastrin, gatifloxacin, gefitinib, gemcitabine hydrochloride, gemfibrozil, gemifloxacin mesylate, gemtuzumab ozofamicin, gene therapy, gentamicin, gentamicin sulfate, gepirone, ghrelin, gimatecan, g-interferon, glatiramer acetate, gliatak, gliclazide, glimepiride, glimepiride, glipizide, glipizide; mefformin, glucagon, glucocorticoids, glutathione, glyburide, glyburide; metfonnin, glyceryl trinitrate, glycine, glycopyrrolate, gm-csf, gmk, golimumab, gonadotropic, chorionic, gonadotropin-releasing hormone, goserelin acetate, gramicidin; neomycin; polymyxin b sulfate, granisetron, granisetron hydrochloride, griseofulvin, group c meningococcal conjugate vaccine, growth hormone, gti 2040, guaifenesin, guaifenesin; pseuodoephedrine, guanabenz acetate, guanfacine hydrochloride, guanidine hydrochloride, gusperimus trihydrochloride, gvak (leukemia, pancreatic, prostate), *H. pylori* urease breathe test, halcinonide, halobetasol propionate, halofuginone hydrobromide, haloperidol, haloperidol decanoate, haloperidol lactate, haloperidole, halothane, hctz; irbesartan, hctz; olmesartan, hctz; quinipril, hctz; spironolactone, heliox, heparin sodium, hepatitis a & b vaccine, hepatitis a vaccine inactivated, hepatitis b immune globulin, hepatitis b vaccine, hepatitis c immunoglobulin, hepatocyte growth factor gene therapy, heptylpenicillin, herpes dna vaccine, herpes simplex virus, hetacillin, hexachlorocyclohexane, hexachlorophene, hexavalent vaccine, hgs-etr1/hgs-etr2, hgs-tr2j, hgtv43 gene medicine, hib vaccine, hib; *neisseria* mening; hep b antigen vaccine, histamine dihydrochloride, histrelin, hiv dna vaccine, hiv recombinant vaccine, hla-b27 derived peptide, homatroprine methylbromide, homoharringtonine, homoharringtonine, hrecombinant atiii, h-tyrosine-glycine-phenylalanine-glycine-glycine-oh, huc242-dm4, human alpha1-proteinase inhibitor, human chorionic gonadotropin, human cytomegalovirus immunoglobulin, human hpv vaccine, human immunoglobulin, human interleukin-2, human liver cell therapy, human menopausal gonadotropin, human monoclonal antibody, human monoclonal antibody ab88bv59, human monoclonal antibody against hla-dr, human monoclonal hepatitis b immunoglobulins, human normal immunoglobulin (ivig, human placental lactogen, human *Staphylococcus aureus* immunoglobulin, human telomerase reverse transcriptase peptide, humanized agonistic anti-cd28 monoclonal antibody, humax-cd20, humax-cd4, humax-egfr, hun901-dm1, huzaf, hyaluronidase, hydralazine hydrochloride, hydralazine; hctz, hydralazine; hydrochlorothiazide, hydralazine; isdn, hydrazine, hydrochlorothiazide, hydrocodone bitartrate, hydrocodone; acetaminophen, hydrocodone; homatropine, hydrocodone; ibuprofen, hydrocortisone, hydrocortisone sodium succinate, hydrocortisone valerate, hydrocortisone; neomycin; polymixin b, hydrocortisone; pramoxine, hydroflumethiazide, hydrogenated ergot alkaloids, hydromorphone, hydromorphone hydrochloride, hydroxocobalamin, hydroxyamphetamine; tropicamide, hydroxychloroquine sulfate, hydroxyethyl starch, hydroxypropyl cellulose, hydroxyurea, hydroxyzine, hydroxyzine hydrochloride, hydroxyzine pamoate, hyoscine, ibandronic acid, ibuprofen, ibuprofen; pseudoephedrine, ibutilide fumarate, icatibant acetate, icodextrin, idarubicin hydrochloride, idazoxan, idebenone, idoxuridine, iduronate-2-sulfatase, idursulfase, ifosfamide, ign101, ign311, il 13-pe38qqr, il-1r, il-2, il-2/ep, il-21, il-4r, iloprost, ima-638, imatinib, imatinib mesilate, imatinib mesylate, imc-3g3/imc-11f8/imc-18f1/imc-1121b/imc-a12, imexon, imiglucerase, imipramine, imipramine hydrochloride, imiquimod, immu-100/immu-101/immu-102/immu-105/immu-106/immu-107, immune globulin, inactivated hepatitis a virus; hepatitis b surface antigen suspension, inactivated hepatitis b vaccine, inactivated polio virus vaccine, inactivated rabies virus vaccine, inamrinone lactate, indapamide, indicolor, indinavir, indium dtpa in 111, indium in 111 chloride, indium in 111 oxyquinoline, indium in 111 pentetate disodium, indium in 111 pentetreotide, indocyanine green, indomethacin, indomethacin sodium, indoprofen, infliximab, ing 1, ingap peptide, ingn 225/ingn 234/ingn 241/ingn 401, inhibin, inn-carglumic acid, inn-ivabradine, inno 102, inno-105/inno-305/inno-406, inn-protein c, inolimomab, ins37217, insulin (r dna origin), insulin (recombinant human), insulin aspart, insulin aspart recombinant, insulin detemir recombinant, insulin glargine recombinant, insulin glusine, insulin lispro protamine recombinant, insulin purified pork, insulin zinc, insulin-like growth factor, interferon alfa-2a, interferon alfason-1, interferon alpha, interferon beta, interferon beta 1-b, interferon beta gene delivery, interferon beta-1a, interferon gamma, interferon gamma-1b, interferon omega, interleukin-1 trap, interleukin-3/interleukin-12, intravenous immune globulin, iobenguane sulfate i 131, iodinated 125 albumin, iodinated 131 albumin, iodine, iodipamide meglumine, iodixanol, iodo-1-phenylalanine, iohexol, iopamidol, iothalamate meglumine, iothalamate sodium, ioversol, ioxaglate meglumine, ioxaglate sodium, ipilimuinab, ipratropium bromide, iproniazid, ipsapirone, ir103 w/amplivax, irbesartan, irbesartan; hctz, irbesartan; hydrochlorothiazide, irinotecan hydrochloride, iron dextran, iron sucrose, isf 154, isis 113715, isis 301012, isocarboxazid, isoetharine hydrochloride, isoflurane, isoleucine, isometheptene, isoniazid, isophane insulin, isoproterenol, isoproterenol bitartrate, isoproterenol hydrochloride, isosorbide dinitrate, isosorbide mononitrate, isosulfan blue, isotonic gentamicin sulfate, isotretinoin, isradipine, itraconazole, iv fat emulsion, iv lipids, ivabradine, ivermectin, kanamycin, kanamycin sulfate, ketamine, ketamine hydrochloride, ketoconazole, ketoprofen, ketorolac, ketorolac tromethamine, ketotifen, kitanserin, kl-4 peptide+lipid, kos-862/kos-953 kp-1461, labetalol hydrochloride, lactated ringer's, lactoferin, lactulose, l-alphaacetylmethadol, lamivudine, lamivudine; zidovudine, lamotrigine, lanreotide, lansoprazole, lanthanum carbonate, laronidase, l-asparaginase, latanoprost, lazabemide, leflunomide, lenalidomide, lentiviral vector, lep-etu/lep-sn38, lepirudin recombinant, leptin, lerafaon-etu, lesopitron, lestaurtinib, letrozole, leucovorin calcium, leuprolide, leuprolide acetate, levalbuterol hydrochloride, levamisol hydrochloride, levetiracetam, levobunolol hydrochloride, levocabastine, levocarnitine, levodopa, levodopa and carbidopa, levodopa; carbodpa, levofloxacin, levonorgestrel, levorphan tartrate, levorphanol, levorphanol tartrate, levothyroxine sodium, liarozole, lidocaine, lidocaine hydrochloride, lidocaine; prilocaine, lidocaine; tetracaine, lignocaine; polymyxin b sulfate, lincomycin hydrochloride, linezolid, liothyronine sodium, liposomal doxorubicin, liposomal morphine, liraglutide, lisinopril, lisinopril; hctz, lisuride, lithium carbonate, lithium citrate, live, attenuated typhoid vaccine, l-lysine-n-acetyl-l-cysteinate, Iodine, lodoxamide tromethamine, lofentanil, lofepramine, lomefloxacin hcl, lomustine, loperamide hydrochloride, lopinovir; ritonavir, loprazolam, loracarbef, loratidine, lorazepam, losartan; hctz, losartan; hydrochlorothiazide, loteprednol, loteprednol etabonate, lovastatin, lovastatin; niacin, loxaglate sodium, loxapine, loxapine succinate, loxilan, lumigan; timolol, lumiracoxib, lusupultide, luteinizing hormone, ly 2181308, ly2275796, lymphostat-b, lysine acetate, m m r vax ii injection, m.t.e.-4/m.t.e-6, m195-bismuth 213 conjugate, m200, mab heft-1, mafenide acetate, mage-3, magnesium chloride, magnesium sulfate, malathion, mangafodinir trisodium, manganese chloride, mannitol, mannitolum, maprotiline hydrochloride, maprotoline, mart-1 melanoma vaccine, matuzumab, mazipredone, mdx-060, mdx-066, mdx-070, mdx-1100, mdx-1303, mdx-214, measles mumps rubella vaccine, measles mumps vaccine, mebendazole, mebrofenin, mecamylamine hcl, mecasermin, mecasermin recombinant, mecasermin rinfabate, mecasermin rinfabate recombinant, mechlorethamine hydrochloride, meclizine hydrochloride, meclofenamate, meclofenamate sodium, mecloqualone, medetomidine, medi-507 siplizumab, medi-522, medi-528 anti-il-9 mab, medi-534 rsv/piv-3 vaccine, medi-545, medifoxamine, medroxyprogesterone acetate, mefenamic acid, mefloquine, mefloquine hydrochloride, megestrol acetate, melanocyte-stimulating hormone, melatonin, melonom tumor-reactive autologous til, meloxicam, melperone, melphalan hydrochloride, memantine, meningococcal group c vaccine, meningococcal polysaccharide vaccine, menotropins, menthol, mepenzolate, meperidine, meperidine hcl, meperidine hydrochloride, mepivacaine hydrochloride, mepivicaine; levonordefrin, mepolizumab, meprobamate, meptazinol, mequinol; tretinoin, mercaptamine bitartrate, mercaptopurine, meropenem, mesalamine, mesalamine; 5-asa, mesna, mesoridazine, metampicillin, metaproterenol, metaproterenol sulfate, metaraminol bitartrate, metastable technetium 99 demogastrin 2, metaxalone, metformin, metformin hydrochloride, metfonnin; pioglitazone, metformin; rosiglitazone, methacholine chloride, methadone hydrochloride, methamphetamine hcl, methaqualone, methazolamide, methenamine hippurate, methenamine mandelate, methicillin, methimazole, methocarbamol, methohexital sodium, methotrexate, methotrexate sodium, methotrimeprazine, methoxsalen, methprylon, methscopolamine, methsuximide, methyclothiazide, methyl aminolevukinate, methyldopa, methyidopa; hctz, methyldopate hydrochloride, methylenetetrahydrofolate, methylene-tetrahydrofolic acid, methylergonovine maleate, methylphenidate, methylphenidate hydrochloride, methyl-phosphorothioate oligonucleotide, methylprednisolone, methylprednisolone acetate, methylprednisolone sodium succinate, methyltestosterone, methyphenidate, methyprylon, methysergide, metipranolol, metoclopramide, metoclopramide hydrochloride, metofenazate, metolazone, metomidate, metopimazine, metopon, metoprolol, metoprolol tartrate, metralindole, metronidazole, metronidazole; nystatin, metyrapone, metyrosine, mexiletine hydrochloride, mg98, mianserin, micafungin sodium, miconazole, micophenolic acid, micro+4/micro+5/micro+6/micro cr/micro cu/micro i/micro mn/micro se, midazolam, midazolam hydrochloride, midodrine hydrochloride, midostaurin, mifepristone, miglitol, miglustat, milnacipran, milrinone lactate, miltefosine, minaprine, minocycline, minocycline hydrochloride, minoxidil, mirtazapine, misoprostol, mitomycin, mitotane, mitoxantrone, mitoxantrone hydrochloride, mivacurium chloride, min 1202, min-02, mm-093, mmr; chicken pox vaccine, moclobemide, modafinil, moexipril hcl; hydrochlorothiazide, moexipril hydrochloride, mofegiline, molindone hcl, mometasone furoate, monobenzone, monoclonal antibody to human interleukin-6, monocyte-derived activated killer (mak) cells, montelukast sodium, morab 003, morab 009, moricizine, morphine, morphine sulfate, mosquirix malaria vaccine, moxifloxacin hydrochloride, mpi dmsa kidney reagent, mpi dtpa kit-chelate, mpi indium dtpa in 111, multi-11/multi-12, multivitamin infusion, mumps vaccine, mupirocin, muramyl tripeptide phosphatidyl ethanolamine, murine anti-idiotypic antibody against oc125 antibody against ca125 antigen, murine monoclonal antibody mab ar 20.5, muromonab-cd3, m-vax, mycophenolate mofetil hydrochloride, myeloma-derived idiotypic antigen vaccine, yo-029, myristoylated-peptidyl-, nabilone, nabumetone, n-acetylgalactosamine-4-sulfatase, n-acetylsarcosyl-glycyl-l-valyl-d-allo-isoleucyl-l-threonyl-l-norvalyl-l-isoleucyl-l-arginyl-l-prolyl-n-ethylamide, nadolol, nadrolone decanoate, nadroparin, nafcillin, nafcillin sodium, naftifine, nalbuphine, nalbuphine hydrochloride, nalidixic acid, nalmefene, nalmefene hydrochloride, nalorphine, naloxone, naloxone hydrochloride, naltrexone, naltrexone hydrochloride, nandrolone decanoate, nanopeptide paclitaxel, naphazoline hydrochloride, naphazoline; antazoline, naphazoline; pheniramin, naproxen, naproxen sodium, naratriptan, natalizumab, natamycin, natarelin acetate, nateglinide, n-azaphenyl-aminothiopyrrole, nbi-5788, nbi-6024, n-carbamyl-l-glutamic acid, nedocromil sodium, nefazodone, nefazodone hydrochloride, nefopam, nelarabine, nelfinavir, nemorubicin hydrochloride, neomycin neomycin sulfate, nepafenac, nesiritide recombinant, neuradiab, neuropeptide y, nevirapine, niacin, nicardipine hydrochloride, nicergoline, nicotine, nicotine polacrilex, nifedipine, nilotinib, nilutamide, nimoripine, nimotuzumab, nisoldipine, nisoxetine, nitazoxamide, nitisinone, nitisinone, nitrofurantoin, nitrofurazone, nitroglycerin, nitrous oxide, nitrous oxide; oxygen (50:50), nizatidine, nix p101, nm01, nofetumomab, nomifensine, noradrenaline, norepinephrine bitartrate, norethindrone, norethindrone acetate, norfloxacin, norgestrel; ethinyl estradiol, norlegestromin; ethinyl estradiol, nortriptyline, nortriptyline hydrochloride, nt501 ciliary neurotrophic factor, nystatin, nystatin; triamcinolone, obestatin, ocrelizumab, octreotide acetate, ofloxacin, ogx-011, okt3-gamma-1, olanzapine, oligonucleotide phosphorothioate, olopatadine hydrochloride, olsalazine sodium, omalizumab, omega 3 and ethyl esters, omeprazole, omoconazole, ondansetron, ondansetron hydrochloride, ondansetron hydrochloride dihydrate, ondansetron omega, opebacan, opium tincture, oprelvekin, oral cholera vaccine, oral recombinant human growth hormone, oral recombinant parathyroid hormone 1-34, oregovomab, orlistat, orphenadrine, orphenadrine citrate, orphendrine; aspirin; caffeine, oseltamivir phosphate, osteogenic protein-1 i, oxacillin sodium, oxaliplatin, oxalobacter formigenes strain hc-1, oxandrolone, oxaprozin, oxazepam, oxcarbazepine, oxiconazole, oxo-pentanoic acid methyl ester, oxprenolol, oxtriphylline, oxybutynin chloride, oxybutynin nicobrand, oxycodone, oxycodone, oxycodone; acetaminophen, oxycodone; apap, oxycodone; ibuprofen, oxymetazoline, oxymethalone, oxymorphone hydrochloride, oxytetracycline, oxytocin, p501, p53 and ras vaccine, paclitaxel, palifermin, palivizumab, palonosetron, palonosetron hydrochloride, paloxitene hcl, pam 4, pamelteon, pamidronate disodium, pancreatic enzymes, pancuronium, pancuronium bromide, pantoprazole sodium, papaveretum, papaverine, papiprazole, paracoxib, paracoxib sodium, parathyroid hormone, parecoxib sodium, paricalcitol, paromomycin sulfate, paroxetine, paroxetine hydrochloride, paroxetine mesylate, paxene, pazopanib, pazopanib hydrochloride, pbl and til transduced with retroviral vector-expressing anti-gp100 tcr, pbl or til transduced with retroviral vector-expressing anti-mart-1 tcr gene, pediazole, pegademase bovine, pegaptanib sodium, pegaspargase, peg-filgrastim, peginterferon alfa-2a, peginterferon alpha 2b, pegvisomant, pegylated arginine deiminase, pemetrexed disodium, pemirolast, pemoline, penbutolol, penciclovir, penfluridol, penicillamine, penicillin, penicillin g, penicillin n, penicillin o, penicillin s, penicillin v, pentamidine isethionate, pentazocine, pentazocine hydrochloride, pentazocine lactate, pentazocine; acetaminophen, pentetate calcium trisodium, pentetate zinc trisodium, pentobarbital, pentobarbital sodium, pentosan polysulfate sodium, pentostatin, pentoxifylline, peptide 144 tgf-beta1-inhibitor, peptides, perflutren, perflutren protein-type a microspheres, pergolide mesylate, pericyazine, perindopril, perindopril, permethrin, perphenazine, persantine, personalized anti-cancer vaccine, pethidine, pexelizumab, pg-cpt, phenazocine, phendimetrazine tartrate, phenelzine, phenobarbital, phentermine, phentermine hydrochloride, phentolamine, phentolamine mesylate, phentytoin, phenyhydrazine, phenylephrine hydrochloride, phenytoin, phenytoin sodium, phosphodiesterase-5 inhibitor, phospholine iodide, php, php pyridoxalated hemoglobin polyoxyethylene, physiologic saline solution, pilocarpine, pilocarpine hydrochloride, pimecrolimus, pimozide, pindolol, pioglitazone, pipamerone, piperacetazine, piperacillin, piperacillin sodium, piperacillin sodium/tazobactam sodium, pipotiazine, pirbuterol acetate, pirbuterolnaloxone, pirfenidone, piroxicam, pirprofen, pizotifen, plicamycin, pneumococcal vaccine polyvalent, pnu-166196, podofilox, polyeptides, polyethylene glycol, polyhematoporphyrin, polymyxin b sulfate, polypeptide yy, polysaccharide diphtheria toxoid conjugate vaccine, polythiazide, poractant alpha, porfimer sodium, posaconazole, potassium acetate, potassium chloride, potassium citrate, potassium iodide, povidone iodine, ppy 3-36, pralidoxime chloride, pramipexole, pramlintide acetate, pramoxine; hydrocortisone, prasterone, pravastatin, praziquantel, prazosin, prazosin; polythiazide, prednicarbate, prednisolone, prednisolone acetate, prednisolone sodium phosphate, prednisolone; gentamicin, prednisone, pregabalin, prentoxapylline, prilocaine, primaquine, primidone, pro 140, probenecid, probucol, procainamide hydrochloride, procaine, procaine hydrochloride, procarbazine, procaterol hcl, prochlorperazine, prochlorperazine edisylate, prochlorperazine maleate, procyclidine, progesterone, prolactin, prolifeprosan 20; carmustine, promazine, promethazine, promethazine hydrochloride, propacetamol, propafenone hydrochloride, propanedisulfonic acid, disodium salt, propanolol, propantheline bromide, proparacaine hydrochloride, propentofylline, propofol, propoxyphene, propoxyphene; acetaminophen, propranolol, propranolol hydrochloride, propylpiperidine x hcl, propylthiouracil, proscar, proscillaridin; verapamil, prosol, prostcyclin, protamine sulfate, proteinase 3 peptide vaccine, proteins, protriptyline, provocholine, prussian blue, psa: 154-163, pseudoephedrine hydrochloride, *pseudomonas* exotoxin-interleukin 13 chimeric protein, pseudophedrine; triprolidine, psma, pth 1-34, pulmonary surfactant, purified bromelain, purified inactivated japanese encephalitis sa14-4-2 virus vaccine, pyrazinamide, pyrethrin; piperinyl butoxide, pyridostigmine bromide, pyridoxine hydrochloride, pyrimethamine, quadravalent hpv vaccine, quazepam, quetiapine, quinapril, quinapril hydrochloride, quinapril; hctz, quinidine gluconate, quinidine sulfate, quinine, r1550, r744 cera, rabaprazole, rabies immune globulin, radiotheracim, raloxifene, ramipril, ramoplanin, ranibizumab, ranitidine, ranitidine hydrochloride, ranpirnase, rasagiline, rasburicase, rav 12, rdna hepatitis b vaccine, reboxetine, recombinant antibody derivative, recombinant dog gastric lipase, recombinant fusion protein, recombinant glycoprotein gp350 of epstein-barr virus, recombinant hepatitis b vaccine, recombinant histidine-tagged idiotype immunoglobulin fab fragment of clonal b-cell receptors, recombinant human acid alpha-glucosidase, recombinant human acid sphingomyelinase, recombinant human alpha-1-antitrypsin, recombinant human alpha-mannosidase, recombinant human arylsulfatase a, recombinant human bile salt-stimulated lipase, recombinant human cl-inhibitor, recombinant human factor xiii, recombinant human glucagon-like peptide, recombinant human insulin-like growth factor-i/recombinant human insulin-like growth factor binding protein-3, recombinant human interleukin-21, recombinant human monoclonal antibody to hsp90, recombinant human porphobilinogen deaminase, recombinant inhibitor of human plasma kallikrein, recombinant megakaryopoeisis-stimulating protein, recombinant methionyl human stem cell factor, recombinant microbial lipase, recombinant modified vaccinia virus ankara expressing tuberculosis antigen 85a, recombinant neuraminidase, recombinant p-selectin glycoprotein immunoglobulin, recombinant triple antigen hepatitis b vaccine, remacemide, remifentanil, remifentanil hydrochloride, remoxipride, remune hiv-1 immunogen, renal tumor-reactive autologous til and pbl, repaglinide, repertaxin I-lysine salt, rescinnamine, reserpine, resonium calcium, resten-mp, resten-ng, reteplase, retinol, retinol binding protein 4, retroviral gamma-c cdna containing vector, rfx111, rhbmp-2, rhcc10, rhlgfbp-3, rhmb1, rho(d) immune globulin, rhthrombin, ribavirin, rifabutin, rifampicin, rifampin, rifampin; isoniazid, rifampin; pyrazinamide; isoniazid, rifapentine, rifaximin, riluzole, rimantadine hydrochloride, rimexolone, rimonabant, ringer's, risperidone, ritanserin, ritodrine, ritodrine hydrochloride, ritonavir, rituximab, rivastigmine, rivastigmine tartrate, rizatriptan, rn1219, rn624, rocuronium bromide, ropinirole hcl, ropivacaine, roseglitazone, rosiglitazone, rosiglitazone; glimepiride, rosuvastatin, rotigotine, roxindole, rpa102, rpe cells with microcarriers, rubella virus vaccine, live, rubidium chloride rb-82, rubitecan, rufinamide, rx 0201, S. pneumoniae recombinant vaccine, sabarubicin, sacrosidase, s-adenosylmethionine, salbutamol, salicylate, salmeterol xinafoate, salmetrol, samarium sm 153 lexidronam pentasodium, samarium sm-153, sapropterin, saquinavir, sargramostim, sbil-2 transduced autologous til, scopolamine, secobarbital sodium, secretin, secretin synthetic human, secretin synthetic porcine, sehcat, selegiline, selegiline hydrochloride, selenious acid, selenium sulfide, sermorelin acetate, seromycin, serotonin, sertaconazole, sertindole, sertraline, sestamibi miraluma, sevelamer, sevoflurane, sfg, sgn-00101, sgn-30, sgn-33, sgn-40, sibrotuzumab, sibutramine, sildenafil, sildenafil citrate, silver nitrate, simplirix, simvastatin, sinapultide, dipalmitoylphosphatidylcholine, palmitoyloleoylphosphatidylglycerol and palmitic acid, sincalide, siplizumab, sipuleucel-t, sirolimus, sitaxentan sodium, sitaxsentan, sipi, sodium acetate, sodium aminohippurate, sodium benzoate/sodium phenylacetate, sodium bicarbonatee, sodium butabarbital, sodium butyrate, sodium chloride, sodium chromate, sodium dichloroacetate, sodium edecrin, sodium eglinide, sodium ferric gluconate, sodium ferric gluconate complex, sodium fluoride, sodium gluconate, sodium iodide, sodium iodide i 131, sodium lactate, sodium nitroprusside, sodium oxybate, sodium p.a.s., sodium phenylbutyrate, sodium phosphate, sodium polystyrene sulfonate, sodium tetradecyl sulfate, sodium valproate, solifenacin, soluble yeast beta-1,3/1,6-glucan, somatostatin, somatropin, somatropin (r dna), somatropin recombinant, sorafenib, sorafenib tosylate, sorbitol, sotalol, sotalol hydrochloride, spc+lipid, spectinomycin hydrochloride, spiperone, spironolactone, sps: sodium polystyrene sulfonate, ss1(dsfv)-pe38, ssd: silver sulfadiazine, stavudine, sterile diluent, sterile provocholine solution, sterile vancomycin hydrochloride, stiripentol, streptokinase, streptomycin sulfate, streptozocin, strontium chloride sr-89, strontium ranelate, suberoylanilide hydroxamic acid, succimer, succinyicholine chloride, sucralfate, sufentanil, sufentanil citrate, sulconazole nitrate, sulfacetamide sodium, sulfacetamide; prednisone, sulfadiazine, sulfadoxine; pyrimthamine, sulfamethoprim, sulfamethoxazole/ trimethoprim, sulfasalazine, sulfentanil citrate, sulfinpyrazone, sulfisoxazole, sulindac, sulpiride, sumatriptan, sumatriptan succinate, sumitizib maleate, taci-Ig, tacrine, tacrolimus, tacrolimus hydrate, tadalafil, talc, tamoxifen citrate, tamsulosin hcl, tandospirone, tauferon, tazarotene, t-cell replacement therapy, technetium 99 monoclonal antibody, technetium fanolesomab, technetium tc 99m, technetium tc 99m tsc, technetium tc-99 generator, technetium tc-99m albumin, technetium tc-99m apcitide, technetium tc-99m bicisate, technetium tc-99m depreotide, technetium tc-99m disofenin, technetium tc-99m exametazime, technetium tc-99m gluceptate, technetium tc-99m mebrofenin, technetium tc-99m medronate, technetium tc-99m mertiatide, technetium tc-99m oxidronate, technetium tc-99m pentetate, technetium tc-99m pyrophosphate, technetium tc-99m red blood cell, technetium tc-99m sestamibi, technetium tc-99m succimer, technetium tc-99m sulfur colloid, technetium tc-99m tetrofosmin, teduglutide, tegaserod maleate, teicoplanin, telbivudine, telithromycin, telmisartan, telmisartan; hctz, telmisartan; hydrochlorothiazide, temazepam, temocillin sodium, temozolomide, temsirolimus, tenecteplase, teniparatide, teniposide, tenofovir, tenofovir; emtricitabine, terazosin hydrochloride, terbinafine, terbutaline, terbutaline sulfate, terconazole, terguride, teriparatide recombinant human, testalactone, testosterone, testosterone cypionate, testosterone enanthate, testosterone propionate, testosteroneacetate, testosteroneenanthate, testosteronepropionate, tetanus and diphtheria toxoid, tetanus and diphtheria toxoids adsorbed, tetanus immune globulin, tetanus toxoid, reduced diphtheria toxoid and acellular pertussis vaccine, tetraazacyclotetradecane, tetracycline hydrochloride, tetracycline; metronidazole; bismuth subsalicylate, tetrahydrobiopterin, tetrahydrocannabinol, tetrahydrozoline, tetrahydrozoline hcl, tg 1042, tg 4001, tg 4010, tgaac94, tgaav-cf, tgf-β2 specific phosphorothioate antisense oligodeoxynucleotide, thalidomide, thallium chloride, thallous chloride, thallous chloride t1-201, thc; cbp, theophylline, thiabendazole, thiamine hydrochloride, thiethylperazine, thioguanine, thioridazine, thioridazine hydrochloride, thiotepa, thiothixene, thiothixene hydrochloride, thrombin (human), thrombopoietin, thromboxane, thymalfasin, thyroid-stimulating hormone, thyrotropin (tsh), thyrotropin alfa, thyrotropin-releasing hormone, thyroxine, tiagabine, tianeptine, tiaprofenic acid, ticarcillin disodium, ticilimumab, ticlopidine hydrochloride, tifacogin, tigecycline, tilarginine acetate, tiludronate disodium, timolol, timolol maleate, tinidazole, tioconazole, tiopronin, tiotropium bromide monohydrate, tipifarnib, tipranavir, tirofiban hydrochloride, tissue repair cells, titanium dioxide and bisoctrizole, tizanidine, tizanidine hydrochloride, tnf alpha 1a, tnx-355, tnx-650, tnx-832, tobramycin, tobramycin sulfate, tobramycin; dexamethasone, tofenacin, tolazamide, tolbutamide, tolcapone, tolevamer, gt160-246, tolfenamate, tolfenamicacid, tohnetin sodium, tolterodine tartrate, topical vegf, topiramate, topotecan hydrochloride, toremifene citrate, torsemide, tositumomab, tp10, tpi-asm8, trabectedin, tradolapril; verapamil, trafermin, tramadol, tramadol; acetaminophen, trandolapril, tranexamic acid, tranylcypromine, trastuzumab, travoprost, travoprost; timolol, trazodone, trazodone hydrochloride, treosulfan, treprostinil, treprostinil sodium, tretinoin, triamcinolone acetoni de, triamcinolone hexacetonide, triamterene, triamterene; hydrochlorothiazide, triazolam, tricarbocyanine, tridesilon, trientine dihydrochloride, trientine hcl, triethylperazine, trifluoperazine, trifluoperazine hydrochloride, trifluperidol, triflupromazine, trifluridine, trihexyphenidyl, trihexyphenidyl hydrochloride, triiodothyronine, trimeprazine, trimethadione, trimethobenzamide, trimethobenzamide hydrochloride, trimethoprim, trimethoprim sulfate, trimethorprim sulfate; polymyxin b sulfate, trimetrexate glucuronate, trimipramine, triodothyronine, tripelennamine, triprolidine hydrochloride, triptorelin pamoate, troleandomycin, tromethamine, tropicamide, tropisetron, trospium chloride, troxacitabine, trx 1, trx 4, trypan blue, tryptophan, tuberculosis recombinant vaccine, tucotuzumab celmoleukin, tumor necrosis tumor necrosis, ty800 yphoid fever vaccine, tykerb lapatinib, tyrosine, unoprostone, urea, urofollitropin, urokinase, ursodiol, urtoxazumab, valacyclovir, valdecoxib, valganciclovir, val-leu-gin-glu-leu-asn-val-thr-val, valproate sodium, valproicacid, valrubicin, valsartan, vancomycin, vandetanib, vardenafil, varenicline, varicella zoster virus recombinant vaccine, vascular endothelial growth factor 2, vasoactive intestinal peptide, vectibix, vecuronium bromide, vegf trap, veglin, velafermin, veldon lozenges, venlafaxine, verapamil, verapamil hydrochloride, verteporfin, vigabatrin, viloxazine, vinblastine, vinblastine sulfate, vincristine sulfate, vinorelbine, vinorelbine tartrate, vip, vitamin a acid, vitamin a pahnitate, vitamin d, vitamin k, vitamin k1, voriconazole, vrc-hivadv 014-00-vp, vrx 496, vwf/fviii-concentrate, warfarin sodium, xaliproden hydrochloride, xenon, xtl 6865, y-fowlpox, r-vaccinia-tricorn vaccine, y-fowipox-cea(6d) tricom vaccine, y-fowlpox-gm-csf vaccine, y-fowlpox-psa vaccine, yohimbine, yttrium (90y) antiferritin polyclonal antibodies, yttrium (90y) chloride, yttrium (90y) chloride, zafirlukast, zalcitabine, zaledronic acid, zaleplon, zalospirone, zanamivir, ziconotide, zidovudine, zileuton, zinc acetate, zinc acetate dehydrate, zinc acetate dihydrate, zinc chloride, ziprasidone, ziprasidone mesylate, zoledronic acid, zolmitriptan, zolpidem, zonisamide, zopiclone, zoster vaccine, zosuquidar trihydrochloride, zotepine, zuclopenthixol, zyc 101a, zyc 300, and combinations thereof.

In some embodiments, the one or more active agents can be amniotic fluid, an amnion tissue preparation, or combinations thereof. In some embodiments, the one or more active agents can be a combination of two or more agents, wherein a first agent is selected from amniotic fluid, an amnion tissue preparation, or combinations thereof. In some embodiments, the one or more active agents can be a combination of two or more agents, wherein a first agent is selected from amniotic fluid, an amnion tissue preparation, or combinations thereof, and one or more additional agents selected from the active agents described herein. In some embodiments, the one or more active agents can be a combination of two or more agents, wherein a first agent is selected from amniotic fluid, an amnion tissue preparation, or combinations thereof, and a second agent selected from interferon beta, interferon beta 1-b, interferon beta gene delivery, interferon beta-1a, a BKB2R antagonist (e.g., icatibant), a KLKB1 inhibitor (e.g., ecallantide), androgens (e.g., danazol and stanasolol), recombinant SERPING1 (e.g., berinert, cinryze, haegarda), vitamin D, a HAS2 or HAS3 inhibitor (e.g., hymecromone (4-methylumbelliferone)), and timbetasin.

In some embodiments, the product substrate can include amniotic fluid ("AF").

AF is the fluid contained within the amniotic membrane, which forms a sac around the embryo and later fetus. AF, which is produced together by the fetus and the placenta, contacts the fetus, including the lung tissue, during the gestational period.

The composition of AF is, in some cases, not entirely known. However, AF can contain suspended amniocytes, stem cells, monocytes, macrophages, and histiocytes, as well as non-cellular components such as small molecules (including, but not limited to electrolytes, glutamine, arginine, and hyaluronic acid), growth factors (including, but not limited to, growth factor alpha ("TGF-α"), epidermal growth factor ("EGF"), insulin-like growth factor I ("IGF-1"), hyaluronic acid-stimulating factor, macrophage colony-stimulating factor ("M-CSF"), and granulocyte colony-stimulating factor ("G-CSF")), and hormones (including, but not limited to, erythropoietin). AF can also contain immunomodulators and antimicrobials, including α-defensins, lactoferrin, lysozyme, bactericidal/permeability-increasing proteins, calprotectin, secretory leukocyte protease inhibitor, psoriasin, a cathelizidin, and various polyamines with antimicrobial properties. AF can also contain additional compounds or components that can provide benefits to a subject. Without being bound by any particular theory, it is believed that delivery of AF to the lungs of a subject having a respiratory disorder, including delivery to the lung tissue of the subject, can provide multiple potential benefits. For example, in some cases, components such as glutamine can aid in localized nucleic acid synthesis in the subject, and can lead to tissue regeneration. In some cases, components such as arginine can aid in regenerative angiogenesis in the lung tissue. In some cases, components such as hyaluronic acid can mitigate or reduce scaring and fibrosis in the lungs, for example, by inhibiting collagen synthesis. In some cases, AF components such as growth factors can stimulate proliferation of stem cells and non-progenitor cell-types in the subject's cells and tissues, including the lungs. In some cases, AF components such as erythropoietin can promote proliferation of red blood cell progenitors and may stimulate growth of endothelial cells and tissue. In some cases, antimicrobial components of AF can aid in destroying, reducing, or inhibiting lung infections and microbial growth in the lungs. In some cases, inununomodulators contained in AF can stimulate, suppress, or otherwise modulate the subject's immune response, and in particular, the subject's immune response within the lungs and lung tissue.

In some embodiments, the AF can provide healing or regeneration of lung tissue. In some embodiments, the AF can provide modulation of mediation of immune responses within the lung or lung tissue, thus halting or preventing damage to lung tissue caused directly or indirectly by a subject's immune response. In some embodiments, deposition of AF in the lower respiratory tract can allow for deposition and absorption of beneficial components in AF. In some embodiments, at least a portion of the AF can be deposited along and absorbed along the bronchial tree as it travels toward the lower respiratory tract.

In some embodiments, the AF is human AF. However, in some embodiments, AF from other mammalian species may also be used. For example, AF can be used from species including, but not limited to horse, rabbit, lamb, cow, sheep, primates, and the like.

AF can be obtained by any method known in the art. For example, human AF can, in some embodiments, be obtained from humans who are undergoing amniocentesis, humans who are undergoing a Caesarean section delivery, humans undergoing vaginal delivery using a specially designed receptacle to collect the fluid after rupture of membranes, and the like. In some embodiments, AF can be collected under sterile conditions in the operating room during an elective Cesarean section delivery since this form of collection presents essentially no risk to the infant or the mother. Similar methods can be used to obtain AF from other species. In some embodiments, the AF is collected under sterile conditions. In some embodiments, the AF can be further processed to sterilize or otherwise alter the AF. For example, in some embodiments, the AF can be processed in a manner that destroys viable cells contained within the AF, producing AF that lacks viable cells. For example, AF can be obtained and then treated in a manner designed to lyse some or all of the cells within the AF. In some embodiments, unaltered AF may be used. In some embodiments, the AF can contain viable cells, non-viable cells, or a combination thereof. In some embodiments, the AF can be screened for disease agents and other contaminants after collection and before use in a subject as described herein. For example, the AF can be screened for disease agents such as SHIV, HTLV, Hepatitis B and C, syphilis, and the like. In some embodiments, an amnion tissue preparation can be sterile de-cellularized human anmiotic fluid, either in fluid form or solid form (e.g., lyophilized powder), alone or in combination with appropriate excipients. Some exemplary methods of preparing sterile de-cellularized amniotic fluid are described in detail in, e.g., U.S. application Ser. No. 15/053, 497, incorporated herein in its entirety.

In some embodiments, the AF is free of amniotic membrane or amniotic membrane particulate matter. For example, in some embodiments, the AF has been clarified or otherwise processed after collection to remove, for example, cellular debris from the amniotic membrane, but that retains macromolecules typically present in AF (e.g. proteins, lipids, nucleic acids, sugars, and the like). Standard techniques for removing particulate matter from biological samples can be used to remove the amniotic membrane particulate matter, including, but not limited to centrifugation (e.g. at a speed in the range of from about 1000 rpm to about 5000 rpm).

In some embodiments, the AF can be treated, to, e.g., provide preservation or lengthen shelf life, and the like. For example, in some embodiments, the AF can be treated by sterilization (e.g. by gamma-irradiation), or can be cooled by refrigeration or freezing. In some embodiments, substances may be added to the AF to, for example, prevent the growth of microbes (e.g. antifungal, antibacterial or antiviral agents). In some embodiments, the AF can be lyophilized (i.e. freeze-dried), stored, and then reconstituted for use as necessary. Standard lyophilization techniques can be used. In some embodiments, lyophilized AF can be reconstituted with, for example, physiologically compatible saline solutions. In some embodiments, the lyophilized AF can be reconstituted with AF, in circumstances where, for example, concentrated AF is desired. In some embodiments, the AF may can be concentrated by removal of water by any standard technique. For example, in some embodiments, essentially all water may be removed (e.g. by lyophilization). In some embodiments, the amount of water may simply be reduced (e.g. by vacuum filtration, etc.). In some embodiments, the AF is undiluted AF. In some embodiments, a diluted or concentrated form of AF can be used. For example, compositions can include a concentration of from about 10% to about 200% AF, from about 10% to about 95% AF, from about 10% to about 90% AF, from about 20% to about 80% AF, from about 30% to about 70% AF, from about 40% to about 60% AF, from about 100% to about 200% AF, from about 110% to about 200% AF, from about 120% to about 190% AF, from about 130% to about 180% AF, from about 140% to about 170% AF, about 50% AF, about 60% AF, about 70% AF, about 80% AF, about 90% AF, about 100% AF, about 110% AF, about 120% AF, about 130% AF, about 140% AF, about 150% AF, about 160% AF, about 170% AF, about 180% AF, about 190% AF, or about 200% AF in the composition. In the case of a liquid composition, the dilution may be made with any of several suitable diluents that are known to those of skill in the art, for example, physiologically compatible saline solution, balanced saline solution, sodium hyaluronate, methylcellulose, and the like.

In some embodiments, the product substrate can include an amnion tissue preparation. Placental tissue comprises two major membrane components, the amnion and the chorion. The amnion layer is interior to the chorion in relation to the amniotic sac that encloses a mammalian, e.g., human, embryo. An "amnion tissue preparation" as used herein refers to a preparation of amnion tissue or amnion material, e.g. from the amnion layer of the amniotic sac, a portion thereof, or any material including or derived from the amnion layer. For example a preparation of amnion tissue or amnion material can include amniotic membrane (AM), an amniotic membrane extract, an amniotic membrane jelly extract, an amniotic membrane stromal extract, and the like. In some embodiments, the amnion layer of the amniotic sac can be separated from the chorion to be used as an amnion tissue preparation. Alternatively, in some embodiments, placental tissue, which contains both the amnion layer and the chorion layer, can be used to produce and amnion tissue preparation.

Amnion tissue preparations can be in the form of a liquid, suspension, or dried form (e.g., ground or pulverized lyophilized powder), or other forms. In some embodiments, the amnion tissue preparation can be in the form of a liquid. In some embodiments, the amnion tissue preparation can be in the form of a dried powder. In some embodiments, the amnion tissue preparation can be a dried amnion tissue preparation. In some embodiments, the amnion tissue preparation can be a dried powder suspended or dissolved in a liquid.

The term "liquid amnion tissue preparation" as used herein refers to a preparation of amnion tissue or amnion material that has a water content of at least 8.1%. In some embodiments, the liquid amnion tissue preparation can have a water, or other liquid content, that is greater than about 8.5% (e.g., greater than about 9%, greater than about 10%, greater than about 15%, greater than about 20%, greater than about 30%, greater than about 40%, greater than about 50%, greater than about 60%, greater than about 70%, greater than about 80%, or greater than about 90%). In some embodiments, an amnion tissue preparation can be a liquid preparation (e.g., solution or suspension) that is prepared from a dried amnion tissue preparation.

The term "dried amnion tissue preparation" as used herein refers to a preparation of amnion tissue or amnion material that is dried to have a water content that is less than about 8 percent (e.g., less than about 7%, less than about 6%, less than about 5%, less than about 4%, less than about 3%, less than about 2%, or less than about 1%). In some embodiments, a dried amnion tissue preparation can have a water content that is between about 0.1% and about 8% (e.g., between about 0.5% and about 8%, between about 1% and about 8%, between about 0.1% and about 5%, between about 0.1% and about 4%, between about 0.1% and about 3%, between about 0.5% and about 5%, or between about 1% and about 4%).

A dried amnion tissue preparation can be stored in a smaller volume, and may not require the same low temperature storage requirements to keep the formulation from degrading over time. In some embodiments, an amnion tissue preparation can be dried using any appropriate technique such as micronization, vacuum drying, spray drying, freeze drying, or combinations thereof. In some embodiments, an amnion tissue preparation or stem cell preparation can be dried as described elsewhere (e.g., U.S. Pat. No. 5,656,498). A dried amnion tissue preparation can have any appropriate particle size for dissolution, suspension, or delivery via inhalation. For example, in some embodiments, a dried amnion tissue preparation, for example, a dried amnion tissue preparation for dissolution and reconstitution, can have a particle size ranging from about 0.1 μm to about 25 μm (e.g., from about 0.5 μm to about 25 μm, from about 0.75 μm to about 25 μm, from about 1 μm to about 25 μm, from about 0.1 μm to about 15 μm, from about 0.1 μm to about 10 μm, from about 0.1 μm to about 7.5 μm, from about 0.1 μm to about 5 μm, from about 0.75 μm to about 7.5 μm, or from about 1 μm to about 5 μm). In some embodiments, a dried amnion tissue preparation, for example, a dried amnion tissue preparation for dissolution, suspension, or direct inhalation can have a particle size ranging from about 0.1 μm to about 5 μm (e.g., from about 0.2 μm to about 5 pun, from about 0.5 μm to about 5 μm, from about 1 μm to about 5 μm, from about 1.5 μm to about 5 μm, from about 2 μm to about 5 μm, from about 2.5 μm to about 5 μm, from about 2.75 μm to about 5 μm, from about 3 μm to about 5 μm, from about 3.25 μm to about 5 μm, from about 3.5 μm to about 5 μm, from about 3.75 μm to about 5 μm, from about 4 μm to about 5 μm, from about 4.25 μm to about 5 μm, from about 4.5 μm to about 5 μm, from about 4.75 μm to about 5 μm, from about 0.1 μm to about 4.5 μm, from about 0.2 μm to about 4.5 μm, from about 0.5 μm to about 4.5 μm, from about 1 μm to about 4.5 μm, from about 1.5 μm to about 4.5 μm, from about 2 μm to about 4.5 μm, from about 2.5 μm to about 4.5 μm, from about 2.75 μm to about 4.5 μm, from about 3 μm to about 4.5 μm, from about 3.25 μm to about 4.5 μm, from about 3.5 μm to about 4.5 μm, from about 3.75 μm to about 4.5 μm, from about 4 pin to about 4.5 μm, from about 4.25 μm to about 4.5 μm). In some embodiments, dried amnion tissue preparation can be stored and reconstituted prior to use, or used directly as a dried amnion tissue preparation (e.g., dry powder amnion tissue preparation). In some embodiments, the dried amnion tissue preparation be stored. The storage temperature can vary from less than about −196° C. −80° C., −50° C., or −20° C. to more than about 23° C. If desired, the powder can be characterized (weight, protein content, etc) prior to storage.

In some embodiments, the final composition containing a dried amnion tissue preparation may not be a dried composition or a dry powder composition. For example, in some embodiments, the composition may include liquid or fluid components that render the final composition a liquid or fluid. For example, compositions used in metered dose inhalers may include one or more of propellants, surfactants, flavorants, and the like. In some embodiments, the compositions can include a dried amnion tissue preparation in combination with inactive ingredients that render the inhalable composition a liquid, fluid, cream, or semi-solid. In some embodiments, the dried amnion tissue preparation, e.g., dry powder amnion tissue preparation, can be reconstituted in a suitable solution or buffer prior to use. Exemplary solutions include but are not limited to PBS, DMEM, and BSS. In some embodiments, the pH of the solution can be adjusted as needed. The concentration of the amnion tissue preparation can be varied as needed, depending on the subject's respiratory disorder, medical condition, and the like. In some procedures a more concentrated preparation can be useful, whereas in other procedures, a solution with a low concentration of amnion tissue preparation can be useful. Additional compounds can be added to the reconstituted amnion tissue preparation. Exemplary compounds that can be added to the reconstituted composition include but are not limited to pH modifiers, buffers, collagen, HA, antibiotics, surfactants, stabilizers, proteins, and the like, as well as those listed herein for inclusion in the product substrate.

An amnion tissue preparation, e.g., a liquid amnion tissue preparation or a dried amnion tissue preparation, can contain viable cells, non-viable cells, or a combination thereof. For example, an amnion tissue preparation can be a preparation of amnion tissue or amnion material having viable cells. In some embodiments, an amnion tissue preparation can be a solution or suspension of amnion tissue or amnion material having viable cells. In some embodiments, amnion tissue or amnion material can be obtained and then treated in a manner designed to lyse some or all of the cells within the amnion tissue or amnion material. For example, in some embodiments, an amnion tissue preparation can be a preparation of amnion tissue or amnion material where all the cells were removed, killed, or lysed such that the amnion tissue preparation lacks viable cells. In some embodiments, a dried amnion tissue preparation can be a preparation of amnion tissue or amnion material that was exposed to one or more physical and/or chemical treatments that killed, fixed, or lysed the cells of the amnion tissue or amnion material such that the amnion tissue preparation lacks viable cells. For example, in some embodiments, temperature (e.g., rapid freezing or rapid freezing-thawing), force and pressure, and/or electrical disruption can be used to kill or lyse cells within amnion tissue or amnion material to produce an amnion tissue preparation that lacks viable cells.

In some embodiments, a dried amnion preparation can be prepared from human amnion tissue. In some embodiments, human amnion tissue can be harvested, processed to remove, kill, or lyse cells or to remove blood, and dried to form a dried amnion tissue preparation. In some embodiments, human amnion tissue can be processed to remove blood prior to forming a dried amnion tissue preparation. In some embodiments, human amnion tissue can be processed without removing cells or blood prior to forming a dried amnion tissue preparation.

An example of an amnion tissue preparation includes, without limitation, a dried human amnion tissue preparation that lacks viable cells, a dried human amnion tissue preparation that includes viable cells, a liquid human amnion tissue preparation that lacks viable cells, and a liquid human amnion tissue preparation that includes viable cells. In some embodiments, an amnion tissue preparation, such as a dried amnion tissue preparation, can be obtained from MiMedX® or a tissue bank (e.g., a human tissue bank).

In some embodiments, the substrate product substrate can comprise amniotic fluid, an amnion tissue preparation, or a combination thereof, in combination with a stein cell preparation.

Stem cell preparations can be in the form of a liquid, suspension, or dried form (e.g., ground or pulverized lyophilized powder), or other forms. In some embodiments, the stem cell preparation can be in the form of a liquid. In some embodiments, the stem cell preparation can be in the form of a dried powder. In some embodiments, the stem cell preparation can be a dried stem cell preparation. In some embodiments, the stem cell preparation can be a dried powder suspended or dissolved in a liquid.

The term "liquid stem cell preparation" as used herein refers to a preparation of stem cells or stem cell material that has a water content of at least 8.1%. In some embodiments, the liquid stem cell preparation can have a water, or other liquid content, that is greater than about 8.5% (e.g., greater than about 9%, greater than about 10%, greater than about 15%, greater than about 20%, greater than about 30%, greater than about 40%, greater than about 50%, greater than about 60%, greater than about 70%, greater than about 80%, or greater than about 90%). In some embodiments, a stem cell preparation can be a liquid preparation (e.g., solution or suspension) that is prepared from a dried stem cell preparation.

The term "dried stem cell preparation" as used herein refers to a preparation of stem cell or stem cell material that is dried to have a water content that is less than about 8 percent (e.g., less than about 7%, less than about 6%, less than about 5%, less than about 4%, less than about 3%, less than about 2%, or less than about 1%). In some embodiments, a dried stem cell preparation can have a water content that is between about 0.1% and about 8% (e.g., between about 0.5% and about 8%, between about 1% and about 8%, between about 0.1% and about 5%, between about 0.1% and about 4%, between about 0.1% and about 3%, between about 0.5% and about 5%, or between about 1% and about 4%).

A dried stem cell preparation can be stored in a smaller volume, and may not require the same low temperature storage requirements to keep the formulation from degrading over time. In some embodiments, a stem cell preparation can be dried using any appropriate technique such as micronization, vacuum drying, spray drying, freeze drying, or combinations thereof. In some embodiments, a stem cell preparation can be dried as described elsewhere (e.g., U.S. Pat. No. 5,656,498). A dried stem cell preparation can have any appropriate particle size for dissolution, suspension, or delivery via inhalation. For example, in some embodiments, a dried stem cell preparation, for example, a dried stem cell preparation for dissolution and reconstitution, can have a particle size ranging from about 0.1 µm to about 25 µm (e.g., from about 0.5 µm to about 25 µm, from about 0.75 µm to about 25 µm, from about 1 µm to about 25 µm, from about 0.1 µm to about 15 µm, from about 0.1 µm to about 10 µm, from about 0.1 µm to about 7.5 µm, from about 0.1 µm to about 5 µm, from about 0.75 µm to about 7.5 µm, or from about 1 µm to about 5 µm). In some embodiments, a dried stem cell preparation, for example, a dried stem cell preparation for dissolution, suspension, or direct inhalation can have a particle size ranging from about 0.1 µm to about 5 µm (e.g., from about 0.2 µm to about 5 µm, from about 0.5 µm to about 5 µm, from about 1 µm to about 5 µm, from about 1.5 µm to about 5 µm, from about 2 µm to about 5 µm, from about 2.5 µm to about 5 µm, from about 2.75 µm to about 5 µm, from about 3 µm to about 5 µm, from about 3.25 µm to about 5 µm, from about 3.5 µm to about 5 µm, from about 3.75 µm to about 5 µm, from about 4 µm to about 5 µm, from about 4.25 µm to about 5 µm, from about 4.5 µm to about 5 µm, from about 4.75 µm to about 5 µm, from about 0.1 µm to about 4.5 µm, from about 0.2 µm to about 4.5 µm, from about 0.5 µm to about 4.5 µm, from about 1 µm to about 4.5 µm, from about 1.5 µm to about 4.5 µm, from about 2 µm to about 4.5 µm, from about 2.5 µm to about 4.5 µm, from about 2.75 µm to about 4.5 µm, from about 3 µm to about 4.5 µm, from about 3.25 µm to about 4.5 µm, from about 3.5 µm to about 4.5 µm, from about 3.75 µm to about 4.5 µm, from about 4 µm to about 4.5 µm, from about 4.25 µm to about 4.5 µm). In some embodiments, dried stein cell preparation can be stored and reconstituted prior to use, or used directly as a dried stem cell preparation (e.g., dry powder stem cell preparation). In some embodiments, the dried stem cell preparation be stored. The storage temperature can vary from less than about −196° C. −80° C., −50° C., or −20° C. to more than about 23° C. If desired, the powder can be characterized (weight, protein content, etc.) prior to storage.

In some embodiments, the final composition containing a dried stem cell preparation may not be a dried composition or a dry powder composition. For example, in some embodiments, the composition may include liquid or fluid components that render the final composition a liquid or fluid. For example, compositions used in metered dose inhalers may include one or more of propellants, surfactants, flavorants, and the like. In some embodiments, the compositions can include a dried stem cell preparation in combination with inactive ingredients that render the inhalable composition a liquid, fluid, cream, or semi-solid. In some embodiments, the dried stem cell preparation, e.g., dry powder stem cell preparation, can be reconstituted in a suitable solution or buffer prior to use. Exemplary solutions include but are not limited to PBS, DMEM, and BSS. In some embodiments, the pH of the solution can be adjusted as needed. The concentration of the stem cell preparation can be varied as needed, depending on the subject's respiratory disorder, medical condition, and the like. In some procedures a more concentrated preparation can be useful, whereas in other procedures, a solution with a low concentration of stem cell preparation can be useful. Additional compounds can be added to the reconstituted stem cell preparation. Exemplary compounds that can be added to the reconstituted composition include but are not limited to pH modifiers, buffers, collagen, HA, antibiotics, surfactants, stabilizers, proteins, and the like, as well as those listed herein for inclusion in the product substrate.

A stem cell preparation, e.g., a liquid stem cell preparation or a dried stem cell preparation, can contain viable cells, non-viable cells, or a combination thereof. For example, a stem cell preparation can be a preparation of stem cells or stein cell material having viable cells. In some embodiments, a stem cell preparation can be a solution or suspension of stem cell or amnion material having viable cells. In some embodiments, stem cells or stem cell material can be obtained and then treated in a manner designed to lyse some or all of the cells within the stem cell preparation or stem cell material. For example, in some embodiments, a stem cell preparation can be a preparation of stem cells or stem cell material where all the cells were removed, killed, or lysed such that the stem cell preparation lacks viable cells. In some embodiments, a dried stem cell preparation can be a preparation of stem cells or stem cell material that was exposed to one or more physical and/or chemical treatments that killed, fixed, or lysed the cells of the stem cell material such that the stem cell preparation lacks viable cells. For example, in some embodiments, temperature (e.g., rapid freezing or rapid freezing-thawing), force and pressure, and/or electrical disruption can be used to kill or lyse cells within stem cell material to produce a stem cell preparation that lacks viable cells.

In some embodiments, a stem cell culture can be obtained and then treated in a manner designed to lyse all the stem cells. In these cases, the resulting material (e.g., cellular remnants from lysed stem cells) can be used directly as a liquid stem cell preparation that lacks viable cells, dried to form a dried stem cell preparation that lacks viable stem cells, or dried and then reconstituted to form a liquid stem cell preparation that lacks viable cells.

Examples of stem cell preparations include, without limitation, a lung stem cell preparation such as a lung epithelial progenitor cell preparation, a mesenchymal stem cell (MSC) preparation (e.g., a MSC preparation obtained from fat tissue or bone marrow), an umbilical cord blood stem cell preparation, an embryonic stem cell preparation, and a human induced pluripotent stem cell preparation.

In some embodiments, a stem cell preparation can be prepared from cultures of stem cells. In some embodiments, a stem cell preparation can be prepared by washing a culture of stem cells in saline (e.g., phosphate buffered saline) to remove culture medium, evaporating to remove wash medium, adding a solution (e.g., saline, water, or a water and sugar solution) to the resulting stem cell preparation, and, optionally, repeating the evaporation step. After the optional second evaporation step, the stem cell preparation can be formulated into a powder that can be used directly as a dried stem cell preparation or mixed with a liquid formulation to produce a liquid product substrate containing a stem cell preparation.

An example of a stem cell preparation includes, without limitation, a dried human stem cell preparation that lacks viable cells, a dried human stem cell preparation that includes viable cells, a liquid human stem cell preparation that lacks viable cells, and a liquid human stem cell preparation that includes viable cells. In some embodiments, a stem cell preparation, such as a dried stem cell preparation or a liquid stem cell preparation, can be obtained commercially from, e.g., Stemedica Cell Technologies, Inc.

In some embodiments, inhalable products described herein can comprise AF, an amnion tissue preparation, stem cells, a stem cell preparation, or combinations thereof as described herein, and can include one or more additional therapeutic agents. For example, inhalable products (e.g., variable phase, density, or size products) described herein, generated by a device described herein, can be generated from a product substrate comprising F, an amnion tissue preparation, stem cells, a stem cell preparation, or combinations thereof, as Swell as one or more bronchodilators, one or more anti-inflammatory agents (e.g., non-steroidal anti-inflammatory drugs, dexamethasone or other type of glucocorticoid steroids), one or more growth factors (e.g., platelet derived growth factor PDGF, epithelial growth factor (EGF), fibroblast growth factor-2 (FGF2), or stem cell factor (SCF)), one or more lung surfactants (e.g., DPPC), and/or one or more antimicrobial agents (e.g., antibiotics such as kanamycin, neomycin, streptomycin, or gentamicin or an antifungal agent).

In another aspect, this document provides methods and materials for treating or preventing disorders and conditions by administering products (e.g., variable density, phase, or size products) described herein generated by devices described herein. Methods described herein include using devices, inhalers, and breathing systems described herein for treating or preventing disorders (e.g., respiratory disorders and non-respiratory disorders, methods of providing long-term maintenance treatment following an acute treatment of a disorder (including but not limited to acute respiratory disorders), and methods of regenerating or restoring respiratory tissue (including but not limited to lung tissue) or respiratory function.

In some embodiments, the methods, breathing systems, inhalers, and devices described herein can be used to treat a subject having one or more respiratory disorders or one or more non-respiratory disorders, provide prophylaxis to a subject to prevent or reduce the severity of a developing respiratory disorder or non-respiratory disorder, provide maintenance treatment to a subject following an acute treatment of a respiratory disorder or non-respiratory disorder in the subject, or regenerate or restore respiratory tissue or respiratory function in a subject following an acute respiratory disorder. Exemplary non-respiratory disorders that can be treated, reduced, prevented, or repaired by administration of products (e.g., variable density, phase, or size products) as described herein generated by devices or inhalers described herein can include, without limitation, cardiovascular disease, an ocular disease, migraine, a pain-related disorder, an autoimmune disorder, alopecia, sexual dysfunction, skin treatment for psoriasis, and combinations thereof. Exemplary respiratory disorders that can be treated, reduced, prevented, or repaired by administration of products (e.g., variable density, phase, or size products) as described herein generated by devices or inhalers described herein can include, without limitation, bronchospasms, COPD, chronic bronchitis, asthma, emphysema, pulmonary hypertension, interstitial lung disease, pulmonary fibrosis, pneumonia, interstitial pneumonia, lung infections, idiopathic pulmonary fibrosis, covid-19, coronavirus, acute respiratory distress syndrome, and infections such SARS-CoV-2, SARS-CoV, MFRS, and Pertussis. Methods of treatment described herein can include treatment of subjects requiring mechanical breathing assistance (e.g. mechanical ventilation), spontaneously breathing subjects with artificial airways, or ambulatory subjects capable of independent, spontaneous breathing.

As described herein, respiratory disorders and non-respiratory disorders can be treated by administering (e.g., via inhalation) an effective amount of an active agent intended for treating the disorder in the form of products (e.g., variable density, phase, or size products) described herein comprising the active agent, generated by devices described herein. Effective amounts of active agents herein can be determined, e.g., by a physician, taking into account various factors such as overall health status, body weight, sex, diet, time and route of administration, other medications, and any other relevant clinical factors. As used herein, an "effective amount" or "therapeutically effective amount" of a composition is the amount that is sufficient to provide a beneficial effect to the subject to which the composition or preparations are delivered. The effective amount can be the amount effective to achieve an improved survival rate, a more rapid recovery, an improvement in the quality of life, or an improvement or elimination of one or more symptoms associated with a subject's disorder (e.g., covid-19).

In some embodiments, methods are provided herein for treating a subject or providing prophylaxis to a subject comprising mechanically ventilating the subject with a breathing system as described herein. In some embodiments, the methods can include delivering products (e.g., variable density, phase, or size products) described herein comprising the active agent, generated by devices described herein, to the subject through the breathing system. For example, a method of treating a subject having a disorder (e.g., a respiratory disorder or a non-respiratory disorder) or providing prophylaxis to a subject to prevent or reduce the severity of a developing disorder (e.g., a respiratory disorder or a non-respiratory disorder) can include mechanically ventilating the subject with a breathing system, and delivering products (e.g., variable density, phase, or size products) described herein comprising the active agent, generated by devices described herein, to the subject through the breathing system. In some embodiments, wherein a product substrate from which the products are generated comprises amniotic fluid, an amnion tissue preparation, or a combination thereof as active agent, alone or in combination with stem cells, a stem cell preparation, or a combination thereof. The breathing system can include a pressure-assisted breathing device, as described herein, such as a mechanical ventilator. In some embodiments, the pressure-assisted breathing device can be selected from the group consisting of an intensive care ventilator, a bubble ventilator, a continuous positive airway pressure system, a bi-level positive airway pressure system, an automatic positive airway pressure system, and an adaptive servo ventilation system. The breathing system can be configured to deliver the products (e.g., variable density, phase, or size products) described herein comprising the active agent, generated by devices described herein, to the subject. For example, in some embodiments, the breathing system can include a delivery device described herein, or inhaler comprising a delivery device described herein. The delivery device can be operably connected to the breathing system to deliver the products to the lungs of the subject through the breathing system. For example, the delivery device can release an aerosol, a mist, a heavy mist, a vapor or other product described herein, generated from a product substrate comprising one or more active agents, into the breathing system. In some embodiments, the products delivered into the breathing system are the products delivered to the subject. In some embodiments, at least some of the products delivered to the breathing system transform within the breathing system prior to delivery to the subject. For example, in some embodiments, some or all of products delivered to a breathing system in a vapor phase can condense within the breathing system into a heavy mist prior to delivery into a subject. Transformation of products within a breathing system can depend on the several factors, including characteristics (e.g., temperature, product substrate formulation, and the like) of the products upon delivery into the breathing system, length of breathing system tubing the products must traverse prior to delivery into the subject, temperature of gas in the breathing system, and the like, and can readily be controlled or varied by one skilled in the art. Once delivered into a breathing system, the products can be transported into the subject's lungs during ventilation (e.g., during inhalation). In some embodiments, the composition can be delivered to the subject as a solution aerosol, a suspension aerosol, a mist, a heavy mist, a vapor, or combinations thereof. The method can include actuating the delivery device to deliver one or more doses of the products (doses of the active agent or agents contained within the products or product substrate) into the breathing system. Appropriate doses can be determined by, e.g., a physician, taking into account, the subject's condition, disorder, symptoms, age, weight, sex, height, BMI, oxygen saturation, or other circumstances.

In some embodiments, the devices described herein can have several advantages over traditional inhalation devices such as pMDIs, nebulizers, and dry powder inhalers. For example, the devices described herein can, in some embodiments, be used for treatment in place of pMDIs, nebulizers, and dry powder inhalers. In some embodiments, the devices described herein are faster at delivering an active agent to a subject than using nebulizer delivery. In some embodiments, the devices described herein provide a significant reduction in unwanted aerosol generation. For example, using devices that result in in infectious aerosols circulating in a healthcare environment can lead to infection of non-infected individuals (e.g., without wishing to be bound by theory, it is believed that use of traditional inhalers, including pMDIs and dry powder inhalers, as well as nebulizers in patients with SARS-CoV-2 infections can lead to increased generation of infectious aerosols being released from an infected subject using the traditional inhalers or nebulizers). In some embodiments, the decreased generation of infectious aerosols can be a result of the selective generation of non-aerosol active agent products for inhalation, the selective generation of heavy mist products, the selective deposition of generated products in desired portions of the subject's respiratory system, inclusion of a one-way valve in some devices, or a combination thereof. In some embodiments where devices described herein are used in place of traditional nebulizers as part of a breathing system described herein, the devices can have the advantage of nebulizing a subject cyclically with the breathing cycle. For example, in some embodiments, devices described herein can, when connected with a breathing system, provide delivery of controlled nebulized active agent to a subject with each breath of the subject.

The method can be useful for treatment or prophylaxis of any suitable disorder or condition (e.g., a respiratory disorder or a non-respiratory disorder). For example, respiratory disorders and conditions that can benefit from the methods described herein include, without limitation, bronchospasms, chronic obstructive airway disease, COPD, chronic bronchitis, asthma, emphysema, pulmonary hypertension, interstitial lung disease, pulmonary fibrosis, cystic fibrosis, pneumonia, interstitial pneumonia, lung infections (e.g., bacterial, viral, or fungal), idiopathic interstitial lung disease (e.g., idopathic pulmonary fibrosis), covid-19, acute respiratory distress syndrome, intensive care unit syndrome, acute inhalation injuries, and infections such SARS-CoV-2, SARS-CoV, MERS, and Pertussis. As another example, non-respiratory disorders and conditions that can benefit from the methods described herein include, without limitation, cardiovascular disease, an ocular disease, migraine, a pain-related disorder, an autoimmune disorder, alopecia, sexual dysfunction, skin treatment for psoriasis, and combinations thereof. Disorders having both respiratory and non-respiratory aspects and symptoms can also be treated using the methods described herein. For example, other disorders and conditions that can benefit from the methods described herein include, without limitation, cystic fibrosis, sarcoidosis, systemic inflammatory response syndrome (SIRS), sepsis, multiple organ dysfunction syndrome, and combinations thereof.

In some embodiments, methods are provided herein for treating a subject having a disorder, by administering, by way of ambulatory inhalation from a device described herein, products (e.g., variable density, phase, or size products) described herein, generated by device, wherein the products comprise one or more active agents. Ambulatory inhalation includes inhalation by a subject that can breath without mechanical assistance. For example, a subject that can complete ambulatory inhalation can inhale and exhale without assistance. Such a subject could use the device at home, during a mobile situation, or at a clinic or hospital under (e.g., under physician supervision).

In some embodiments, methods are provided herein for treating a subject having a disorder by administering, to lung tissue of the subject, products (e.g., variable density, phase, or size products) described herein, generated by a device described herein. In some embodiments, the administering occurs through ambulatory inhalation of the composition by the subject from a delivery device.

In some embodiments of the methods described herein, administration of the products (e.g., variable density, phase, or size products) described herein, generated by a device described herein, can occur after some initial treatment for a disorder (e.g., a respiratory disorder). For example, a subject may initially receive acute treatment for a disorder (such as a respiratory disorder or a non-respiratory disorder) in the form of, e.g. products described herein, or any other therapy or treatment (e.g., respiratory therapy or respiratory treatment). Then, some time after the initial treatment, such as, e.g., acute treatment, the subject can be administered one or more doses of products (e.g., variable density, phase, or size products) described herein, generated by a device described herein. For example, after some period following acute treatment, a subject can receive a products (e.g., variable density, phase, or size products) described herein, generated by a device described herein as, e.g., a maintenance treatment, a regenerative treatment, a restorative treatment, or as prophylaxis for preventing relapse of disorder or condition (e.g., a respiratory disorder). For example, in some embodiments, methods described herein can include providing maintenance treatment to a subject following an acute treatment of a respiratory disorder in the subject, by administering, to lung tissue of the subject, after completion of acute treatment of the subject's respiratory disorder, products (e.g., variable density, phase, or size products) described herein, generated by a device described herein. In some embodiments, the products can comprise amniotic fluid, an amnion tissue preparation, or a combination thereof, as active agent. In some embodiments, the products can further comprise stem cells, a stem cell preparation, or a combination thereof. As another example, in some embodiments, methods described herein can include regenerating or restoring respiratory tissue or respiratory function in a subject following an acute respiratory disorder in the subject by administering, to lung tissue of the subject, products (e.g., variable density, phase, or size products) described herein, generated by a device described herein. In some embodiments, methods described herein can include regenerating or restoring respiratory tissue or respiratory function in a subject following an acute respiratory disorder in the subject by administering, to lung tissue of the subject, products (e.g., variable density, phase, or size products) described herein, generated by a device described herein, comprising amniotic fluid, an amnion tissue preparation, or a combination thereof. In some embodiments, acute treatment can include mechanical ventilation, oxygen administration, ambulatory oxygen administration, or a combination thereof. In some embodiments, administration of the products (e.g., variable density, phase, or size products) described herein after initial treatment can occur after the subject has been discharged from hospital care, downgraded from intensive care, downgraded from acute care, downgraded from critical care, or removed from acute care treatment. In some embodiments, administration of the products (e.g., variable density, phase, or size products) described herein after initial treatment can occur more than 1 day, more than 2 days, more than 3 days, more than 1 week, more than 2 weeks, more than 3 weeks, more than 6 weeks, more than 8 weeks, more than 10 weeks, or more than 15 weeks after the subject has been discharged from hospital care, downgraded from intensive care, downgraded from acute care, downgraded from critical care, or removed from acute care treatment. In some embodiments, administration of the products (e.g., variable density, phase, or size products) described herein after initial treatment can include administering once daily, multiple times daily, every other day, weekly, or monthly for a period of from about 1 day to about 10 years following the acute treatment.

In some embodiments, such as where a subject is provided with a maintenance treatment or prophylaxis against relapse of a respiratory disorder, the respiratory disorder can be selected from acute or chronic respiratory disorders, infections, and associated symptoms. Non-limiting examples of acute respiratory disorders include acute asthma, acute upper respiratory diseases (e.g., common cold or human coronavirus infections, common upper respiratory tract infections, influenza, diptheria, croup, allergic rhinitis, acute sinusitis, acute tonsillitis, acute pneumonia, pleural effusion, collapsed lung, acute bronchitis, bronciolitis, acute respiratory distress syndrome (ARDS), sudden acute respiratory syndrome (SARS, including SARS-CoV-2 or covid-19), pulmonary embolism, Middle East respiratory syndrome (MERS), pulmonary hypertension, acute pulmonary edema, respiratory depression (resulting from, e.g., opioid narcotics, barbituates, sedatives, alcohol, tumor, metabolic disorder, neuromuscular disease, airway obstruction, and the like), respiratory syncytial virus (RSV) infection, mucociliary dysfunction (e.g., resulting from acute infections including, but not limited to pertussis), cough, tuberculosis, acute interstitial lung disease, pulmonary hyperplasia, pulmonary interstitial emphysema, infant respiratory distress syndrome or surfactant deficiency disorder, and the like. Non-limiting examples of chronic respiratory disorders include chronic sinusitis, chronic epiglottitis, chronic pharyngitis, chronic stridor, chronic tonsillitis, chronic obstructive pulmonary disease (COPD) (including, but not limited to, chronic bronchitis, emphysema, bronchiolitis, non-reversible asthma, certain types of bronchiectasis), mucociliary dysfunction (e.g., resulting from chronic conditions including, but not limited to, cystic fibrosis (CF) and primary ciliary dyskinesia (PCD), chronic tuberculosis, cystic fibrosis, chronic pulmonary edema, neuromuscular disorders (including, but not limited to, myasthenia gravis, amyotrophic lateral sclerosis, and the like), primary ciliary dyskinesia, pulmonary MAC infection or MAC lung disease, interstitial lung disease (such as, but not limited to, idiopathic pulmonary fibrosis, nonspecific interstitial pneumonitis, and the like), chronic asthma, chronic symptoms or long-term periods of recovery from acute respiratory distress syndrome, *Pseudomonas aeruginosa* infection, respiratory cancers or tumors (including, but not limited to, primary carcinomas of the lung, small cell lung cancer, non-small cell lung cancer, (e.g., adenocarcinoma of the lung, squamous cell carcinoma of the lung, large cell lung carcinoma), carcinoid, Kaposi's sarcoma, melanoma, lymphoma, head and neck cancer, pleural mesothelioma, lung metastases of cancers (such as, but not limited to, breast cancer, liver cancer, colon cancer, prostate cancer, germ cell cancer, and renal cell carcinoma metastases), benign tumors (e.g., pulmonary hamartoma, pulmonary sequestration, and congenital cystic adenomatoid malformation (CCAM)), autoimmune disorders (such as, but not limited to, granulomatosis with polyangiitis, Goodpasture's syndrome, and the like), bronchopulmonary dysplaysias, and the like. In some embodiments, such as where the subject is provided with a method of regenerating or restoring respiratory tissue or respiratory function in a subject following an acute respiratory disorder in the subject, the respiratory disorder can be selected from ARDS, MERS, SARS, SARS-CoV-2 or covid-19, pneumonia, influenza, RSV infection, an inhalation injury, and the like.

In some embodiments, methods described herein can include delivering, to the subject, a composition comprising AF, an amnion tissue preparation, or a combination thereof in a form having a particle size range of from about 0.1 μm to about 5 μm (e.g., from about 0.2 μm to about 5 μm, from about 0.5 μm to about 5 μm, from about 1 μm to about 5 μm, from about 1.5 μm to about 5 μm, from about 2 μm to about 5 μm, from about 2.5 μm to about 5 μm, from about 2.75 μm to about 5 μm, from about 3 μm to about 5 μm, from about 3.25 μm to about 5 μm, from about 3.5 μm to about 5 μm, from about 3.75 μm to about 5 μm, from about 4 μm to about 5 μm, from about 4.25 μm to about 5 μm, from about 4.5 μm to about 5 μm, from about 4.75 μm to about 5 μm, from about 0.1 μm to about 4.5 μm, from about 0.2 μm to about 4.5 μm, from about 0.5 μm to about 4.5 μm, from about 1 μm to about 4.5 μm, from about 1.5 μm to about 4.5 μm, from about 2 μm to about 4.5 μm, from about 2.5 μm to about 4.5 μm, from about 2.75 μm to about 4.5 μm, from about 3 μm to about 4.5 μm, from about 3.25 μm to about 4.5 μm, from about 3.5 μm to about 4.5 μm, from about 3.75 μm to about 4.5 μm, from about 4 μm to about 4.5 μm, from about 4.25 μm to about 4.5 μm). For example, in some embodiments, the compositions can be delivered to the subject in a heavy mist form, having a particle size of from about 3.5 μm to about 5 µm (e.g., from about 3.5 µm to about 5 µm, from about 3.75 µm to about 5 µm, from about 4 µm to about 5 µm, from about 4.25 µm to about 5 µm, from about 4.5 µm to about 5 µm, from about 4.75 µm to about 5 µm, from about 0.1 µm to about 4.5 µm, from about 0.2 µm to about 4.5 µm, from about 0.5 µm to about 4.5 µm, from about 1 µm to about 4.5 µm, from about 1.5 µm to about 4.5 µm, from about 2 µm to about 4.5 µm, from about 2.5 µm to about 4.5 µm, from about 2.75 µm to about 4.5 µm, from about 3 µM to about 4.5 µm, from about 3.25 µm to about 4.5 µm, from about 3.5 µm, to about 4.5 µm, from about 3.75 µm to about 4.5 µm, from about 4 µm to about 4.5 µm, from about 4.25 µm to about 4.5 µm). In some embodiments, the compositions can be delivered to the subject in a non-aerosol form, such as a vapor form.

In some embodiments, methods described herein can include delivering, to the subject, a products (e.g., variable density, phase, or size products) described herein, generated by a device described herein, comprising AF made with from about 0.01 mg to about 1000 g (e.g., from about 0.01 mg to about 10 g, from about 0.1 mg to about 10 g, from about 1 mg to about 10 g, from about 10 mg to about 10 g, from about 100 mg to about 10 g, from about 1 g to about 100 g, from about 0.01 mg to about 5 g, from about 0.01 mg to about 1 g, from about 0.01 mg to about 100 mg, from about 10 mg to about 5 g, from about 100 mg to about 1 g, from about 10 g to about 100 g, from about 100 g to about 1000 g, or from about 1 g to about 5 g) of AF per kg body weight of the subject being treated. In some embodiments, the methods include delivering, to the subject, a composition comprising an amnion tissue preparation made with from about 0.01 mg to about 10 g (e.g., from about 0.01 mg to about 10 g, from about 0.1 ing to about 10 g, from about 1 mg to about 10 g, from about 10 mg to about 10 g, from about 100 mg to about 10 g, from about 1 g to about 10 g, from about 0.01 mg to about 5 g, from about 0.01 mg to about 1 g, from about 0.01 mg to about 100 mg, from about 10 mg to about 5 g, from about 100 mg to about 1 g, or from about 1 g to about 5 g) of amnion tissue per kg body weight of the subject being treated.

In some embodiments, the products (e.g., variable density, phase, or size products) described herein, generated by a device described herein, containing one or more active agents (e.g., AF, an amnion tissue preparation, stem cells, a stem cell preparation, a bronchodilator, an immunosuppressant, and the like, or combinations thereof) can be delivered to the subject by inhalation only once. In some embodiments, multiple (e.g., two, three, four, five, six, seven, eight, nine, 10, 11, 12, 13, 14, 15, or 20 or more) deliveries of the products (e.g., variable density, phase, or size products) described herein, generated by a device described herein, containing one or more active agents, can be made by inhalation. For example, multiple deliveries of products (e.g., variable density, phase, or size products) described herein, generated by a device described herein, containing one or more active agents, can be made over the course of several (e.g., two, three, four, five, six, seven, eight, nine, 10, 14, 21, 28, or 31 or more) consecutive days (e.g., one delivery each day for seven days or one delivery every other day for seven days). In some embodiments, products (e.g., variable density, phase, or size products) described herein, generated by a device described herein, containing one or more active agents, can be delivered from about two to four times a day to about once per month. In some cases, products (e.g., variable density, phase, or size products) described herein, generated by a device described herein, containing one or more active agents, can be delivered to a subject for several months (e.g., one delivery per month for six months, one delivery per week for two months, from about one to about three deliveries per day for about four months, etc.). In some embodiments, deliveries of the products (e.g., variable density, phase, or size products) described herein, generated by a device described herein, containing one or more active agents, can be made as part of acute therapy, prophylactic therapy, maintenance therapy, therapeutic repair therapy, or regenerative therapy, depending upon the subject's condition, disorder, desired therapeutic goals, or temporal location in the progression of a disorder or condition.

In some embodiments, methods described herein can include identifying the subject as having or at risk of developing the disorder (e.g., respiratory disorder or non-respiratory disorder). In some embodiments, methods described herein can include identifying the disorder or one or more symptoms of the disorder. Identification of the subject, disorder, or symptoms can be conducted by any suitable manner, such as diagnostics, genetic analysis, lifestyle analysis, analysis of environmental conditions, and the like.

Products (e.g., variable density, phase, or size products) described herein, generated by a device described herein, containing one or more active agents (e.g., AF, an amnion tissue preparation, stem cells, a stem cell preparation, a bronchodilator, and immunosuppressant, and the like, or combinations thereof), can be delivered to a subject at various time points after diagnosis with a disorder (e.g., a lung infection), at various time points after indication that a subject is at risk of developing a disorder (e.g., after a subject has shown signs of early development of a disorder, or after a subject has been identified as having been exposed to an infectious disease that can cause a disorder, such as after exposure to SARS-CoV-2), at various time points after a subject has received treatment for an acute disorder (e.g., acute respiratory distress syndrome), or at various time points after a subject has exhibited some improvement (e.g., reduced symptoms, increased oxygen saturation, improved heart rate, etc.) following treatment for a disorder. For example, products (e.g., variable density, phase, or size products) described herein, generated by a device described herein, containing one or more active agents, can be delivered immediately following diagnosis of a disorder (e.g., COPD), or immediately in cases of acute illness (e.g., acute respiratory distress). In some cases, products (e.g., variable density, phase, or size products) described herein, generated by a device described herein, containing one or more active agents (e.g., AF, an amnion tissue preparation, stem cells, a stem cell preparation, a bronchodilator, and immunosuppressant, and the like, or combinations thereof), can be delivered to a subject less than 10 (e.g., 9, 8, 7, 6, 5, 4, 3, 2, or 1) days after diagnosis with a disorder, after indication that a subject is at risk of developing a disorder, after a subject has received other treatment for an acute disorder, or after a subject has exhibited some improvement following treatment for a disorder.

In some embodiments, a method of treating a subject having a disorder or providing prophylaxis to a subject to prevent or reduce the severity of a developing disorder is provided. In some embodiments, the method can include delivering inhalable products (e.g., variable density, size, or phase products) described herein to the subject through a breathing system comprising a delivery device described herein, while mechanically ventilating the subject with the breathing system. In some embodiments, the method can include delivering inhalable products (e.g., variable density, size, or phase products) described herein to the subject through a delivery device described herein (e.g., ambulatory delivery, without mechanical breathing assistance, to a spontaneously breathing subject, and the like). In some embodiments, the method can include delivering inhalable products (e.g., variable density, size, or phase products) described herein to the subject through an inhaler comprising a delivery device described herein. In some embodiments, the method can further comprise actuating the delivery device to deliver one or more doses of the inhalable products into the subject, the breathing system, or a combination thereof. In some embodiments, the inhalable products can be delivered to the subject as a solution aerosol, a suspension aerosol, a vapor, or a heavy mist. In some embodiments, at least a portion of the inhalable products transforms into a heavy mist within the breathing system, the subject, or a combination thereof. In some embodiments, the method can further comprise identifying the subject as having or at risk of developing the disorder. In some embodiments, the method can further comprise identifying the disorder or one or more symptoms of the disorder. In some embodiments, delivering inhalable products to the subject through the delivery device or through the inhaler comprises delivering the inhalable products, by way of ambulatory inhalation from the delivery device or the inhaler.

In some embodiments, a method of treating a subject having a disorder is provided. In some embodiments, the method comprises administering, to lung tissue of the subject, inhalable products, through a breathing system described herein, while mechanically ventilating the subject with the breathing system. In some embodiments, the method comprises administering, to lung tissue of the subject, inhalable products, through a delivery device described herein or through an inhaler comprising a delivery device described herein. In some embodiments, the administering occurs simultaneously with or after acute treatment of a respiratory disorder. In some embodiments, the acute treatment comprises mechanical ventilation, oxygen administration, or a combination thereof. In some embodiments, the administering occurs after the subject has been discharged from hospital care, downgraded from intensive care, downgraded from acute care, downgraded from critical care, or removed from acute care treatment. In some embodiments, the administering occurs more than 1 day, more than 2 days, more than 3 days, more than 1 week, more than 2 weeks, more than 3 weeks, more than 6 weeks, more than 8 weeks, more than 10 weeks, or more than 15 weeks after the subject has been discharged from hospital care, downgraded from intensive care, downgraded from acute care, downgraded from critical care, or removed from acute care treatment. In some embodiments, the administering includes administering once daily, multiple times daily, every other day, weekly, or monthly for a period of from about 1 day to about 10 years following the acute treatment.

In some embodiments, a method of providing maintenance treatment to a subject following an acute treatment of a respiratory disorder in the subject is provided. In some embodiments, the method comprises administering, to lung tissue of the subject, through a delivery device described herein or through the inhaler comprising a delivery device described herein, inhalable products, wherein the administering occurs after completion of acute treatment of the subject's respiratory disorder. In some embodiments, the acute treatment comprises mechanical ventilation, oxygen administration, or a combination thereof. In some embodiments, the administering occurs after the subject has been discharged from hospital care, downgraded from intensive care, downgraded from acute care, downgraded from critical care, or removed from acute care treatment. In some embodiments, the administering occurs more than 1 day, more than 2 days, more than 3 days, more than 1 week, more than 2 weeks, more than 3 weeks, more than 6 weeks, more than 8 weeks, more than 10 weeks, or more than 15 weeks after the subject has been discharged from hospital care, downgraded from intensive care, downgraded from acute care, downgraded from critical care, or removed from acute care treatment. In some embodiments, the administering includes administering once daily, multiple times daily, every other day, weekly, or monthly for a period of from about 1 day to about 10 years following the acute treatment.

In some embodiments, a method of regenerating or restoring respiratory tissue or respiratory function in a subject following an acute respiratory disorder in the subject is provided. In some embodiments, the method comprises administering, to lung tissue of the subject, through a delivery device described herein or through an inhaler comprising a delivery device described herein, inhalable products comprising amniotic fluid, an amnion tissue preparation, or a combination thereof. In some embodiments, the administering occurs after acute treatment of a respiratory disorder. In some embodiments, the acute treatment comprises mechanical ventilation, oxygen administration, or a combination thereof. In some embodiments, the administering occurs after the subject has been discharged from hospital care, downgraded from intensive care, downgraded from acute care, downgraded from critical care, or removed from acute care treatment. In some embodiments, the administering occurs more than 1 day, more than 2 days, more than 3 days, more than 1 week, more than 2 weeks, more than 3 weeks, more than 6 weeks, more than 8 weeks, more than 10 weeks, or more than 15 weeks after the subject has been discharged from hospital care, downgraded from intensive care, downgraded from acute care, downgraded from critical care, or removed from acute care treatment. In some embodiments, the administering includes administering once daily, multiple times daily, every other day, weekly, or monthly for a period of from about 1 day to about 10 years following the acute treatment.

In some embodiments of the methods described herein, the disorder is a respiratory disorder. In some embodiments, a respiratory disorder can include a disorder that manifests in both the respiratory system and other organ systems of body areas.

The respiratory disorder can include, without limitation, any obstructive lung disorders, and restrictive lung disorders. In some embodiments, the inhalable products or methods of treatment described herein can improve exercise endurance, increasing baseline blood oxygen saturation, reduce inflammation in the lungs of subjects with any obstructive lung disorders, and restrictive lung disorders, and the like. In some embodiments, the inhalable products or methods of treatment described herein can decrease subject dependency on use of other supplemental treatment such as bronchodilators, and/or oxygen therapy.

In some embodiments, the respiratory disorder can be selected from chronic obstructive pulmonary disease (COPD), asthma, acute asthma, chronic asthma, severe asthma, allergic asthma, bronchial asthma, intrinsic asthma (e.g., late asthma and airway hyper-responsiveness), respiratory distress syndrome of the newborn, reversible respiratory disease, cystic fibrosis, bronchospasms, bronchitis, chronic bronchitis, bronchiectasis, alpha-1 antitrypsin emphysema, emphysema, associated cor pulmonale (heart disease secondary to disease of the lungs and respiratory system) with pulmonary hypertension, right ventricular hypertrophy and right heart failure, pulmonary hypertension, interstitial lung disease, pulmonary fibrosis, pneumonia, interstitial pneumonia, lung infections, idiopathic pulmonary fibrosis, cystic fibrosis, tuberculosis, pneumonia, severe acute respiratory syndrome, infection, pulmonary embolus, tuberculosis, pulmonary arterial hypertension, pulmonary edema, *pneumocystis* pneumonia, covid-19, and acute respiratory distress syndrome. In some embodiments, the one or more active agents can be an active agent for treating or preventing lung injury related to systemic inflammatory response syndrome (SIRS), sepsis, severe sepsis, septic shock, and multiple organ dysfunction syndrome (MODS). In some embodiments, the one or more active agents can be an active agent for treating or preventing respiratory disorder such as a respiratory or respiratory-related infection. For example, in some embodiments, the one or more active agents can be an active agent for treating bacterial, fungal, or viral infections of the respiratory system. In some embodiments, the one or more active agents can be an active agent for treating infections such SARS-CoV-2, SARS-CoV, MERS, and Pertussis. In some embodiments, the one or more active agents can be an active agent for treating or preventing a lung injury, such as an acute inhalation injury, an injury from chemical irritants, asphyxiants, smoke, heat, riot control agents, chemical warfare agents, and similar exposures. In some embodiments, the one or more active agents can be a vaccine (e.g., a vaccine delivered through respiratory administration) for treating or preventing a respiratory disorder.

In some embodiments, the disorder is acute respiratory distress syndrome (ARDS). ARDS is a rapidly progressive disease occurring in critically ill patients and leads to complications such as leaking of fluid into the lungs. ARDS is sometimes initially diagnosed as pneumonia or pulmonary edema (fluid in the lungs from heart disease), and symptoms can include shortness of breath or severe shortness of breath, cough, fever, fast heart rates, rapid breathing, chest pain. In some embodiments, the methods described herein comprise treating, alleviating, or preventing one or more symptoms associated with acute respiratory distress syndrome.

In some embodiments, the disorder is pneumonia. Pneumonia is a common lung condition caused by bacterial, viral, or fungal infections, or by other inflammation of the lungs associated with, e.g., chemical exposure or the subject's immune response. Pneumonia symptoms can include cough (in some cases, coughing expels greenish or yellow mucus, or even bloody mucus), fever, shaking, chills, shortness of breath, and the like. In some embodiments, the methods described herein comprise treating, alleviating, or preventing one or more symptoms associated with pneumonia.

In some embodiments, the disorder is an idiopathic interstitial lung disease. Idiopathic interstitial lung disease can affect the lungs in at least three ways. First, lung tissue is damaged in a known or unknown manner. Second, the alveolar wall becomes inflamed. Third, scarring (or fibrosis) begins in the stroma (or tissue between alveoli), and the lungs harden. Examples of idiopathic interstitial lung disease include idiopathic pulmonary fibrosis (IPF). Idiopathic pulmonary fibrosis refers to a group of diseases characterized by deep lung tissue inflammation and eventual scarring resulting in shortness of breath. Scarring of the alveoli (alveolar sac) and its supporting structure (stroma) in IPF can result in a loss of functional alveolar units and ultimately reduces oxygen transport from the air to the blood. IPF is sometimes referred to as diffuse parenchymal lung disease, alveolitis, idiopathic fibrotic alveolitis (CFA), idiopathic pneumonia (IPP) and normal interstitial pneumonia (UIP). Subjects with IPF often exhibit symptoms such as dry cough, chest pain, or shortness of breath. In some embodiments, the inhalable products comprise prednisone, cytoxan, TNFα, combinations thereof, or other pulmonary agents. In some embodiments, the inhalable products and methods described herein comprise treating, alleviating, or preventing one or more symptoms associated with IPF (such as reducing or preventing pulmonary scarring).

In some embodiments, the disorder is a Chronic Obstructive Airway Disease (COAD). In COAD diseases, airflow obstruction can be chronic and persistent or incidental and recurrent. Airflow obstruction can be determined by forced expiratory spirometry, which records the volume of expiratory discharge during maximum expiration. In subjects whose airflow is not occluded, a complete forced expiration typically takes 3 to 4 seconds. In chronic obstructive airflow disorder patients with obstructed airflow, complete forced expiration typically takes up to 15 to 20 seconds and can be limited by hold-on time. A normal 1 second forced expiratory volume (FEV 1) is easily measured and accurately predicted based on age, gender and height. FEV 1 and the ratio of the forced vital capacity (FEV 1/FVC) is usually greater than 0.75. The recording of airflow versus volume during forced expiration and subsequent forced inspiration (flow-volume loop) is also useful mainly to distinguish upper airway stenosis from lower airway stenosis. Examples of chronic obstructive airway disease include asthma and chronic obstructive pulmonary disease (COPD).

In some embodiments, the disorder is asthma. Asthma generally includes disorders in which airway inflammation restricts airflow to and from the lungs. Asthma is also called bronchial asthma, exercise-induced asthma-bronchial and reactive airway disease (RAD). In some cases, asthma is associated with allergies or genetic background. Asthma is characterized by extensive short-term fluctuations in the diameter or inner diameter of the bronchial airways, including symptoms that result in changes in lung function. The resulting increased resistance to airflow results in symptoms in affected patients, including shortness of breath (dyspnea), chest tightness or "compression" and wheezing. Asthmatics are characterized according to NIH guidelines and expressed as mild intermittent, mild persistent, moderate persistent and severe persistent. Types of asthma can include asthma, acute asthma, chronic asthma, severe asthma, allergic asthma, bronchial asthma, intrinsic asthma (e.g., late asthma and airway hyper-responsiveness). In some embodiments, the inhalable products and methods described herein comprise treating, alleviating, or preventing one or more symptoms associated with asthma.

In some embodiments, the disorder is chronic obstructive pulmonary disease (COPD). COPD is typically characterized by inadequate airflow with varying degrees of alveolar enlargement and lung tissue destruction leading to irreversible airflow obstruction, and includes chronic bronchitis (hypersecretion with goblet cell submucosal hypertrophy), chronic obstructive bronchitis or emphysema (airway parenchyma destruction) or a combination of these conditions. In some embodiments, the inhalable products and methods described herein comprise treating, alleviating, or preventing one or more symptoms associated with COPD.

In some embodiments, the disorder is alpha-1 antitrypsin emphysema or emphysema. In some embodiments, the inhalable products and methods described herein comprise treating, alleviating, or preventing one or more symptoms associated with emphysema.

In some embodiments, the disorder is an acute inhalation injury. Inhaled substances can cause injury in the respiratory tract (e.g., in pulmonary epithelium). Chemical irritants, asphyxiants, toxic metals, products of fires and combustion, and many other substances can cause acute inhalation injury. Some cases of acute inhalation injury may involve more than one substance or mechanism. Some individuals are at increased risk of acute inhalation injury, including farmers working near silos, firefighters, coal miners, welders working with acetylene torches, military personnel, hockey rink workers, and chemical workers. Symptoms of acute inhalation injury can range from simple to severe. In some embodiments, the disclosed formulations are used for treating, alleviating, or preventing one or more symptoms associated with an acute inhalation injury.

In some embodiments, the disclosed formulations are used for treating, alleviating, or preventing one or more symptoms associated with an inhalation injury from a chemical irritant. Common exemplary chemical irritants include chlorine, hydrogen chloride, ammonia, hydrogen fluoride (HF) and hydrofluoric acid, sulphur dioxide ($SO_2$), nitrogen oxides, phosgene, hydrogen sulfide ($H_2S$).

In some embodiments, the disclosed formulations are used for treating, alleviating, or preventing one or more symptoms associated with an inhalation injury from an asphyxiant. Asphyxiants can include simple asphyxiants, which act by displacing oxygen from inspired air resulting in a reduced fraction of inspired oxygen and subsequent hypoxemia, and chemical asphyxiants (e.g., carbon monoxide and hydrogen cyanide), which act by interfering with oxygen delivery or utilization. Any gas in high concentration can act as an asphyxiant.

In some embodiments, the disclosed formulations are used for treating, alleviating, or preventing one or more symptoms associated with an inhalation injury from exposure to chemical warfare agents or riot control agents. Common exemplary warfare and riot control agents that can cause inhalation injury include Agent Orange, mustard gas, phosgene, chloropicrin, armamentarium, toxins derived from organophosphate pesticides, chloroacetophenone, orthochlorobenzamalonitrile, zinc chloride, and the like.

In some embodiments, the disclosed formulations are used for treating, alleviating, or preventing pulmonary edema.

In some embodiments, the disclosed formulations are used for treating, alleviating, or preventing one or more symptoms associated with an inhalation injury from toxic metals, such as cadmium and mercury.

In some embodiments, the disclosed formulations are used for treating, alleviating, or preventing one or more symptoms associated with burns or smoke inhalation, including exposure to heat, particulate matter, and toxic gases. In some embodiments, the disclosed formulations are used for treating, alleviating, or preventing one or more symptoms associated with smoke inhalation.

In some embodiments, the disclosed formulations are used for treating, alleviating, or preventing one or more symptoms associated with a blast injury.

In some embodiments, the disclosed formulations are used for treating, alleviating, or preventing one or more symptoms associated with an inhalation injury caused by complex exposure, such as exposure to more than one toxic compound.

In some embodiments, the disclosed formulations are used for treating, alleviating, or preventing one or more symptoms associated with an inhalation fever, such as metal fume fever, polymer fume fever, and organic dust toxic syndrome.

In some embodiments, the disclosed formulations are used for treating, alleviating, or preventing one or more symptoms associated with coalworker's pneumoconiosis.

In some embodiments, the disorder is a respiratory infection, such as a non-respiratory viral, bacterial, or fungal infection. In some embodiments, the disclosed formulations are used for treating, alleviating, or preventing one or more symptoms associated with a respiratory infection, such as SARS-CoV-2, SARS-CoV, MERS, tuberculosis, influenza, and Pertussis.

In some embodiments, the disorder is respiratory distress syndrome of the newborn, reversible respiratory disease, bronchospasms, bronchitis, bronchiolitis, chronic bronchitis, bronchiectasis, associated cor pulmonale (heart disease secondary to disease of the lungs and respiratory system) with pulmonary hypertension, right ventricular hypertrophy and right heart failure, pulmonary hypertension, interstitial lung disease, pulmonary fibrosis, pneumonia, interstitial pneumonia, lung infections, severe acute respiratory syndrome, pulmonary embolus, pulmonary arterial hypertension, pulmonary edema, *pneumocystis* pneumonia, and covid-19 (or SARS-CoV-2 infection) or combinations thereof.

In some embodiments of the methods described herein, the disorder is a disorder having both respiratory and non-respiratory symptoms.

In some embodiments, the disorder is intensive care unit (ICU) syndrome or ICU psychosis. ICU syndrome can occur subjects as psychotic episodes in intensive care units. In some cases, underlying causes include anxiety, sleep deprivation, sensory deprivation and overload, immobilization, unfamiliar environment, pain and the like. In some embodiments, the methods described herein comprise treating, alleviating, or preventing one or more symptoms associated with intensive care unit (ICU) syndrome.

In some embodiments, the disorder is systemic inflammatory response syndrome (SIRS), sepsis, severe sepsis, septic shock, or multiple organ dysfunction syndrome (MODS). These disorders are risk factors for the development of acute lung injury. In some embodiments, the methods described herein comprise treating, alleviating, or preventing one or more symptoms associated with systemic inflammatory response syndrome (SIRS), sepsis, severe sepsis, septic shock, or multiple organ dysfunction syndrome (MODS).

In some embodiments, the disorder is cystic fibrosis. Cystic Fibrosis (CF) is an inherited disease that causes thickened mucus to form in the lungs, pancreas and other organs. In some embodiments, the methods described herein comprise treating, alleviating, or preventing one or more symptoms associated with cystic fibrosis.

In some embodiments, the disorder is sarcoidosis. Sarcoidosis is a disease that causes overreaction of a subject's immune system. Sarcoidosis can lead to lung damage, skin rashes, and eye disease and can affect multiple organs of the body. In some embodiments, the methods described herein comprise treating, alleviating, or preventing one or more symptoms associated with sarcoidosis.

In some embodiments of the methods described herein, the disorder is a non-respiratory disorder. Active agents intended for systemic activity rather than pulmonary activity can be delivered by pulmonary administration, as the lung is capable of absorbing active agents for both local deposition and for systemic delivery. In some cases, systemic delivery via pulmonary administration can have advantages over other delivery routes because of faster absorption, lack of first-pass metabolism, and the like.

In some embodiments, the disorder is an autoimmune disease (e.g., rheumatoid arthritis, juvenile rheumatoid arthritis, and the like). In some embodiments, the disorder is a spondyloarthropathy (e.g., ankylosing spondylitis or psoriatic arthritis). In some embodiments, the disorder is an intestinal disease (e.g., Crohn's disease). In some embodiments, the disorder is diabetes (e.g., diabetes mellitus). In some embodiments, the disorder is a skin disease (e.g., psoriasis). In some embodiments, the disorder is a non-respiratory infection, such as a non-respiratory viral, bacterial, or fungal infection. In some embodiments, the one or more active agents can be an active agent for treating or preventing a non-respiratory disorder that is a pain disorder selected from neuropathic, nociceptive, acute, chronic and disease-specific pain (e.g., pain associated with osteoarthritis or fibromyalgia). In some embodiments, the methods described herein comprise treating, alleviating, or preventing one or more symptoms associated with an autoimmune disease (e.g., rheumatoid arthritis, juvenile rheumatoid arthritis, and the like), a spondyloarthropathy (e.g., ankylosing spondylitis or psoriatic arthritis), an intestinal disease (e.g., Crohn's disease), diabetes (e.g., diabetes mellitus), a skin disease (e.g., psoriasis), a non-respiratory infection (e.g., a non-respiratory viral, bacterial, or fungal infection), a pain disorder selected from neuropathic, nociceptive, acute, chronic and disease-specific pain (e.g., pain associated with osteoarthritis or fibromyalgia), and the like, and combinations thereof.

In some embodiments, the one or more active agents can be delivered as inhalable products described herein to prevent a disease or disorder, such as inhalable products comprising a vaccine (e.g., a vaccine delivered through respiratory administration) for treating or preventing a non-respiratory disorder.

In some embodiments of the methods described herein, the inhalable products can comprise, as active agent, one or more agents selected from acetyl cysteine, aclidinium bromide, albuterol, albuterol sulfate, amikacin sulfate, amniotic fluid, an amnion tissue preparation, arformoterol sulfate, atropine sulfate, aztreonam, beclomethasone dipropionate, bitolterol mesylate, budesonide, ciclesonide, cromolyn sodium, desflurane, dexamethasone sodium phosphate, dornase alfa, enflurane, epinephrine, ergotamine tartrate, flunisolide, fluticasone propionate, fomoterol fumarate, glycopyrrolate, halothane, indacaterol maleate, iloprost, insulin, ipratropium bromide, isoetharine hydrochloride, isoflurane, isoproterenol hydrochloride, levalbuterol hydrochloride, levodopa, loxapine, mannitol, metaproterenol sulfate, methacholine chloride, mometasone furoate, nedocromil sodium, nicotine, nitric oxide, olodaterol hydrochloride, pentamidine isethionate, pentetate calcium trisodium, pentetate zinc trisodium, pirbuterol acetate, revefenacin, ribavirin, salmeterol xinafoate, sevoflurane, stem cells, a stem cell preparation, terbutaline sulfate, tetrahydrocannabinol, cannabidiol, tiotropium bromide, tobramycin, trimcinolone acetonide, umeclidinium bromide, vilanterol trifenatate, xenon xe-133, zanamivir, epinephrine, sodium chloride, and combinations thereof.

In some embodiments of the methods described herein, the inhalable products comprise amniotic fluid, an amnion tissue preparation, stem cells, a stem cell preparation, or combinations thereof. In some embodiments, the inhalable products consist essentially of amniotic fluid, an amnion tissue preparation, or a combination thereof. In some embodiments, the amniotic fluid or the amnion tissue preparation lacks viable cells. In some embodiments, the stem cell preparation lacks viable cells. In some embodiments, the amniotic fluid or the amnion tissue preparation comprises viable cells. In some embodiments, the stem cell preparation comprises viable cells.

In some embodiments of the methods described herein, the inhalable products comprise amniotic fluid, an amnion tissue preparation, stem cells, a stem cell preparation, or a combination thereof.

In some embodiments of the methods described herein, the inhalable products are delivered in a form having a particle size range of from about 0.1 µm to about 5 µm (e.g., from about 0.2 µm to about 5 µm, from about 0.5 µm to about 5 µm, from about 1 µm to about 5 µm, from about 1.5 µm to about 5 µm, from about 2 µm to about 5 µm, from about 2.5 µm to about 5 µm, from about 2.75 µm to about 5 µm, from about 3 µm to about 5 µm, from about 3.25 µm to about 5 µm, from about 3.5 µm to about 5 µm, from about 3.75 µm to about 5 µm, from about 4 µm to about 5 µm, from about 4.25 µm to about 5 µm, from about 4.5 µm to about 5 µm, from about 4.75 µm to about 5 µm, from about 0.1 µm to about 4.5 µm, from about 0.2 µm to about 4.5 µm, from about 0.5 µm to about 4.5 µm, from about 1 µm to about 4.5 µm, from about 1.5 µm to about 4.5 µm, from about 2 µm to about 4.5 µm, from about 2.5 µm to about 4.5 µm, from about 2.75 µm to about 4.5 µm, from about 3 µm to about 4.5 µm, from about 3.25 µm to about 4.5 µm, from about 3.5 µm to about 4.5 µm, from about 3.75 µm to about 4.5 µm, from about 4 µm to about 4.5 pin, from about 4.25 µm to about 4.5 µm).

In some embodiments, inhalable products (e.g., variable density, size, or phase products) described herein generated by the devices described herein can have a size, density, phase, or other characteristics suitable for delivery to the upper respiratory tract (URT). The URT includes the nose, sinuses, pharynx and larynx. For example, inhalable products described herein generated by the devices described herein having a gaseous phase, or a particle size ranging from about 5 µm to about 25 µm, from about 5 µm to about 15 µm, or from about 5 µm to about 10 µm can be used to treat a disorder of the URT.

In some embodiments, inhalable products (e.g., variable density, size, or phase products) described herein generated by the devices described herein can have a size, density, phase, or other characteristics suitable for delivery to the lower respiratory tract (LRT), which includes the trachea, upper bronchi, and lungs, and be used to treat a lung disorder such as exercise-induced pulmonary hemorrhage. For example, inhalable products described herein generated by the devices described herein having a gaseous phase, or a particle size ranging from about 0.1 µm to about 5 µm (e.g., from about 0.5 µm to about 5 µm, from about 0.75 µm to about 5 µm, from about 1 µm to about 5 µm, from about 0.1 µm to about 2 µm, from about 0.1 µm to about 1 µm, from about 0.1 µm to about 0.75 µm) can be used to treat a lung disorder including, but not limited to, pulmonary hemorrhage, acute respiratory distress syndrome, covid-19, interstitial pneumonia, and other disorders that can benefit from delivery of medication to the LRT.

In some embodiments, the inhalable products (e.g., variable density, size, or phase products) described herein generated by the devices described herein can include a mixture of particles and gaseous phase, multiple phases, multiple sizes, multiple densities, and the like suitable for delivery to both the URT and LRT.

In some embodiments, additional components in addition to an active agent can be added to the product substrates described herein as desired. For example, antimicrobial agents such as antibiotics or anti-fungal agents may be added. Other substances can be added to the compositions to stabilize and/or preserve the compositions. For example, agents can be added such as those that promote healing (e.g. vitamins), improve delivery of the active agent to the lungs or otherwise enhance the delivery of the active agent or treatment of the subject (e.g. carriers, propellants, salts, preservatives, colorants, and the like). Such additions may be made, so long as the compounds do not cause irritation of the lung, and do not interfere with the desirable action of the active agent. The product substrates can be packaged and stored, for example, at room temperature, or for example, at 0° C. to 4° C., −10° C. to −20° C., or −80° C. prior to use.

The subject can be any mammal, e.g., a human (e.g., a human patient) or a non-human primate (e.g., chimpanzee, baboon, or monkey), a mouse, a rat, a rabbit, a guinea pig, a gerbil, a hamster, a horse, a type of livestock (e.g., cow, pig, sheep, or goat), a pangolin, a bat, a dog, or a cat. The subject can be any sex or age, including, e.g., neonatal, pediatric, young adult, adult, or geriatric. The subject can be a healthy subject. For example, in some embodiments, the methods, devices, and compositions described herein can be used to provide prophylactic treatment to a subject to prevent the development of a respiratory disorder, minimize the risk of developing a respiratory disorder, minimize the severity of a respiratory disorder that may develop in the future, improve lung capacity, or increase resistance to infection. As another example, in some embodiments, the methods, devices, and compositions described herein can be used to provide prophylactic treatment to a subject to prevent the development of a non-respiratory disorder, minimize the risk of developing a non-respiratory disorder (e.g. an autoimmune disorder, a cardiac disorder, and the like), minimize the severity of a non-respiratory disorder that may develop in the future, improve circulatory function, or increase resistance to non-respiratory infection. In some embodiments, the subject can have an acute condition requiring acute treatment. For example, in some embodiments, the subject can be a subject having an acute infection affecting the respiratory tract, the subject can have a recently-diagnosed respiratory disorder or non-respiratory disorder, or the subject can be a subject receiving mechanical ventilation assistance or other life-supportive assistance for a condition or disorder that is a respiratory condition or disorder, a non-respiratory condition or disorder, or as part of a scheduled surgical or other procedure. In some embodiments, the methods, devices, and composition described herein can be used to prevent, minimize, reduce, or otherwise alleviate adverse respiratory effects of mechanical ventilation or life-supportive assistance. In some embodiments, the methods, devices, and composition described herein can be used in combination with mechanical ventilation or life-supportive assistance, to treat, reduce the severity of, or reduce one or more symptoms of a respiratory disorder or non-respiratory disorder. For example, in some embodiments, the methods, devices, and composition described herein can be used in conjunction with mechanical ventilation or life-supportive assistance to treat acute respiratory distress syndrome, an acute lung infection, severe acute respiratory syndrome, or clotting, or prevent organ damage during mechanical ventilation or life-supportive assistance.

Products (e.g., variable density, size, or phase products) described herein generated by the devices described herein can be administered to a subject as a combination therapy with another treatment (e.g., a treatment used to treat or prevent a respiratory disorder, a treatment used to treat or prevent a non-respiratory disorder, and the like). For example, the combination therapy can include administering to the subject (e.g., a human patient) one or more additional agents that provide a therapeutic benefit to the subject who has, or is at risk of developing a respiratory disorder. In some embodiments, the combination therapy can include administering to the subject (e.g., a human patient) one or more additional agents that provide a therapeutic benefit to the subject who has, or is at risk of developing a non-respiratory disorder. In some cases, the composition and the one or more additional agents can be administered at the same time. In some cases, the composition can be administered first, and the one or more additional agents administered second, or vice versa (e.g., in a breathing circuit, with or without mechanical ventilation, etc.). In some cases, the one or more additional agents can be administered via pulmonary administration (e.g., inhalation), using a device described herein. In some cases, the one or more additional agents can be administered via pulmonary administration (e.g., inhalation), using a device known in the art, such as, e.g., a pressurized inhaler, a dry powder inhaler, a nebulizer, and the like. In some cases, the one or more additional agents can be administered via non-pulmonary administration (e.g., by a route other than inhalation), such as e.g., orally, subcutaneously, intraperitoneally, topically, and the like.

The efficacy of a given treatment in treating a particular disorder (e.g., a respiratory disorder, a non-respiratory disorder) can be defined as an improvement of one or more symptoms of the respiratory disorder by at least 5% (e.g., at least 10%, at least 15%, at least 20%, at least 25%, at least 30%, at least 40%, at least 50%, at least 55%, at least 60%, at least 65% or more). In some cases, efficacy of a treatment with a composition containing a dried amnion tissue preparation and/or a dried stem cell preparation can be determined from the stabilization of one or more symptoms associated with a disorder (i.e., the treatments curtail the worsening of one or more symptoms of a disorder).

In some cases, the methods described herein can include monitoring the respiratory or non-respiratory disorder in the subject to, for example, determine if the disorder is improving with treatment. Any appropriate method can be used to monitor a disorder. For example, for some subjects with a respiratory disorder, lung function (e.g., using a spirometer or arterial blood gas test) can be monitored. For subjects diagnosed with exercise-induced pulmonary hemorrhage, clinical techniques designed to detect the presence of blood in lung airways can be used. As another example, subjects with a disorder can be monitored using standard monitoring methods appropriate for the specific disorder, such as monitoring heart rate, blood counts, and the like.

In some embodiments, inhalable products (e.g., variable density, size, or phase products) described herein generated by the devices described herein, can be administered to humans who smoke tobacco products (e.g., cigarettes, cigars, or pipes) or to humans with a history of smoking tobacco products (e.g., cigarettes, cigars, or pipes) to reduce the severity of symptoms or respiratory disorders (e.g., lung symptoms) related to smoking or to reduce the development of symptoms or respiratory disorders (e.g., lung symptoms) related to smoking. For example, a human who smokes cigarettes can be administered inhalable products (e.g., variable density, size, or phase products) described herein generated by the devices described herein, that include AF, an amnion tissue preparation, stem cells, a stem cell preparation, or one or more other active agents described herein, or combinations thereof, to reduce the severity of a chronic smoker's cough, a gravelly voice, and/or shortness of breath.

In some embodiments, devices described herein can be used in an electronic vaping device or an electronic cigarette. In some embodiments, an electronic vaping device or an electronic cigarette is provided herein, comprising a delivery device as described herein for generating variable density, phase, or size products. For example, standard electronic vaping device or electronic cigarette housings can be used, and the devices described herein for generating variable density, phase, or size products can be placed within the standard electronic vaping device or electronic cigarette housings. In some embodiments, the product substrates described herein can be used as a pre-vapor formulation in an electronic vaping device. In some embodiments, standard electronic vaping formulations can be used as a product substrate in the electronic vaping devices described herein for generating variable density, phase, or size products. In some embodiments, and electronic vaping device or electronic cigarette can be rechargable, refillable, or disposable or single use.

In some embodiments, methods are provided herein for treating or preventing a respiratory condition comprising administering inhalable products (e.g., variable density, phase, or size products) described herein generated by a delivery device described herein to a subject via an electronic vaping device or electronic cigarette device. In some embodiments, the inhalable products described herein generated from the product substrates described herein can be used in combination with, or before or after, another electronic vaping formulation such as another pre-vapor formulation. In some embodiments, methods are provided herein for treating or preventing a respiratory disorder caused by, induced by, or associated with electronic vaping or electronic cigarette use, comprising administering inhalable products (e.g., variable density, phase, or size products) described herein generated by a delivery device described herein to a subject, via a delivery device described herein, an inhaler described herein, or via an electronic vaping device or electronic cigarette device comprising a delivery device described herein. In some embodiments, product substrate can include nicotine, one or more acids, one or more flavorants, or combinations thereof.

As described herein, the devices described herein can be used on mammalian subjects, and products (e.g., variable density, size, or phase products) generated by the devices described herein can be administered to mammalian subjects, including but not limited to humans, primates, canines, felines, bovines, equines, swine, rodents, and the like.

In some embodiments, a method of treating a mammal having exercise-induced pulmonary hemorrhage is provided. Exercise-induced pulmonary hemorrhage is a medical condition that refers to the presence of blood in lung airways in association with exercise. In some cases, between about 40 to 70 percent of horses may experience blood in the trachea following a horse race. Exercise-induced pulmonary hemorrhage (EIPH) is seen in most racehorses and in many other horses used in equine sports (e.g., polo, barrel racing, 3-day events) that require strenuous exercise for short periods of time, and between about 40 to 75 percent of horses may experience blood in the trachea or tracheobronchial tree (typically identified by endoscopic examination) following a horse race. Epistaxis is seen in a small proportion (~5%) of horses with EIPH. In some cases, hemorrhage can be detected (e.g., by cytologic examination of bronchioalveolar lavage) in more than 90% of racehorses. EIPH has also been reported in human athletes and other mammals, such as racing camels and racing dogs, such as greyhounds. In some embodiments, the devices described herein can be used for, and products (e.g., variable density, size, or phase products) generated by the devices described herein can be administered for treating, alleviating, or preventing one or more symptoms associated with exercise induced pulmonary hemorrhage (EIPH) in mammals. In some embodiments, the mammal can be a human, a camel, a dog, or a horse. In some embodiments, the mammal can be a racing horse. In some embodiments, the devices described herein can be used for, and products (e.g., variable density, size, or phase products) generated by the devices described herein can be administered for treating, alleviating, or preventing one or more symptoms associated with epistaxis. In some embodiments, the method comprises, or consists essentially of, administering, to the mammal via inhalation, products (e.g., variable density, size, or phase products) described herein, generated by the devices described herein. In some embodiments, the products (e.g., variable density, size, or phase products) are generated from a product substrate comprising AF, an amnion tissue preparation, or combinations thereof. In some embodiments, the products (e.g., variable density, size, or phase products) are generated from a product substrate consisting essentially of AF, an amnion tissue preparation, or combinations thereof. In some embodiments, the products (e.g., variable density, size, or phase products) are generated from a product substrate comprising AF, an amnion tissue preparation, or combinations thereof, in combination with one or more other active agents (e.g., stem cells, a stem cell preparation, a bronchodilator, etc.).

In some embodiments, methods of managing or treating a pulmonary disease in equines, e.g., horses, comprising administering, using the devices described herein are provided. In some embodiments, a method of managing or treating a puhnonary disease in equines, e.g., horses, is provided, comprising administering, to an equine, products (e.g., variable density, size, or phase products) generated by the devices described herein for treating, alleviating, or preventing one or more symptoms associated with a pulmonary disease in the equine. In some embodiments, the horses are racehorses. Airway diseases in horses typically present with symptoms such as coughing, nasal discharge, increased respiratory effort and poor performance or exercise intolerance. Fever, depression, decreased appetite, and weight loss can also be observed in horses with infectious airway diseases. In some embodiments, the equine pulmonary disease is selected from inflammatory airway disease or reactive airway disease (heaves). In some embodiments, the pulmonary disease is recurrent airway obstruction (RAO), e.g., previously known as chronic obstructive pulmonary disease (COPD). In some embodiments, the pulmonary disease is selected from viral respiratory infections such as equine herpesvirus infection, equine influenza, equine viral arteritis, and Hendra virus infection; secondary bacterial respiratory infections such as those caused by *Streptococcus equi zooepidemicus, Actinobacillus equuli, Bordetella bronchiseptica, Escherichia coli, Pasteurella* spp, *Pseudomonas aeruginosa*, or *S equi equi*, and resultant in mucosal bacterial infections (e.g., rhinitis and tracheitis) or resultant invasive disease (e.g., pneumonia and pleuropneumonia). In some embodiments, the formulations disclosed are suitable for treating, alleviating, or preventing one or more symptoms associated with rhinitis, tracheitis, pneumonia, or pleuropneumonia.

In some embodiments, methods of managing or treating a pulmonary disease in dogs and cats are provided. In some embodiments, the devices described herein can be used for, and products (e.g., variable density, size, or phase products) generated by the devices described herein can be administered for treating, alleviating, or preventing one or more symptoms associated with a pulmonary disease in dogs and cats. Non-limiting exemplary pulmonary diseases in dogs or cats include obstructive airway diseases (such as, but not limited to, Brachycephalic Obstructive Airway Syndrome (BOAS)), COPD, and allergic lung diseases such as asthma, bronchitis, or bronchial asthma.

The invention will be further described in the following examples, which do not limit the scope of the invention described in the claims.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Embodiment 1 is a delivery device comprising:
a first chamber;
one or more heating plates, wherein at least a portion of the one or more heating plates is positioned adjacent to a proximal portion of the first chamber; and
one or more heating coils surrounding a distal portion of the first chamber.

Embodiment 2 is the delivery device of embodiment 1, wherein the delivery device is an inhalation delivery device.

3. The delivery device of any one of embodiments 1 or 2, wherein the proximal portion of the first chamber is narrower than the distal portion of the first chamber.

4. The delivery device of any one of embodiments 1-3, wherein the first chamber has a proximal end and a distal end and a width or diameter that increases from the proximal end of the first chamber to the distal end of the first chamber.

5. The delivery device of any one of embodiments 1-4, wherein the width or diameter increases at a constant rate from the proximal end of the first chamber to the distal end of the first chamber.

6. The delivery device of any one of embodiments 1-5, wherein the one or more heating plates have a proximal end that is thinner than a distal end of the heating plates.

7. The delivery device of any one of embodiments 1-6, wherein the one or more heating plates have a proximal end that is positioned further away from the first chamber than a distal end of the heating plates.

8. The delivery device of any one of embodiments 1-7, wherein the one or more heating plates are positioned such that the distance between a sidewall of the first chamber and the one or more heating plates decreases along a flow axis.

9. The delivery device of any one of embodiments 1-8, wherein the distal end of the one or more heating plates is positioned adjacent to the proximal portion of the first chamber.

10. The delivery device of any one of embodiments 1-9, wherein the one or more heating coils have a proximal end and a distal end and wherein the proximal end of the one or more heating coils has a smaller diameter than the distal end of the one or more heating coils.

11. The delivery device of any one of embodiments 1-10, wherein the proximal end of the first chamber is positioned adjacent a portion of the one or more heating plates that lies between the proximal and distal ends of the one or more heating plates.

12. The delivery device of any one of embodiments 1-11, wherein the proximal end of the first chamber comprises an aperture.

13. The delivery device of any one of embodiments 1-12, wherein the distal end of the first chamber comprises an aperture.

14. The delivery device of any one of embodiments 1-13, wherein the distal end of the first chamber comprises a valve.

15. The delivery device of any one of embodiments 1-14, further comprising a second chamber having a proximal end and a distal end, wherein the first chamber has a distal end, and wherein the proximal end of the second chamber is in fluid connection with the distal end of the first chamber.

16. The delivery device of embodiment 15, wherein the second chamber has a width or diameter greater than the width or diameter of the first chamber at the distal end of the first chamber.

17. The delivery device of any one of embodiments 15 or 16, wherein the second chamber is a cooling chamber.

18. The delivery device of any one of embodiments 15-17, wherein the distal end of the second chamber comprises an aperture 19. The delivery device of any one of embodiments 15-18, wherein the aperture at the distal end of the second chamber comprises a valve.

20. The delivery device of any one of embodiments 15-19, wherein the distal end of the second chamber comprises a subject interface portion 21. The delivery device of any one of embodiments 1-14, wherein the distal end of the first chamber comprises a subject interface portion 22. The delivery device of any one of embodiments 14 or 19, wherein the valve is a one-way valve 23. The delivery device of any one of embodiments 20 or 21, wherein the subject interface portion is a mouthpiece.

24. The delivery device of any one of embodiments 1-23, further comprising a vessel receiving region 25. The delivery device of embodiments 24, wherein the vessel receiving region is upstream of the first chamber.

26. The delivery device of any one of embodiments 1-25, further comprising a vessel in fluid communication with the proximal end of the first chamber.

27. The delivery device of embodiment 26, wherein the vessel comprises a therapeutic agent.

28. The delivery device of any one of embodiments 26 or 27, wherein the vessel is removable.

29. The delivery device of any one of embodiments 1-28, further comprising a power supply.

30. The delivery device of any one of embodiments 1-29, further comprising a housing surrounding the first chamber, the second chamber, the one or more heating plates, the one or more heating coils, the vessel receiving region, the vessel, the power supply, or combinations thereof.

31. The delivery device of embodiments 30, wherein the housing comprises a removable portion.

32. The delivery device of embodiments 31, wherein the removable portion is adjacent to or proximal to the vessel receiving region.

33. The delivery device of any one of embodiments 31 or 32, wherein the removable portion is positioned so as to provide access to the vessel receiving region.

34. The delivery device of any one of embodiments 31-33, further comprising a power supply within the housing, wherein the removable portion is positioned so as to provide access to the power supply.

35. An inhaler comprising the delivery device of any one of embodiments 1-34.

36. The inhaler of embodiments 35, wherein the delivery device comprises a product substrate.

37. The inhaler of embodiment 36, wherein the product substrate comprises one or more active agents selected from acetyl cysteine, aclidinium bromide, albuterol, albuterol sulfate, amikacin sulfate, amniotic fluid, an amnion tissue preparation, arformoterol sulfate, atropine sulfate, aztreonam, beclomethasone dipropionate, bitolterol mesylate, budesonide, ciclesonide, cromolyn sodium, desflurane, dexamethasone sodium phosphate, dornase alfa, enflurane, epinephrine, ergotamine tartrate, flunisolide, fluticasone propionate, fomoterol fumarate, glycopyrrolate, halothane, indacaterol maleate, iloprost, insulin, ipratropium bromide, isoetharine hydrochloride, isoflurane, isoproterenol hydrochloride, levalbuterol hydrochloride, levodopa, loxapine, mannitol, metaproterenol sulfate, methacholine chloride, mometasone furoate, nedocromil sodium, nicotine, nitric oxide, olodaterol hydrochloride, pentamidine isethionate, pentetate calcium trisodium, pentetate zinc trisodium, pirbuterol acetate, revefenacin, ribavirin, salmeterol xinafoate, sevoflurane, stem cells, a stem cell preparation, terbutaline sulfate, tetrahydrocannabinol, cannabidiol, tiotropium bromide, tobramycin, trimcinolone acetonide, umeclidinium bromide, vilanterol trifenatate, xenon xe-133, zanamivir, epinephrine, sodium chloride, and combinations thereof.

38. The inhaler of embodiment 36, wherein the product substrate comprises amniotic fluid, an amnion tissue preparation, or a combination thereof.

39. The inhaler of any one of embodiments 36-38, wherein the product substrate is a liquid.

40. The inhaler of any one of embodiments 36-39, wherein the product substrate is a suspension or a solution.

41. A breathing system comprising:
a pressure-assisted breathing device; and
the delivery device of any one of embodiments 1-34, wherein the delivery device comprises a product substrate.

42. The breathing system of embodiment 41, wherein the delivery device is in fluid communication with an air or oxygen flow channel of the breathing system.

43. The breathing system of any one of embodiments 41 or 42, wherein the pressure-assisted breathing device is a mechanical ventilator.

44. The breathing system of any one of embodiments 41-43, wherein the pressure-assisted breathing device is selected from the group consisting of an intensive care ventilator, a bubble ventilator, a continuous positive airway pressure system, a bi-level positive airway pressure system, an automatic positive airway pressure system, and an adaptive servo ventilation system.

45. The breathing system of any one of embodiments 41-44, wherein the delivery device is operably connected to the breathing system to deliver at least a portion of the product substrate into the breathing system.

46. The breathing system of any one of embodiments 41-44, wherein the delivery device comprises two or more product substrates.

47. The breathing system of any one of embodiments 41-46, wherein the product substrate comprises one or more active agents selected from acetyl cysteine, aclidinium bromide, albuterol, albuterol sulfate, amikacin sulfate, amniotic fluid, an amnion tissue preparation, arformoterol sulfate, atropine sulfate, aztreonam, beclomethasone dipropionate, bitolterol mesylate, budesonide, ciclesonide, cromolyn sodium, desflurane, dexamethasone sodium phosphate, dornase alfa, enflurane, epinephrine, ergotamine tartrate, flunisolide, fluticasone propionate, formoterol fumarate, glycopyrrolate, halothane, indacaterol maleate, iloprost, insulin, ipratropium bromide, isoetharine hydrochloride, isoflurane, isoproterenol hydrochloride, levalbuterol hydrochloride, levodopa, loxapine, mannitol, metaproterenol sulfate, methacholine chloride, mometasone furoate, nedocromil sodium, nicotine, nitric oxide, olodaterol hydrochloride, pentamidine isethionate, pentetate calcium trisodium, pentetate zinc trisodium, pirbuterol acetate, revefenacin, ribavirin, salmeterol xinafoate, sevoflurane, stem cells, a stem cell preparation, terbutaline sulfate, tetrahydrocannabinol, cannabidiol, tiotropium bromide, tobramycin, trimcinolone acetonide, umeclidinium bromide, vilanterol trifenatate, xenon xe-133, zanamivir, epinephrine, sodium chloride, interferon beta, interferon beta 1-b, interferon beta gene delivery, interferon beta-1a, a BKB2R antagonist, a KLKB1 inhibitor, androgens, recombinant SERPING1, vitamin D, a HAS2 or HAS3 inhibitor, timbetasin, and combinations thereof.

48. The breathing system of any one of embodiments 41-46, wherein the product substrate comprises amniotic fluid, an amnion tissue preparation, or a combination thereof.

49. The breathing system of any one of embodiments 46-48, wherein the product substrate is a liquid.

50. The breathing system of any one of embodiments 46-49, wherein the product substrate is a suspension or a solution.

51. A method of producing inhalable products, comprising:
heating a liquid product substrate having a first substrate volume in a vessel comprising a vessel aperture, wherein the aperture is in fluid communication with a first chamber having a proximal portion and a distal portion, and the fluid communication is provided through an aperture in the proximal portion of the first chamber, to produce a mixed product having both gas phase and liquid phase molecules and a second substrate volume that is greater than the first substrate volume.

52. The method of embodiment 51, wherein heating the liquid product substrate comprises heating the liquid product substrate at a first heating rate.

53. The method of embodiment 52, wherein the first heating rate is from about 0.001° C./min to about 150° C./min.

54. The method of any one of embodiments 51-53, wherein the mixed product is present in the first chamber, the vessel, or a combination thereof.

55. The method of any one of embodiments 51-54, wherein the second substrate volume is greater than the volume of the vessel.

56. The method of any one of embodiments 51-55, wherein the mixed product is an inhalable product.

57. The method of any one of embodiments 51-56, further comprising heating the mixed product in the first chamber, the vessel, or a combination thereof, to produce a gaseous product having more at least 80% gas phase molecules.

58. The method of embodiment 57, wherein the gaseous product has a third substrate volume.

59. The method of embodiment 58, wherein the third substrate volume is greater than the volume of the first chamber, the vessel, or a combination thereof.

60. The method of any one of embodiments 58 or 59, wherein the third substrate volume is less than or equal to the volume of the first chamber or a combination of the first chamber and the vessel.

61. The method of any one of embodiments 57-60, wherein heating the mixed product comprises heating the mixed product at the first heating rate.

62. The method of any one of embodiments 57-60, wherein heating the mixed product comprises heating the mixed product at a second heating rate.

63. The method of embodiment 62, wherein the second heating rate is from about 0.001° C./min to about 150° C./min.

64. The method of any one of embodiments 57-63, further comprising heating the gaseous product in the first chamber, the vessel, or a combination thereof, to produce a heated gaseous product having a temperature at least 10% higher than the boiling point for the product substrate.

65. The method of any one of embodiments 57-64, further comprising allowing the gaseous product or heated gaseous product to cool to produce a heavy mist product.

66. The method of embodiment 65, wherein the heavy mist product comprises particles or droplets having an average diameter of from about 3.5 microns to about 5 microns.

67. The method of any one of embodiments 65 or 66, wherein allowing the gaseous product or heated gaseous product to cool comprises allowing the gaseous product or heated gaseous product to pass into a second chamber in fluid communication with the first chamber, wherein the second chamber has a lower temperature than the first chamber.

68. The method of any one of embodiments 65 or 66, wherein allowing the gaseous product or heated gaseous product to cool comprises allowing the gaseous product or heated gaseous product to pass into a breathing system.

69. The method of any one of embodiments 65 or 66, wherein allowing the gaseous product or heated gaseous product to cool comprises allowing the gaseous product or heated gaseous product to pass into a subject's oral cavity.

70. The method of any one of embodiments 51-66 or 68-69, wherein the product exits the first chamber through a valve actuated by negative pressure.

71. The method of embodiment 70, wherein the product enters a subject or a breathing system upon exiting the first chamber.

72. The method of embodiment 67, wherein the product exits the second chamber through a valve actuated by negative pressure.

73. The method of embodiment 72, wherein the product enters a subject or a breathing system upon exiting the second chamber.

74. The method of any one of embodiments 70-73, wherein the valve is a one-way valve.

75. The method of any one of embodiments 51-74, wherein the proximal portion of the first chamber has a smaller volume than the distal portion of the first chamber.

76. The method of any one of embodiments 51-75, wherein the first chamber is heated.

77. The method of any one of embodiments 51-76, wherein the first chamber is heated by one or more heating plates, heating coils, or a combination thereof.

78. The method of any one of embodiments 51-77, wherein the proximal portion of the first chamber is positioned adjacent to at least a portion of one or more heating plates; and wherein one or more heating coils surround the distal portion of the first chamber.

79. A method of treating a subject having a disorder or providing prophylaxis to a subject to prevent or reduce the severity of a developing disorder, comprising:
    delivering inhalable products to the subject through the breathing system according to any one of embodiments 41-50 while mechanically ventilating the subject with the breathing system, or
    delivering inhalable products to the subject through the delivery device according to any one of embodiments 1-34 or through the inhaler according to any one of embodiments 35-40.

80. The method of embodiment 79, wherein the inhalable products comprise one or more active agents selected from acetyl cysteine, aclidinium bromide, albuterol, albuterol sulfate, amikacin sulfate, amniotic fluid, an amnion tissue preparation, arfonnoterol sulfate, atropine sulfate, aztreonam, beclomethasone dipropionate, bitolterol mesylate, budesonide, ciclesonide, cromolyn sodium, desflurane, dexamethasone sodium phosphate, dornase alfa, enflurane, epinephrine, ergotamine tartrate, flunisolide, fluticasone propionate, fomoterol fumarate, glycopyrrolate, halothane, indacaterol maleate, iloprost, insulin, ipratropium bromide, isoetharine hydrochloride, isoflurane, isoproterenol hydrochloride, levalbuterol hydrochloride, levodopa, loxapine, mannitol, metaproterenol sulfate, methacholine chloride, mometasone furoate, nedocromil sodium, nicotine, nitric oxide, olodaterol hydrochloride, pentamidine isethionate, pentetate calcium trisodium, pentetate zinc trisodium, pirbuterol acetate, revefenacin, ribavirin, salmeterol xinafoate, sevoflurane, stem cells, a stem cell preparation, terbutaline sulfate, tetrahydrocannabinol, cannabidiol, tiotropium bromide, tobramycin, trimcinolone acetonide, umeclidinium bromide, vilanterol trifenatate, xenon xe-133, zanamivir, epinephrine, sodium chloride, interferon beta, interferon beta 1-b, interferon beta gene delivery, interferon beta-1a, a BKB2R antagonist, a KLKB1 inhibitor, androgens, recombinant SERPING1, vitamin D, a HAS2 or HAS3 inhibitor, timbetasin, and combinations thereof.

81. The method of any one of embodiments 79 or 80, wherein the inhalable products comprise amniotic fluid, an amnion tissue preparation, or a combination thereof.

82. The method of any one of embodiments 79-81, further comprising actuating the delivery device to deliver one or more doses of the inhalable products into the subject, the breathing system, or a combination thereof.

83. The method of any one of embodiments 79-82, wherein the inhalable products are delivered to the subject as a solution aerosol, a suspension aerosol, a vapor, or a heavy mist.

84. The method of any one of embodiments 79-83, wherein at least a portion of the inhalable products transform into a heavy mist within the breathing system, the subject, or a combination thereof.

85. The method of any one of embodiments 79-84, wherein the inhalable products are delivered in particulate or droplet form having an average diameter of from about 0.1 microns to about 5 microns.

86. The method of any one of embodiments 79-85, wherein the inhalable products are delivered in particulate or droplet form having an average diameter of from about 1 micron to about 5 microns.

87. The method of any one of embodiments 79-85, wherein the inhalable products are delivered in particulate or droplet form having an average diameter of from about 2.5 microns to about 4.5 microns.

88. The method of any one of embodiments 79-85, wherein the inhalable products are delivered in particulate or droplet form having an average diameter of from about 3.5 microns to about 5 microns.

89. The method of any one of embodiments 79-88, further comprising identifying the subject as having or at risk of developing the disorder.

90. The method of any one of embodiments 79-89, further comprising identifying the disorder or one or more symptoms of the disorder.

91. The method of any one of embodiments 79-90, wherein the disorder is a respiratory disorder.

92. The method of embodiment 91, wherein the respiratory disorder is selected from chronic obstructive pulmonary disease, asthma, acute asthma, chronic asthma, severe asthma, allergic asthma, bronchial asthma, intrinsic asthma, respiratory distress syndrome of the newborn, reversible respiratory disease, cystic fibrosis, bronchospasms, bronchitis, chronic bronchitis, bronchiectasis, alpha-1 antitrypsin emphysema, emphysema, associated cor pulmonale with pulmonary hypertension, right ventricular hypertrophy and right heart failure, pulmonary hypertension, interstitial lung disease, pulmonary fibrosis, pneumonia, interstitial pneumonia, a lung infection, idiopathic pulmonary fibrosis, cystic fibrosis, tuberculosis, severe acute respiratory syndrome, infection, pulmonary embolus, pulmonary arterial hypertension, pulmonary edema, *pneumocystis* pneumonia, SARS-CoV-2 infection, covid-19, acute respiratory distress syndrome, intensive care unit (ICU) syndrome, systemic inflammatory response syndrome (SIRS), sepsis, severe sepsis, septic shock, or multiple organ dysfunction syndrome (MODS), cystic fibrosis, sarcoidosis, and combinations thereof.

93. The method of any one of embodiments 79-90, wherein the disorder is a non-respiratory disorder.

94. The method of embodiment 93, wherein the non-respiratory disorder is selected from an autoimmune disease, a spondyloarthropathy, an intestinal disease, diabetes, a skin disease, a non-respiratory infection, a pain disorder, intensive care unit (ICU) syndrome, systemic inflammatory response syndrome (SIRS), sepsis, severe sepsis, septic shock, or multiple organ dysfunction syndrome (MODS), cystic fibrosis, sarcoidosis, and combinations thereof.

95. The method of any one of embodiments 79-94, wherein the inhalable products consist essentially of amniotic fluid, an amnion tissue preparation, or a combination thereof.

96. The method of embodiment 95, wherein the amniotic fluid or the amnion tissue preparation lacks viable cells.

97. The method of embodiment 95, wherein the amniotic fluid or the amnion tissue preparation comprises viable cells.

98. The method of any one of embodiments 79-97, wherein delivering inhalable products to the subject through the delivery device or through the inhaler comprises delivering the inhalable products, by way of ambulatory inhalation from the delivery device or the inhaler.

99. A method of treating a subject having a disorder, comprising:
administering, to lung tissue of the subject, inhalable products, through the breathing system according to any one of embodiments 41-50 while mechanically ventilating the subject with the breathing system, or administering, to lung tissue of the subject, inhalable products, through the delivery device according to any one of embodiments 1-34 or through the inhaler according to any one of embodiments 35-40.

100. The method of embodiment 99, wherein the administering occurs through ambulatory inhalation of the inhalable products by the subject from the delivery device or the inhaler.

101. The method of any one of embodiments 99 or 100, wherein the disorder is a non-respiratory disorder.

102. The method of embodiment 101, wherein the non-respiratory disorder is selected from an autoimmune disease, a spondyloarthropathy, an intestinal disease, diabetes, a skin disease, a non-respiratory infection, a pain disorder, intensive care unit (ICU) syndrome, systemic inflammatory response syndrome (SIRS), sepsis, severe sepsis, septic shock, or multiple organ dysfunction syndrome (MODS), cystic fibrosis, sarcoidosis, and combinations thereof.

103. The method of embodiment 102, wherein the inhalable products comprise one or more active agents selected from acetyl cysteine, aclidinium bromide, albuterol, albuterol sulfate, amikacin sulfate, amniotic fluid, an amnion tissue preparation, arformoterol sulfate, atropine sulfate, aztreonam, beclomethasone dipropionate, bitolterol mesylate, budesonide, ciclesonide, cromolyn sodium, desflurane, dexamethasone sodium phosphate, dornase alfa, enflurane, epinephrine, ergotamine tartrate, flunisolide, fluticasone propionate, fomoterol fumarate, glycopyrrolate, halothane, indacaterol maleate, iloprost, insulin, ipratropium bromide, isoetharine hydrochloride, isoflurane, isoproterenol hydrochloride, levalbuterol hydrochloride, levodopa, loxapine, mannitol, metaproterenol sulfate, methacholine chloride, mometasone furoate, nedocromil sodium, nicotine, nitric oxide, olodaterol hydrochloride, pentamidine isethionate, pentetate calcium trisodium, pentetate zinc trisodium, pirbuterol acetate, revefenacin, ribavirin, salmeterol xinafoate, sevoflurane, stem cells, a stem cell preparation, terbutaline sulfate, tetrahydrocannabinol, cannabidiol, tiotropium bromide, tobramycin, trimcinolone acetonide, umeclidinium bromide, vilanterol trifenatate, xenon xe-133, zanamivir, epinephrine, sodium chloride, interferon beta, interferon beta 1-b, interferon beta gene delivery, interferon beta-1a, a BKB2R antagonist, a KLKB1 inhibitor, androgens, recombinant SERPING1, vitamin D, a HAS2 or HAS3 inhibitor, timbetasin, and combinations thereof.

104. The method of any one of embodiments 99 or 100, wherein the disorder is a respiratory disorder.

105. The method of embodiment 104, wherein the respiratory disorder is selected from chronic obstructive pulmonary disease, asthma, acute asthma, chronic asthma, severe asthma, allergic asthma, bronchial asthma, intrinsic asthma, respiratory distress syndrome of the newborn, reversible respiratory disease, cystic fibrosis, bronchospasms, bronchitis, chronic bronchitis, bronchiectasis, alpha-1 antitrypsin emphysema, emphysema, associated cor pulmonale with pulmonary hypertension, right ventricular hypertrophy and right heart failure, pulmonary hypertension, interstitial lung disease, pulmonary fibrosis, pneumonia, interstitial pneumonia, a lung infection, idiopathic pulmonary fibrosis, cystic fibrosis, tuberculosis, severe acute respiratory syndrome, infection, pulmonary embolus, pulmonary arterial hypertension, pulmonary edema, *pneumocystis* pneumonia, SARS-CoV-2 infection, covid-19, acute respiratory distress syndrome, intensive care unit (ICU) syndrome, systemic inflammatory response syndrome (SIRS), sepsis, severe sepsis, septic shock, or multiple organ dysfunction syndrome (MODS), cystic fibrosis, sarcoidosis, and combinations thereof.

106. The method of embodiment 105, wherein the inhalable products comprise one or more active agents selected from acetyl cysteine, aclidinium bromide, albuterol, albuterol sulfate, amikacin sulfate, amniotic fluid, an amnion tissue preparation, arformoterol sulfate, atropine sulfate, aztreonam, beclomethasone dipropionate, bitolterol mesylate, budesonide, ciclesonide, cromolyn sodium, desflurane, dexamethasone sodium phosphate, dornase alfa, enflurane, epinephrine, ergotamine tartrate, flunisolide, fluticasone propionate, fomoterol fumarate, glycopyrrolate, halothane, indacaterol maleate, iloprost, insulin, ipratropium bromide, isoetharine hydrochloride, isoflurane, isoproterenol hydrochloride, levalbuterol hydrochloride, levodopa, loxapine, mannitol, metaproterenol sulfate, methacholine chloride, mometasone furoate, nedocromil sodium, nicotine, nitric oxide, olodaterol hydrochloride, pentamidine isethionate, pentetate calcium trisodium, pentetate zinc trisodium, pirbuterol acetate, revefenacin, ribavirin, salmeterol xinafoate, sevoflurane, stem cells, a stem cell preparation, terbutaline sulfate, tetrahydrocannabinol, cannabidiol, tiotropium bromide, tobramycin, trimcinolone acetonide, umeclidinium bromide, vilanterol trifenatate, xenon xe-133, zanamivir, epinephrine, sodium chloride, interferon beta, interferon beta 1-b, interferon beta gene delivery, interferon beta-1a, a BKB2R antagonist, a KLKB1 inhibitor, androgens, recombinant SERPING1, vitamin D, a HAS2 or HAS3 inhibitor, timbetasin, and combinations thereof.

107. The method of embodiment 105, wherein the inhalable products consist essentially of amniotic fluid, an amnion tissue preparation, or a combination thereof.

108. The method of embodiment 107, wherein the amniotic fluid or the amnion tissue preparation lacks viable cells.

109. The method of embodiment 107, wherein the amniotic fluid or the amnion tissue preparation comprises viable cells.

110. The method of any one of embodiments 104-109, wherein the administering occurs simultaneously with or after acute treatment of a respiratory disorder.

111. The method of embodiment 110, wherein the acute treatment comprises mechanical ventilation, oxygen administration, or a combination thereof.

112. The method of any one of embodiments 110 or 111, wherein the administering occurs after the subject has been discharged from hospital care, downgraded from intensive care, downgraded from acute care, downgraded from critical care, or removed from acute care treatment.

113. The method of embodiment 112, wherein the administering occurs more than 1 day, more than 2 days, more than 3 days, more than 1 week, more than 2 weeks, more than 3 weeks, more than 6 weeks, more than 8 weeks, more than 10 weeks, or more than 15 weeks after the subject has been discharged from hospital care, downgraded from intensive care, downgraded from acute care, downgraded from critical care, or removed from acute care treatment.

114. The method of any one of embodiments 110-113, wherein the administering includes administering once daily, multiple times daily, every other day, weekly, or monthly for a period of from about 1 day to about 10 years following the acute treatment.

115. A method of providing maintenance treatment to a subject following an acute treatment of a respiratory disorder in the subject, comprising:
administering, to lung tissue of the subject, through the delivery device according to any one of embodiments 1-34 or through the inhaler according to any one of embodiments 35-40, inhalable products,
wherein the administering occurs after completion of acute treatment of the subject's respiratory disorder.

116. The method of embodiment 115, wherein the acute treatment comprises mechanical ventilation, oxygen administration, or a combination thereof.

117. The method of any one of embodiments 115 or 116, wherein the administering occurs after the subject has been discharged from hospital care, downgraded from intensive care, downgraded from acute care, downgraded from critical care, or removed from acute care treatment.

118. The method of embodiment 117, wherein the administering occurs more than 1 day, more than 2 days, more than 3 days, more than 1 week, more than 2 weeks, more than 3 weeks, more than 6 weeks, more than 8 weeks, more than 10 weeks, or more than 15 weeks after the subject has been discharged from hospital care, downgraded from intensive care, downgraded from acute care, downgraded from critical care, or removed from acute care treatment.

119. The method of any one of embodiments 115-118, wherein the administering includes administering once daily, multiple times daily, every other day, weekly, or monthly for a period of from about 1 day to about 10 years following the acute treatment.

120. The method of any one of embodiments 115-119, wherein the respiratory disorder is selected from chronic obstructive pulmonary disease, asthma, acute asthma, chronic asthma, severe asthma, allergic asthma, bronchial asthma, intrinsic asthma, respiratory distress syndrome of the newborn, reversible respiratory disease, cystic fibrosis, bronchospasms, bronchitis, chronic bronchitis, bronchiectasis, alpha-1 antitrypsin emphysema, emphysema, associated cor pulmonale with pulmonary hypertension, right ventricular hypertrophy and right heart failure, pulmonary hypertension, interstitial lung disease, pulmonary fibrosis, pneumonia, interstitial pneumonia, a lung infection, idiopathic pulmonary fibrosis, cystic fibrosis, tuberculosis, severe acute respiratory syndrome, infection, pulmonary embolus, pulmonary arterial hypertension, pulmonary edema, *pneumocystis* pneumonia, SARS-CoV-2 infection, covid-19, acute respiratory distress syndrome, intensive care unit (ICU) syndrome, systemic inflammatory response syndrome (SIRS), sepsis, severe sepsis, septic shock, or multiple organ dysfunction syndrome (MODS), cystic fibrosis, sarcoidosis, and combinations thereof.

121. The method of any one of embodiments 115-120, wherein the inhalable products comprise one or more active agents selected from acetyl cysteine, aclidinium bromide, albuterol, albuterol sulfate, amikacin sulfate, amniotic fluid, an amnion tissue preparation, arformoterol sulfate, atropine sulfate, aztreonam, beclomethasone dipropionate, bitolterol mesylate, budesonide, ciclesonide, cromolyn sodium, desflurane, dexamethasone sodium phosphate, dornase alfa, enflurane, epinephrine, ergotamine tartrate, flunisolide, fluticasone propionate, fomoterol fumarate, glycopyrrolate, halothane, indacaterol maleate, iloprost, insulin, ipratropium bromide, isoetharine hydrochloride, isoflurane, isoproterenol hydrochloride, levalbuterol hydrochloride, levodopa, loxapine, mannitol, metaproterenol sulfate, methacholine chloride, mometasone furoate, nedocromil sodium, nicotine, nitric oxide, olodaterol hydrochloride, pentamidine isethionate, pentetate calcium trisodium, pentetate zinc trisodium, pirbuterol acetate, revefenacin, ribavirin, salmeterol xinafoate, sevoflurane, stem cells, a stem cell preparation, terbutaline sulfate, tetrahydrocannabinol, cannabidiol, tiotropium bromide, tobramycin, trimcinolone acetonide, umeclidinium bromide, vilanterol trifenatate, xenon xe-133, zanamivir, epinephrine, sodium chloride, interferon beta, interferon beta 1-b, interferon beta gene delivery, interferon beta-1a, a BKB2R antagonist, a KLKB1 inhibitor, androgens, recombinant SERPING1, vitamin D, a HAS2 or HAS3 inhibitor, timbetasin, and combinations thereof.

122. The method of any one of embodiments 115-121, wherein the inhalable products consist essentially of amniotic fluid, an amnion tissue preparation, or a combination thereof.

123. The method of embodiment 122, wherein the amniotic fluid or the amnion tissue preparation lacks viable cells.

124. The method of embodiment 122, wherein the amniotic fluid or the amnion tissue preparation comprises viable cells.

125. A method of regenerating or restoring respiratory tissue or respiratory function in a subject following an acute respiratory disorder in the subject, comprising:
administering, to lung tissue of the subject, through the delivery device according to any one of embodiments 1-34 or through the inhaler according to any one of embodiments 35-40, inhalable products comprising amniotic fluid, an amnion tissue preparation, or a combination thereof.

126. The method of embodiment 125, wherein the administering occurs after acute treatment of a respiratory disorder.

127. The method of claim embodiment, wherein the acute treatment comprises mechanical ventilation, oxygen administration, or a combination thereof.

128. The method of any one of embodiments 125-127, wherein the administering occurs after the subject has been discharged from hospital care, downgraded from intensive care, downgraded from acute care, downgraded from critical care, or removed from acute care treatment.

129. The method of embodiment 128, wherein the administering occurs more than 1 day, more than 2 days, more than 3 days, more than 1 week, more than 2 weeks, more than 3 weeks, more than 6 weeks, more than 8 weeks, more than 10 weeks, or more than 15 weeks after the subject has been discharged from hospital care, downgraded from intensive care, downgraded from acute care, downgraded from critical care, or removed from acute care treatment.

130. The method of any one of embodiments 125-129, wherein the administering includes administering once daily, multiple times daily, every other day, weekly, or monthly for a period of from about 1 day to about 10 years following the acute treatment.

131. The method of any one of embodiments 125-130, wherein the respiratory disorder is selected from chronic obstructive pulmonary disease, asthma, acute asthma, chronic asthma, severe asthma, allergic asthma, bronchial asthma, intrinsic asthma, respiratory distress syndrome of the newborn, reversible respiratory disease, cystic fibrosis, bronchospasms, bronchitis, chronic bronchitis, bronchiectasis, alpha-1 antitrypsin emphysema, emphysema, associated cor pulmonale with pulmonary hypertension, right ventricular hypertrophy and right heart failure, pulmonary hypertension, interstitial lung disease, pulmonary fibrosis, pneumonia, interstitial pneumonia, a lung infection, idiopathic pulmonary fibrosis, cystic fibrosis, tuberculosis, severe acute respiratory syndrome, infection, pulmonary embolus, pulmonary arterial hypertension, pulmonary edema, *pneumocystis* pneumonia, covid-19, and acute respiratory distress syndrome, intensive care unit (ICU) syndrome, systemic inflammatory response syndrome (SIRS), sepsis, severe sepsis, septic shock, or multiple organ dysfunction syndrome (MODS), cystic fibrosis, sarcoidosis, and combinations thereof.

132. The device of embodiment 27, wherein the therapeutic agent is one or more active agents selected from acetyl cysteine, aclidinium bromide, albuterol, albuterol sulfate, amikacin sulfate, amniotic fluid, an amnion tissue preparation, arformoterol sulfate, atropine sulfate, aztreonam, beclomethasone dipropionate, bitolterol mesylate, budesonide, ciclesonide, cromolyn sodium, desflurane, dexamethasone sodium phosphate, dornase alfa, enflurane, epinephrine, ergotamine tartrate, flunisolide, fluticasone propionate, fomoterol fumarate, glycopyrrolate, halothane, indacaterol maleate, iloprost, insulin, ipratropium bromide, isoetharine hydrochloride, isoflurane, isoproterenol hydrochloride, levalbuterol hydrochloride, levodopa, loxapine, mannitol, metaproterenol sulfate, methacholine chloride, mometasone furoate, nedocromil sodium, nicotine, nitric oxide, olodaterol hydrochloride, pentamidine isethionate, pentetate calcium trisodium, pentetate zinc trisodium, pirbuterol acetate, revefenacin, ribavirin, salmeterol xinafoate, sevoflurane, stem cells, a stem cell preparation, terbutaline sulfate, tetrahydrocannabinol, cannabidiol, tiotropium bromide, tobramycin, trimcinolone acetonide, umeclidinium bromide, vilanterol trifenatate, xenon xe-133, zanamivir, epinephrine, sodium chloride, interferon beta, interferon beta 1-b, interferon beta gene delivery, interferon beta-1a, a BKB2R antagonist, a KLKB1 inhibitor, androgens, recombinant SERPING1, vitamin D, a HAS2 or HAS3 inhibitor, timbetasin, and combinations thereof.

What is claimed is:
1. An inhalation delivery device comprising:
a first chamber;
one or more heating plates, wherein at least a portion of the one or more heating plates is positioned adjacent to a proximal portion of the first chamber; and
one or more heating coils surrounding a distal portion of the first chamber and wherein the one or more heating plates are positioned such that the distance between a sidewall of the first chamber and the one or more heating plates decreases along a flow axis.

2. The delivery device of claim 1, wherein the first chamber has a proximal end and a distal end and a width or diameter that increases from the proximal end of the first chamber to the distal end of the first chamber.

3. The delivery device of claim 1, wherein the one or more heating plates have a proximal end that is thinner than a distal end of the heating plates.

4. The delivery device of claim 1, wherein the one or more heating plates have a proximal end that is positioned further away from the first chamber than a distal end of the heating plates.

5. The delivery device of claim 1, wherein the distal end of the one or more heating plates is positioned adjacent to the proximal portion of the first chamber.

6. The delivery device of claim 1, wherein the one or more heating coils have a proximal end and a distal end and wherein the proximal end of the one or more heating coils has a smaller diameter than the distal end of the one or more heating coils.

7. The delivery device of claim 1, wherein the proximal end of the first chamber is positioned adjacent a portion of the one or more heating plates that lies between the proximal and distal ends of the one or more heating plates.

8. The delivery device 1, wherein the proximal end of the first chamber comprises an aperture and the distal end of the first chamber comprises an aperture.

9. The delivery device of claim 8, wherein the distal end of the first chamber a valve.

10. The delivery device of claim 1, further comprising a second chamber having a proximal end and a distal end, wherein the first chamber has a distal end, and wherein the proximal end of the second chamber is in fluid connection with the distal end of the first chamber.

11. The delivery device of claim 10, wherein the second chamber has a width or diameter greater than the width or diameter of the first chamber at the distal end of the first chamber.

12. The delivery device of claim 10, wherein the second chamber is a cooling chamber.

13. The delivery device of claim 10, wherein the distal end of the second chamber comprises an aperture.

14. The delivery device of claim 13, wherein the aperture at the distal end of the second chamber comprises a valve.

15. The delivery device of claim 14, wherein the valve is a one-way valve.

16. The delivery device of claim 10, wherein the distal end of the second chamber comprises a subject interface portion.

17. The delivery device of claim 10, further comprising a vessel receiving region, wherein the vessel receiving region is upstream of the first chamber.

18. The delivery device of claim 10, further comprising a vessel in fluid communication with the proximal end of the first chamber.

19. The delivery device of claim 18, wherein the vessel comprises a therapeutic agent.

20. The delivery device of claim 19, wherein the vessel is removable.

21. The device of claim 19, wherein the therapeutic agent is one or more active agents selected from acetyl cysteine, aclidinium bromide, albuterol, albuterol sulfate, amikacin sulfate, amniotic fluid, an amnion tissue preparation, arformoterol sulfate, atropine sulfate, aztreonam, beclomethasone dipropionate, bitolterol mesylate, budesonide, ciclesonide, cromolyn sodium, desflurane, dexamethasone sodium phosphate, dornase alfa, enflurane, epinephrine, ergotamine tartrate, flunisolide, fluticasone propionate, fomoterol fumarate, glycopyrrolate, halothane, indacaterol maleate, iloprost, insulin, ipratropium bromide, isoetharine hydrochloride, isoflurane, isoproterenol hydrochloride, levalbuterol hydrochloride, levodopa, loxapine, mannitol, metaproterenol sulfate, methacholine chloride, mometasone furoate, nedocromil sodium, nicotine, nitric oxide, olodaterol hydrochloride, pentamidine isethionate, pentetate calcium trisodium, pentetate zinc trisodium, pirbuterol acetate, revefenacin, ribavirin, salmeterol xinafoate, sevoflurane, stem cells, a stem cell preparation, terbutaline sulfate, tetrahydrocannabinol, cannabidiol, tiotropium bromide, tobramycin, trimcinolone acetonide, umeclidinium bromide, vilanterol trifenatate, xenon xe-133, zanamivir, epinephrine, sodium chloride, interferon beta, interferon beta 1-b, interferon beta gene delivery, interferon beta-1a, a BKB2R antagonist, a KLKB1 inhibitor, androgens, recombinant SERPING1, vitamin D, a HAS2 or HAS3 inhibitor, timbetasin, and combinations thereof.

22. The delivery device of claim 10, further comprising a power supply.

23. An inhaler comprising the delivery device of claim 10, wherein the delivery device comprises a product substrate.

24. The inhaler of claim 23, wherein the product substrate comprises one or more active agents selected from acetyl cysteine, aclidinium bromide, albuterol, albuterol sulfate, amikacin sulfate, amniotic fluid, an amnion tissue preparation, arformoterol sulfate, atropine sulfate, aztreonam, beclomethasone dipropionate, bitolterol mesylate, budesonide, ciclesonide, cromolyn sodium, desflurane, dexamethasone sodium phosphate, dornase alfa, enflurane, epinephrine, ergotamine tartrate, flunisolide, fluticasone propionate, fomoterol fumarate, glycopyrrolate, halothane, indacaterol maleate, iloprost, insulin, ipratropium bromide, isoetharine hydrochloride, isoflurane, isoproterenol hydrochloride, levalbuterol hydrochloride, levodopa, loxapine, mannitol, metaproterenol sulfate, methacholine chloride, mometasone furoate, nedocromil sodium, nicotine, nitric oxide, olodaterol hydrochloride, pentamidine isethionate, pentetate calcium trisodium, pentetate zinc trisodium, pirbuterol acetate, revefenacin, ribavirin, salmeterol xinafoate, sevoflurane, stem cells, a stem cell preparation, terbutaline sulfate, tetrahydrocannabinol, cannabidiol, tiotropium bromide, tobramycin, trimcinolone acetonide, umeclidinium bromide, vilanterol trifenatate, xenon xe-133, zanamivir, epinephrine, sodium chloride, interferon beta, interferon beta 1-b, interferon beta gene delivery, interferon beta-1a, a BKB2R antagonist (e.g., icatibant), a KLKB1 inhibitor (e.g., ecallantide), androgens (e.g., danazol and stanasolol), recombinant SERPING1 (e.g., berinert, cinryze, haegarda), vitamin D, a HAS2 or HAS3 inhibitor (e.g., hymecromone (4-methylumbelliferone)), timbetasin, and combinations thereof.

25. A breathing system comprising:
a pressure-assisted breathing device; and
the delivery device of claim 10, wherein the delivery device comprises a product substrate.

26. The breathing system of claim 25, wherein the delivery device is in fluid communication with an air or oxygen flow channel of the breathing system, and wherein the delivery device is operably connected to the breathing system to deliver at least a portion of the product substrate into the breathing system.

27. The breathing system of claim 25, wherein the product substrate comprises one or more active agents selected from acetyl cysteine, aclidinium bromide, albuterol, albuterol sulfate, amikacin sulfate, amniotic fluid, an amnion tissue preparation, arformoterol sulfate, atropine sulfate, aztreonam, beclomethasone dipropionate, bitolterol mesylate, budesonide, ciclesonide, cromolyn sodium, desflurane, dexamethasone sodium phosphate, dornase alfa, enflurane, epinephrine, ergotamine tartrate, flunisolide, fluticasone propionate, fomoterol fumarate, glycopyrrolate, halothane, indacaterol maleate, iloprost, insulin, ipratropium bromide, isoetharine hydrochloride, isoflurane, isoproterenol hydrochloride, levalbuterol hydrochloride, levodopa, loxapine, mannitol, metaproterenol sulfate, methacholine chloride, mometasone furoate, nedocromil sodium, nicotine, nitric oxide, olodaterol hydrochloride, pentamidine isethionate, pentetate calcium trisodium, pentetate zinc trisodium, pirbuterol acetate, revefenacin, ribavirin, salmeterol xinafoate, sevoflurane, stem cells, a stem cell preparation, terbutaline sulfate, tetrahydrocannabinol, cannabidiol, tiotropium bromide, tobramycin, trimcinolone acetonide, umeclidinium bromide, vilanterol trifenatate, xenon xe-133, zanamivir, epinephrine, sodium chloride, interferon beta, interferon beta 1-b, interferon beta gene delivery, interferon beta-1a, a BKB2R antagonist (e.g., icatibant), a KLKB1 inhibitor (e.g., ecallantide), androgens (e.g., danazol and stanasolol), recombinant SERPING1 (e.g., berinert, cinryze, haegarda), vitamin D, a HAS2 or HAS3 inhibitor (e.g., hymecromone (4-methylumbelliferone)), timbetasin, and combinations thereof.

28. A method of treating a subject having a disorder or providing prophylaxis to a subject to prevent or reduce the severity of a developing disorder, comprising:

delivering inhalable products to the subject through the delivery device according to claim 1, an inhaler comprising the delivery device of claim 1, or a breathing system comprising the delivery device of claim 1.

29. The method of claim 28, wherein the inhalable products comprise one or more active agents selected from acetyl cysteine, aclidinium bromide, albuterol, albuterol sulfate, amikacin sulfate, amniotic fluid, an amnion tissue preparation, arformoterol sulfate, atropine sulfate, aztreonam, beclomethasone dipropionate, bitolterol mesylate, budesonide, ciclesonide, cromolyn sodium, desflurane, dexamethasone sodium phosphate, dornase alfa, enflurane, epinephrine, ergotamine tartrate, flunisolide, fluticasone propionate, fomoterol fumarate, glycopyrrolate, halothane, indacaterol maleate, iloprost, insulin, ipratropium bromide, isoetharine hydrochloride, isoflurane, isoproterenol hydrochloride, levalbuterol hydrochloride, levodopa, loxapine, mannitol, metaproterenol sulfate, methacholine chloride, mometasone furoate, nedocromil sodium, nicotine, nitric oxide, olodaterol hydrochloride, pentamidine isethionate, pentetate calcium trisodium, pentetate zinc trisodium, pirbuterol acetate, revefenacin, ribavirin, salmeterol xinafoate, sevoflurane, stem cells, a stem cell preparation, terbutaline sulfate, tetrahydrocannabinol, cannabidiol, tiotropium bromide, tobramycin, trimcinolone acetonide, umeclidinium bromide, vilanterol trifenatate, xenon xe-133, zanamivir, epinephrine, sodium chloride, interferon beta, interferon beta 1-b, interferon beta gene delivery, interferon beta-1a, a BKB2R antagonist (e.g., icatibant), a KLKB1 inhibitor (e.g., ecallantide), androgens (e.g., danazol and stanasolol), recombinant SERPING1 (e.g., berinert, cinryze, haegarda), vitamin D, a HAS2 or HAS3 inhibitor (e.g., hymecromone (4-methylumbelliferone)), timbetasin, and combinations thereof.

30. The method of claim 28, wherein the disorder is a respiratory disorder or a non-respiratory disorder.

31. The method of claim 30, wherein the respiratory disorder is selected from chronic obstructive pulmonary disease, asthma, acute asthma, chronic asthma, severe asthma, allergic asthma, bronchial asthma, intrinsic asthma, respiratory distress syndrome of the newborn, reversible respiratory disease, cystic fibrosis, bronchospasms, bronchitis, chronic bronchitis, bronchiectasis, alpha-1 antitrypsin emphysema, emphysema, associated cor pulmonale with pulmonary hypertension, right ventricular hypertrophy and right heart failure, pulmonary hypertension, interstitial lung disease, pulmonary fibrosis, pneumonia, interstitial pneumonia, a lung infection, idiopathic pulmonary fibrosis, cystic fibrosis, tuberculosis, severe acute respiratory syndrome, infection, pulmonary embolus, pulmonary arterial hypertension, pulmonary edema, *pneumocystis* pneumonia, SARS-CoV-2 infection, covid-19, acute respiratory distress syndrome, intensive care unit (ICU) syndrome, systemic inflammatory response syndrome (SIRS), sepsis, severe sepsis, septic shock, or multiple organ dysfunction syndrome (MODS), cystic fibrosis, sarcoidosis, and combinations thereof, and wherein the non-respiratory disorder is selected from an autoimmune disease, a spondyloarthropathy, an intestinal disease, diabetes, a skin disease, a non-respiratory infection, a pain disorder, intensive care unit (ICU) syndrome, systemic inflammatory response syndrome (SIRS), sepsis, severe sepsis, septic shock, or multiple organ dysfunction syndrome (MODS), cystic fibrosis, sarcoidosis, and combinations thereof.

32. A method of treating a subject having a disorder, comprising:
administering, to lung tissue of the subject, inhalable products, through the inhaler according to claim 23, wherein the administering occurs through ambulatory inhalation of the inhalable products by the subject from the inhaler.

33. The method of claim 32, wherein the disorder is a non-respiratory disorder or a respiratory disorder, and wherein the administering occurs simultaneously with or after acute treatment of a respiratory disorder.

34. A method of providing maintenance treatment to a subject following an acute treatment of a respiratory disorder in the subject, comprising:
administering, to lung tissue of the subject, through the delivery device according to claim 1 or an inhaler comprising the delivery device of claim 1, inhalable products, wherein the administering occurs after completion of acute treatment of the subject's respiratory disorder.

35. The method of claim 34, wherein the administering occurs more than 1 day, more than 2 days, more than 3 days, more than 1 week, more than 2 weeks, more than 3 weeks, more than 6 weeks, more than 8 weeks, more than 10 weeks, or more than 15 weeks after the subject has been discharged from hospital care, downgraded from intensive care, downgraded from acute care, downgraded from critical care, or removed from acute care treatment.

36. A method of regenerating or restoring respiratory tissue or respiratory function in a subject following an acute respiratory disorder in the subject, comprising:
administering, to lung tissue of the subject, through the delivery device according to claim 1 or through an inhaler comprising the delivery device of claim 1, inhalable products comprising amniotic fluid, an amnion tissue preparation, or a combination thereof.

37. The method of claim 36, wherein the respiratory disorder is selected from chronic obstructive pulmonary disease, asthma, acute asthma, chronic asthma, severe asthma, allergic asthma, bronchial asthma, intrinsic asthma, respiratory distress syndrome of the newborn, reversible respiratory disease, cystic fibrosis, bronchospasms, bronchitis, chronic bronchitis, bronchiectasis, alpha-1 antitrypsin emphysema, emphysema, associated cor pulmonale with pulmonary hypertension, right ventricular hypertrophy and right heart failure, pulmonary hypertension, interstitial lung disease, pulmonary fibrosis, pneumonia, interstitial pneumonia, a lung infection, idiopathic pulmonary fibrosis, cystic fibrosis, tuberculosis, severe acute respiratory syndrome, infection, pulmonary embolus, pulmonary arterial hypertension, pulmonary edema, *pneumocystis* pneumonia, SARS-CoV-2 infection, covid-19, and acute respiratory distress syndrome, intensive care unit (ICU) syndrome, systemic inflammatory response syndrome (SIRS), sepsis, severe sepsis, septic shock, or multiple organ dysfunction syndrome (MODS), cystic fibrosis, sarcoidosis, and combinations thereof.

* * * * *